(12) United States Patent
Saliman

(10) Patent No.: US 10,987,095 B2
(45) Date of Patent: Apr. 27, 2021

(54) SUTURE METHODS FOR FORMING LOCKING LOOPS STITCHES

(71) Applicant: CETERIX ORTHOPAEDICS, INC., Fremont, CA (US)

(72) Inventor: Justin D. Saliman, Beverly Hills, CA (US)

(73) Assignee: Ceterix Orthopaedics, Inc., Fremont, CA (US)

( * ) Notice: Subject to any disclaimer, the term of this patent is extended or adjusted under 35 U.S.C. 154(b) by 475 days.

(21) Appl. No.: 15/853,531

(22) Filed: Dec. 22, 2017

(65) Prior Publication Data

US 2018/0116651 A1    May 3, 2018

Related U.S. Application Data

(63) Continuation of application No. 14/292,695, filed on May 30, 2014, now Pat. No. 9,848,868, which is a
(Continued)

(51) Int. Cl.
*A61B 17/04* (2006.01)
*A61B 17/062* (2006.01)
*A61B 17/06* (2006.01)

(52) U.S. Cl.
CPC ...... *A61B 17/0401* (2013.01); *A61B 17/0625* (2013.01); *A61B 17/0482* (2013.01);
(Continued)

(58) Field of Classification Search
CPC .... A61B 2017/0459; A61B 2017/0469; A61B 2017/0475; A61B 17/04; A61B 17/0401; A61B 17/0625; A61B 17/0482
See application file for complete search history.

(56) References Cited

U.S. PATENT DOCUMENTS

| 1,037,864 A | 9/1912 | Carlson et al. |
|---|---|---|
| 2,738,790 A | 3/1956 | Todt, Sr. et al. |

(Continued)

FOREIGN PATENT DOCUMENTS

| CN | 201263696 Y | 7/2009 |
|---|---|---|
| CN | 101961256 A | 2/2011 |

(Continued)

OTHER PUBLICATIONS

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.
(Continued)

*Primary Examiner* — Christopher D. Prone
(74) *Attorney, Agent, or Firm* — Norman F. Hainer, Jr.

(57) ABSTRACT

Methods for suturing tissue by forming a locking loop of suture material. In particular, method of using a suture passer to arthroscopically create a locking loop of suture in difficult to access tissues. As used herein a locking loop of suture is a loop of suture that is passed through a tissue from a first side to a second side of the tissue; one or more of the legs of the loop extending from the first side are passed through the tissue to the second side of the tissue and are then passed through the loop, and the loop is cinched to tighten closed over the one or more legs. The resulting locking loops stitches are extremely strong and distribute the stresses across the tissue in a desirable manner.

19 Claims, 51 Drawing Sheets

Related U.S. Application Data continuation-in-part of application No. 13/893,209, filed on May 13, 2013, now Pat. No. 8,888,848, which is a continuation of application No. 13/347,184, filed on Jan. 10, 2012, now Pat. No. 8,500,809.

(60) Provisional application No. 61/829,169, filed on May 30, 2013, provisional application No. 61/431,293, filed on Jan. 10, 2011.

(52) U.S. Cl.
CPC . *A61B 2017/044* (2013.01); *A61B 2017/0412* (2013.01); *A61B 2017/0414* (2013.01); *A61B 2017/06042* (2013.01); *A61B 2017/06095* (2013.01)

(56) References Cited

U.S. PATENT DOCUMENTS

| | | |
|---|---|---|
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,616,131 A | 4/1997 | Sauer et al. |
| 5,618,290 A | 4/1997 | Toy et al. |
| 5,626,588 A | 5/1997 | Sauer et al. |
| 5,632,748 A | 5/1997 | Beck et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A | 9/1998 | Schulze et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,099,568 A | 8/2000 | Simonian et al. |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |

(56) References Cited

U.S. PATENT DOCUMENTS

| | | |
|---|---|---|
| 6,159,224 A | 12/2000 | Yoon |
| 6,190,396 B1 | 2/2001 | Whitin et al. |
| 6,221,085 B1 | 4/2001 | Djurovic |
| 6,231,606 B1 | 5/2001 | Graf et al. |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,368,343 B1 | 4/2002 | Bonutti et al. |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,605,096 B1 | 8/2003 | Ritchart |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,833,005 B1 | 12/2004 | Mantas |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,153,312 B1 | 12/2006 | Torrie et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,481,826 B2 | 1/2009 | Cichocki |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,717,927 B2 | 5/2010 | Hahn et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,298,230 B2 | 10/2012 | Sutter et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murillo et al. |
| 8,500,809 B2 | 8/2013 | Saliman |
| 8,562,631 B2 | 10/2013 | Saliman |
| 8,632,563 B2 | 1/2014 | Nagase et al. |
| 8,647,354 B2 | 2/2014 | Domingo |
| 8,663,253 B2 | 3/2014 | Saliman |
| 8,702,731 B2 | 4/2014 | Saliman |
| 8,808,299 B2 | 8/2014 | Saliman et al. |
| 8,821,518 B2 | 9/2014 | Saliman |
| 8,888,848 B2 | 11/2014 | Saliman et al. |
| 8,911,456 B2 | 12/2014 | McCutcheon et al. |
| 8,920,441 B2 | 12/2014 | Saliman et al. |
| 9,011,454 B2 | 4/2015 | Hendrickson et al. |
| 9,211,119 B2 | 12/2015 | Hendricksen et al. |
| 9,247,934 B2 | 2/2016 | Murillo et al. |
| 9,247,935 B2 | 2/2016 | George et al. |
| 9,314,234 B2 | 4/2016 | Hirotsuka et al. |
| 9,332,980 B2 | 5/2016 | George et al. |
| 9,492,162 B2 | 11/2016 | Murillo et al. |
| 9,700,299 B2 | 7/2017 | Saliman et al. |
| 9,848,868 B2 | 12/2017 | Saliman |
| 9,861,354 B2 | 1/2018 | Saliman et al. |
| 9,913,638 B2 | 3/2018 | Saliman et al. |
| 2001/0041938 A1 | 11/2001 | Hein |
| 2002/0169477 A1 | 11/2002 | Demopulos et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0078617 A1 | 4/2003 | Schwartz et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0117014 A1 | 6/2004 | Bryant |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0043746 A1 | 2/2005 | Pollak et al. |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0178680 A1 | 8/2006 | Beverly et al. |
| 2006/0282098 A1 | 12/2006 | Shelton et al. |
| 2007/0032799 A1 | 2/2007 | Pantages et al. |
| 2007/0038230 A1 | 2/2007 | Stone et al. |
| 2007/0156174 A1 | 7/2007 | Kaiser et al. |
| 2007/0185532 A1 | 8/2007 | Stone et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0140094 A1 | 6/2008 | Schwartz et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0275553 A1 | 11/2008 | Wolf et al. |
| 2008/0294256 A1 | 11/2008 | Hagan et al. |
| 2009/0012520 A1 | 1/2009 | Hixson et al. |
| 2009/0012538 A1 | 1/2009 | Saliman |
| 2009/0018554 A1 | 1/2009 | Thorne et al. |
| 2009/0062816 A1 | 3/2009 | Weber |

(56) References Cited

U.S. PATENT DOCUMENTS

| | | |
|---|---|---|
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0112232 A1 | 4/2009 | Crainich et al. |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0071563 A1 | 3/2011 | Magliani |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1 | 11/2011 | Denham et al. |
| 2012/0101524 A1 | 4/2012 | Bennett |
| 2012/0303046 A1 | 11/2012 | Stone et al. |
| 2013/0072948 A1 | 3/2013 | States, III et al. |
| 2013/0085512 A1 | 4/2013 | Wyman et al. |
| 2013/0253536 A1 | 9/2013 | Harris et al. |
| 2014/0188136 A1 | 7/2014 | Cournoyer et al. |
| 2014/0222034 A1 | 8/2014 | Saliman |
| 2015/0034694 A1 | 2/2015 | Cappola |
| 2015/0073442 A1 | 3/2015 | Saliman et al. |
| 2015/0157317 A1 | 6/2015 | Bagaoisan et al. |
| 2015/0173742 A1 | 6/2015 | Palese et al. |
| 2015/0173743 A1 | 6/2015 | Palese et al. |
| 2015/0209029 A1 | 7/2015 | Hendricken et al. |
| 2015/0257756 A1 | 9/2015 | Sauer |
| 2015/0297215 A1 | 10/2015 | Hendricksen et al. |
| 2015/0313589 A1 | 11/2015 | Hendricksen et al. |
| 2016/0192926 A1 | 7/2016 | Hendricksen et al. |
| 2016/0220244 A1 | 8/2016 | Murillo et al. |
| 2016/0242765 A1 | 8/2016 | George et al. |
| 2016/0302789 A1 | 10/2016 | Hirotsuka et al. |
| 2017/0020512 A1 | 1/2017 | Murillo et al. |
| 2017/0027558 A1 | 2/2017 | Murillo et al. |
| 2017/0119372 A1 | 5/2017 | Peter et al. |
| 2018/0125479 A1 | 5/2018 | Saliman et al. |

FOREIGN PATENT DOCUMENTS

| | | |
|---|---|---|
| CN | 103298503 A | 9/2013 |
| CN | 103717149 A | 4/2014 |
| EP | 0647431 A2 | 4/1995 |
| EP | 2030575 A1 | 3/2009 |
| EP | 2184015 A2 | 5/2010 |
| EP | 2081481 B1 | 11/2015 |
| JP | 3032847 U | 3/1991 |
| SU | 376089 A | 4/1973 |
| SU | 728848 A1 | 4/1980 |
| SU | 1725847 A1 | 4/1992 |
| WO | WO 92/05828 A1 | 4/1992 |
| WO | WO 95/13021 A1 | 5/1995 |
| WO | WO98/11825 A1 | 3/1998 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO 02/07607 A1 | 1/2002 |
| WO | WO 02/096296 A1 | 12/2002 |
| WO | WO 03/077771 A1 | 9/2003 |
| WO | WO 2006/001040 A1 | 1/2006 |
| WO | WO 2006/040562 A1 | 4/2006 |
| WO | WO 2010/141695 A1 | 12/2010 |
| WO | WO 2011/057245 A2 | 5/2011 |

OTHER PUBLICATIONS

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05 &p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Ceterix; Novocut suture manager; retrieved from the internet (https://web.archive.org/web/20150314071511/http://www.ceterix.com:80/im-a-physician/products/) on Oct. 11, 2017; 1 page; Mar. 12, 2015.

Ceterix; Novocut suture manager; retrieved from the internet (https://www.youtube.com/watch?v=6txqBJxvnuA) on Oct. 11, 2017; 1 page; Mar. 5, 2015.

Covidien Surgical; Endo Stitch 10 mm Suturing Device; accessed Dec. 4, 2012 at <http://www.autosuture.com/autosuture/pagebuilder. aspx?topicID=7407&breadcrumbs=0:63659,30691:0,309:0> 2 pgs.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

dictionary.com; Adjacent (definition); 5 pgs.; retrieved from the internet (http://www.dictionary.com/browse/adjacent) on Apr. 5, 2016.

Duerig, T. et al., "An overview of nitinol medical applications" Materials Science and Engineering A273-275, pp. 149-160; May 1999.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

Medsfera; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Nord et al.; Posterior lateral meniscal root tears and meniscal repair; Orthopedics Today; 5 pgs; Nov. 2010; retrieved from the internet on

(56) References Cited

OTHER PUBLICATIONS

Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).
Rimmer et al.; Failure Strength of Different Meniscal Suturing Techniques; Arthroscopy: The Journal of Arthroscopic and Related Surgery; vol. 11; No. 2; pp. 146-150; Apr. 1995.
Schneeberger, et al; "Mechanical Strength of Arthroscopic Rotator Cuff Repair Techniques: An in Vitro Study," J Bone Joint Surg Am., Dec. 2002; 84:2152-2160.
Smith&Nephew; Fast-Fix Meniscal Repair System (product webpage); 4 pgs.; downloaded Nov. 21, 2011 (http://endo.smith-nephew.com/fr/node.asp?NodeId=3562).
Strobel; Manual of Arthroscopic Surgery (1st Edition); Springer Verlag, Hiedelberg © 2002; pp. 127-129; Dec. 15, 2001.
USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.
USS SportsMedicine ArthroSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

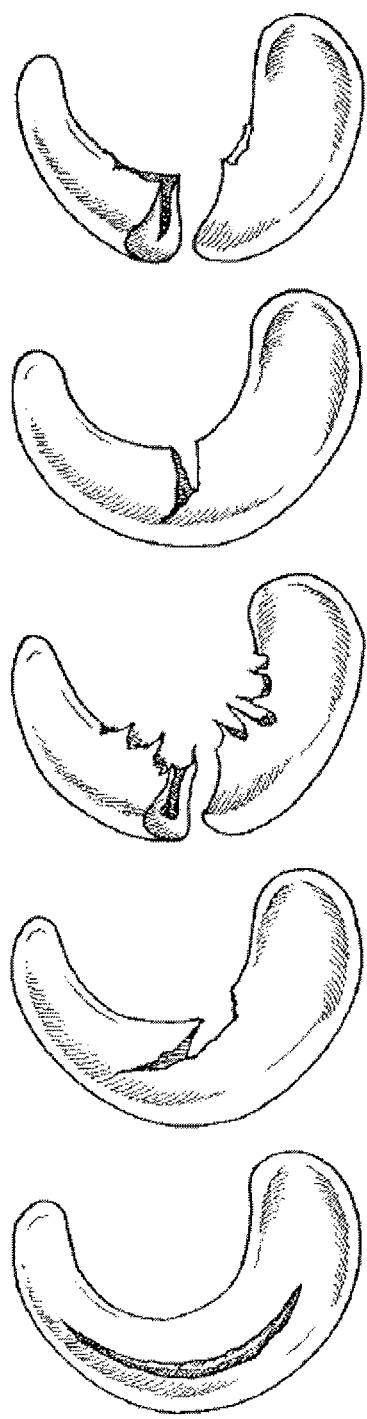
FIG. 4A Vertical longitudinal
FIG. 4B Oblique
FIG. 4C Degenerative
FIG. 4D Transverse (Radial)
FIG. 4E Horizontal
FIG. 4F Root tear

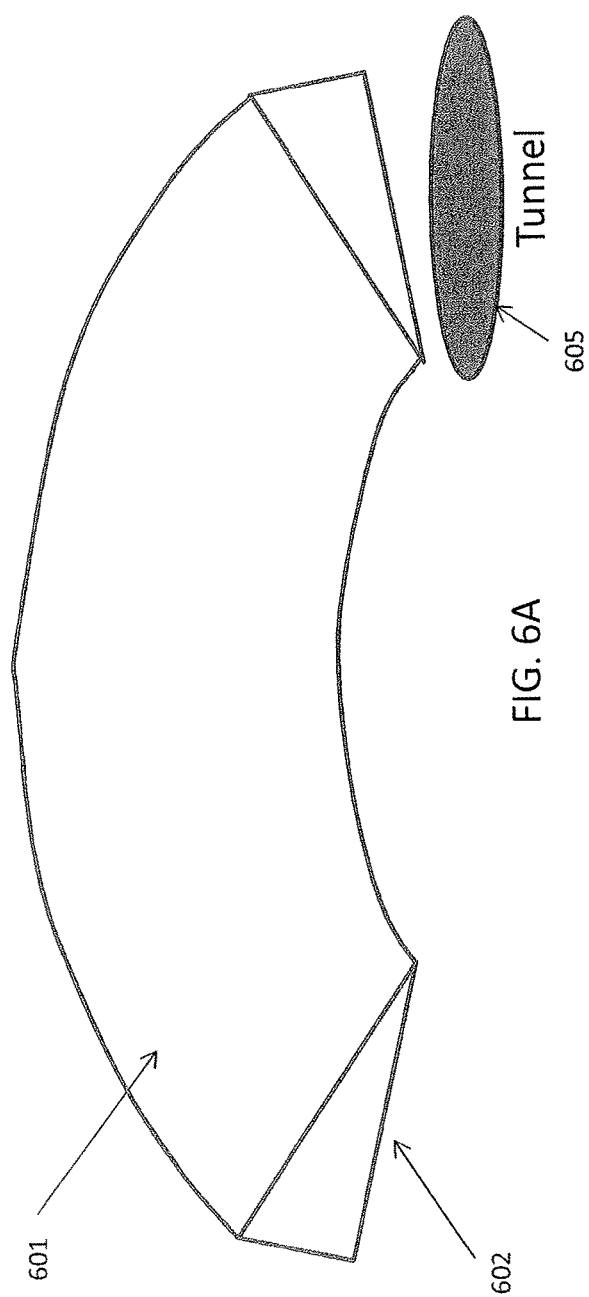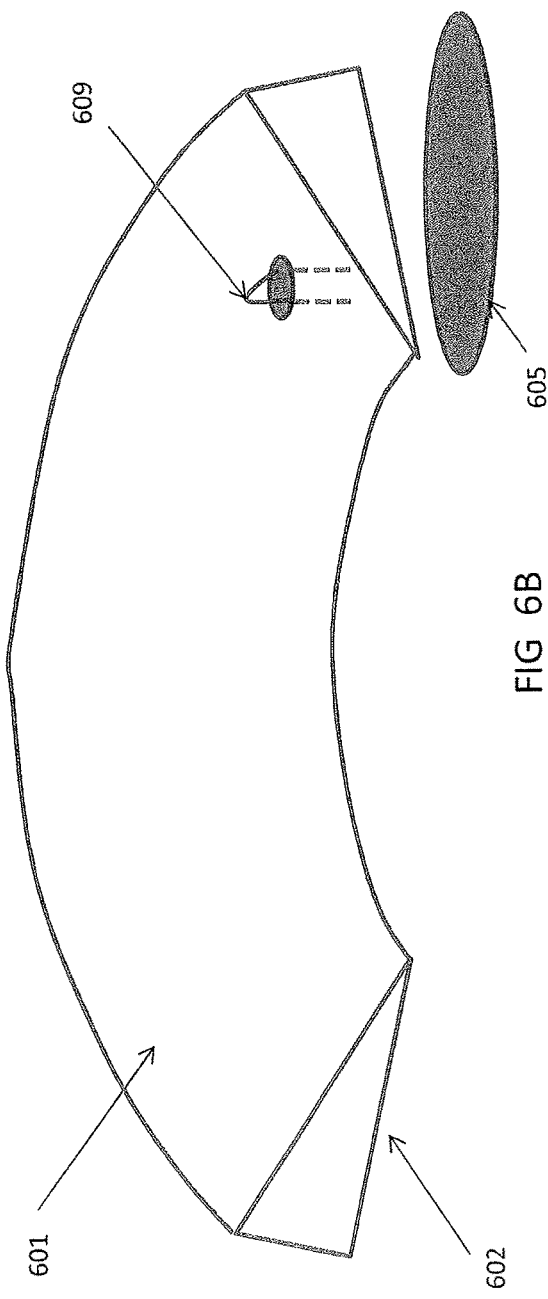

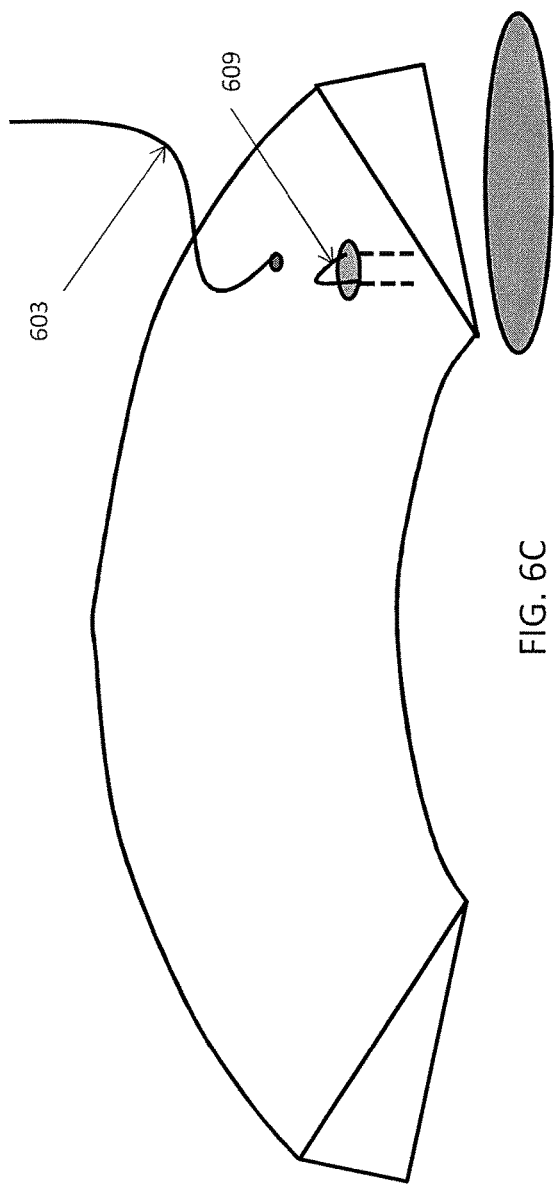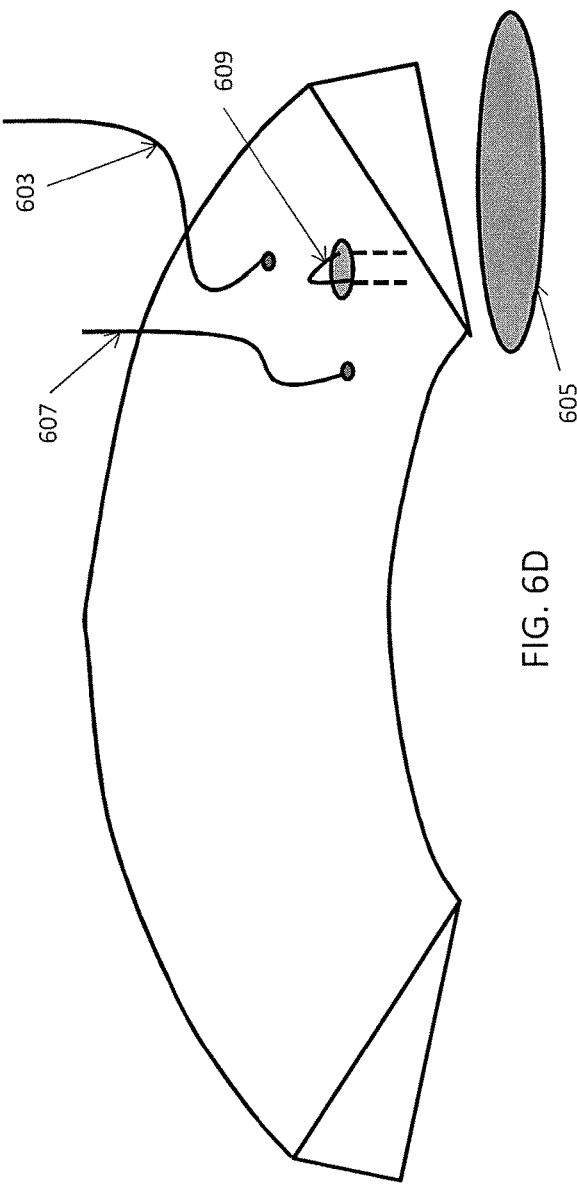

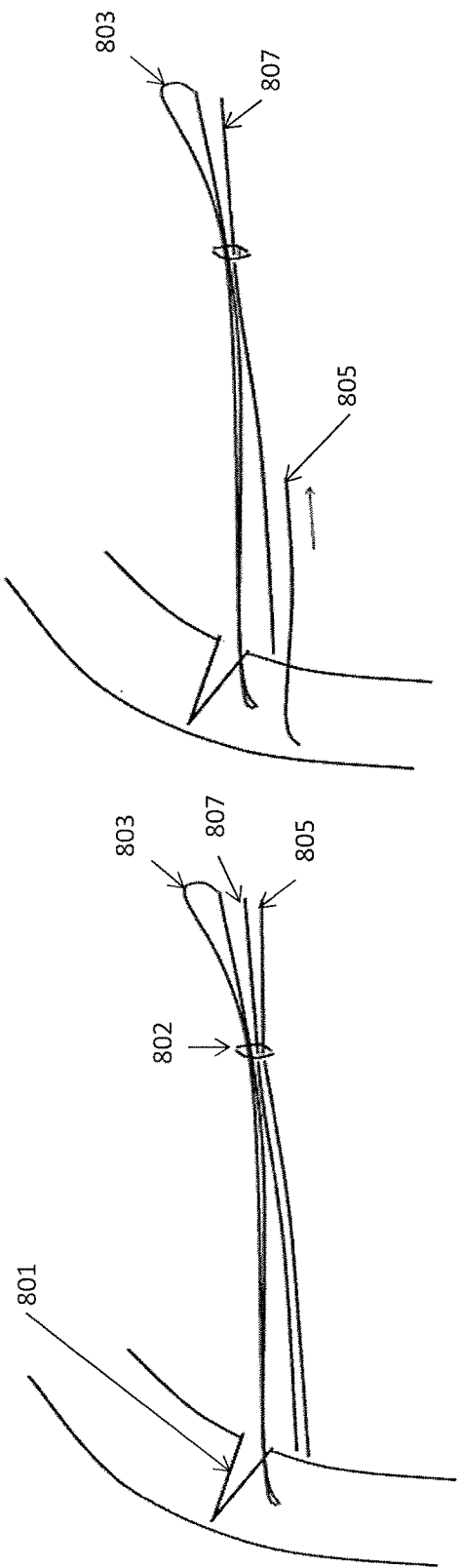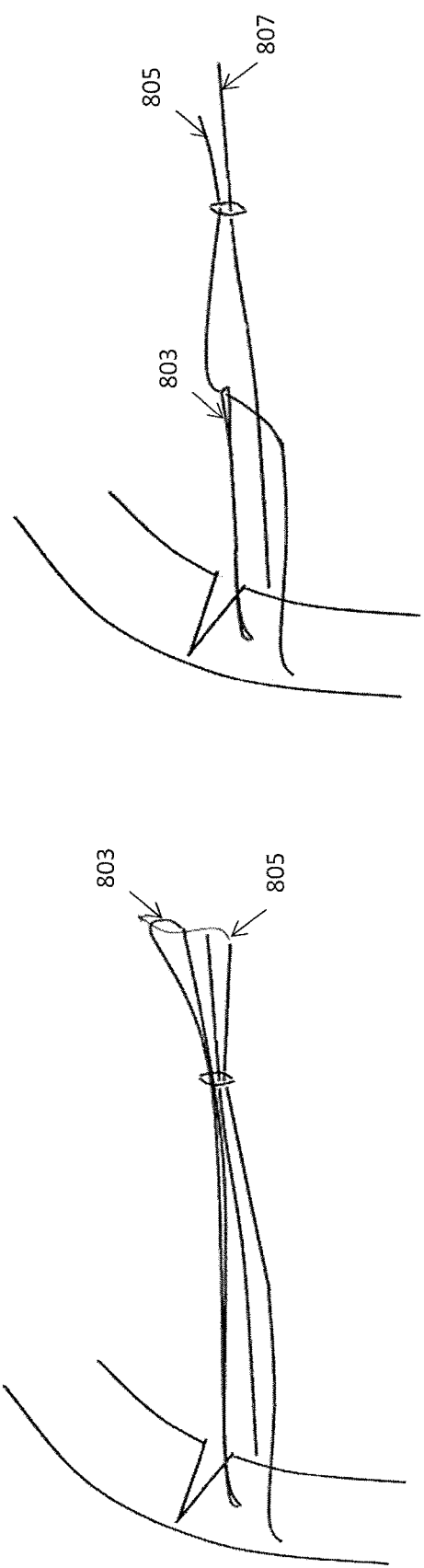

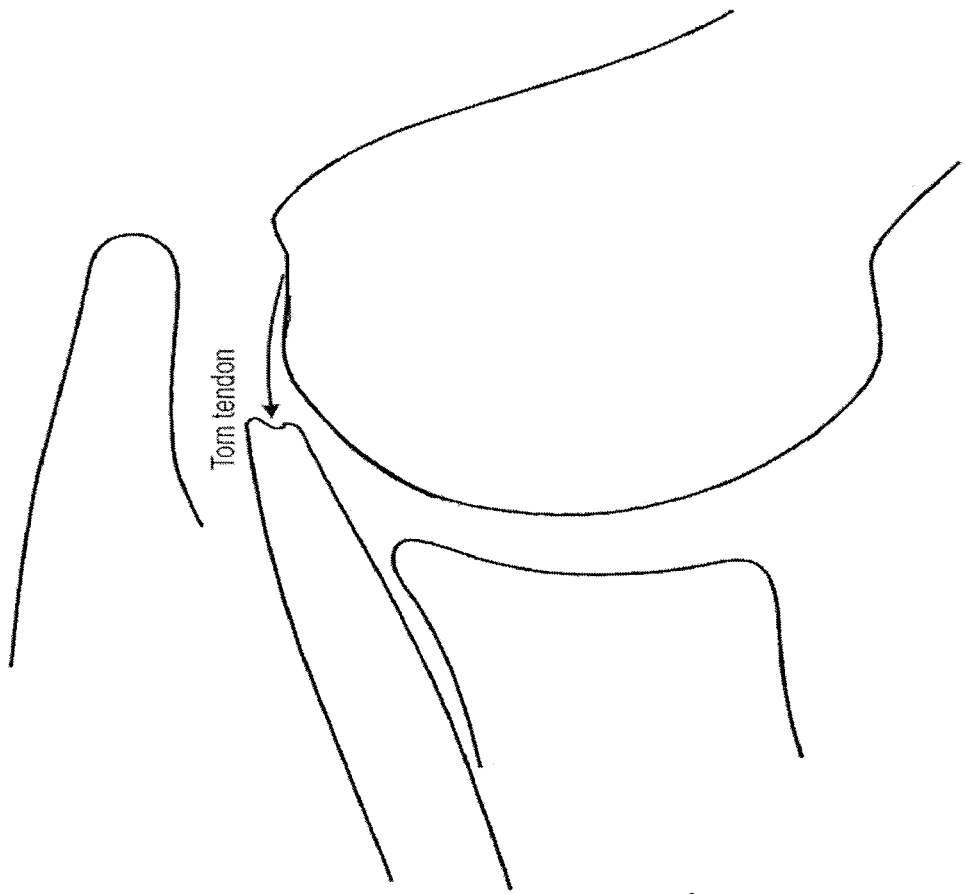
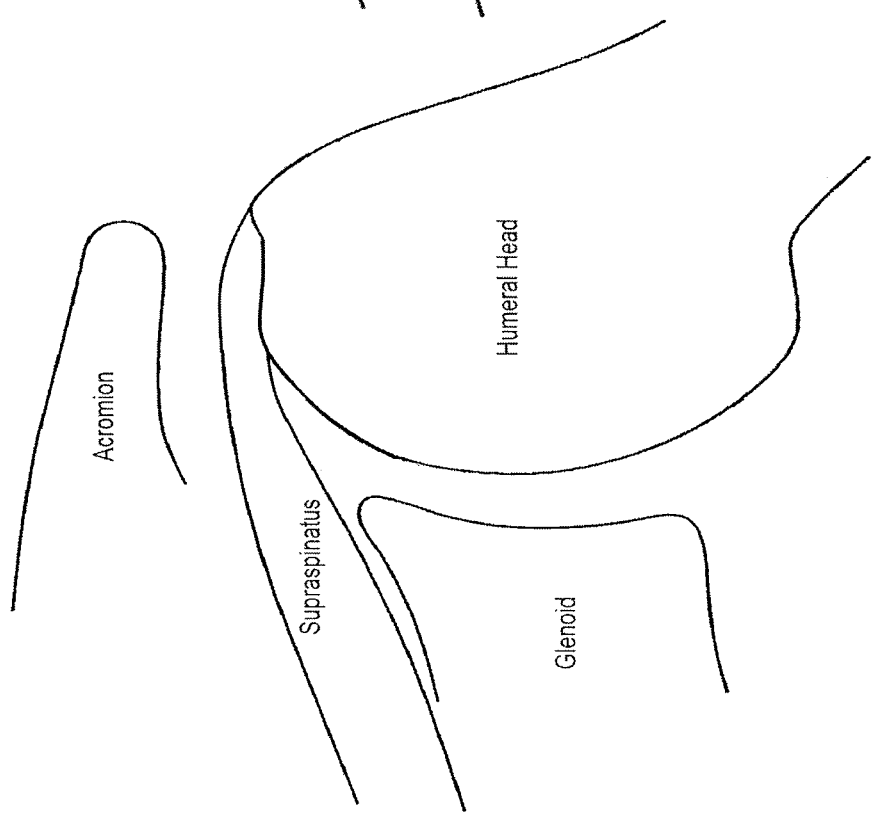
FIG. 10B
FIG. 10A

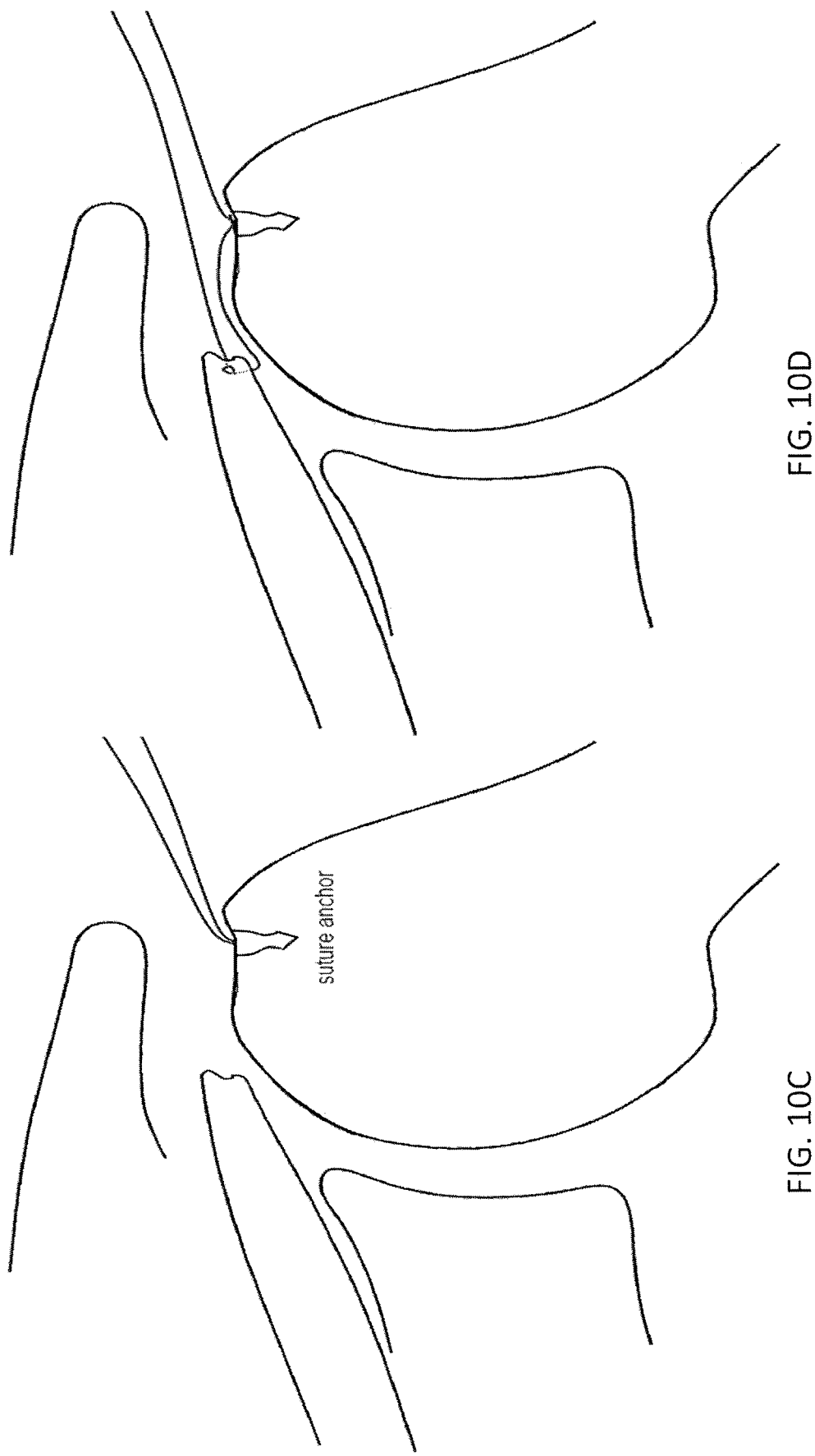

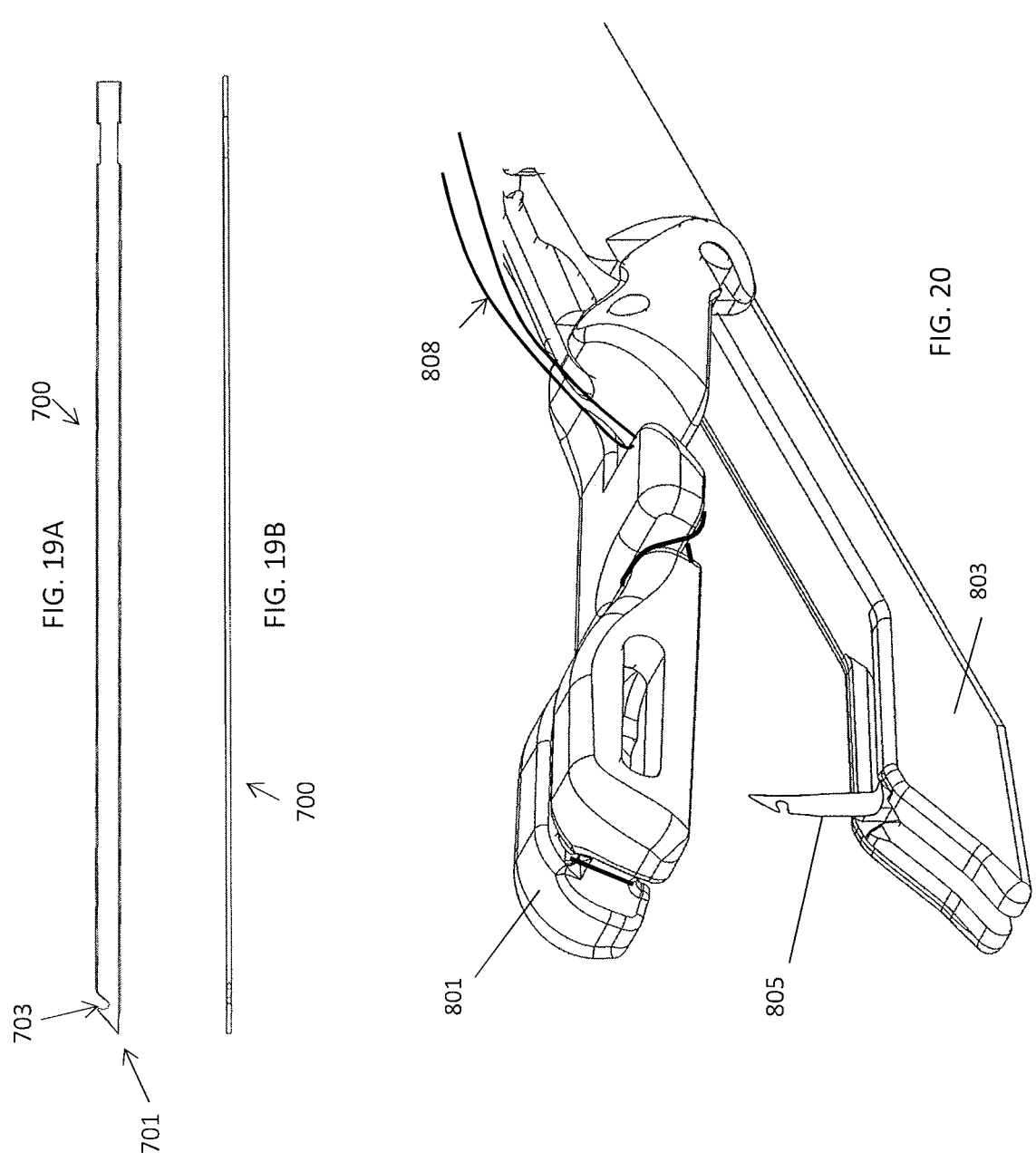

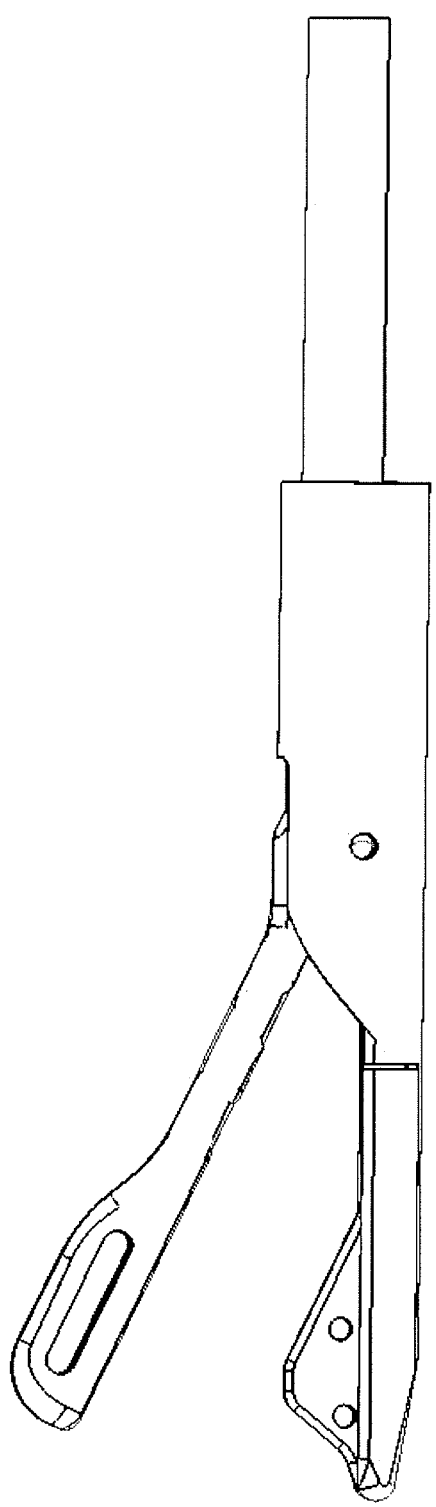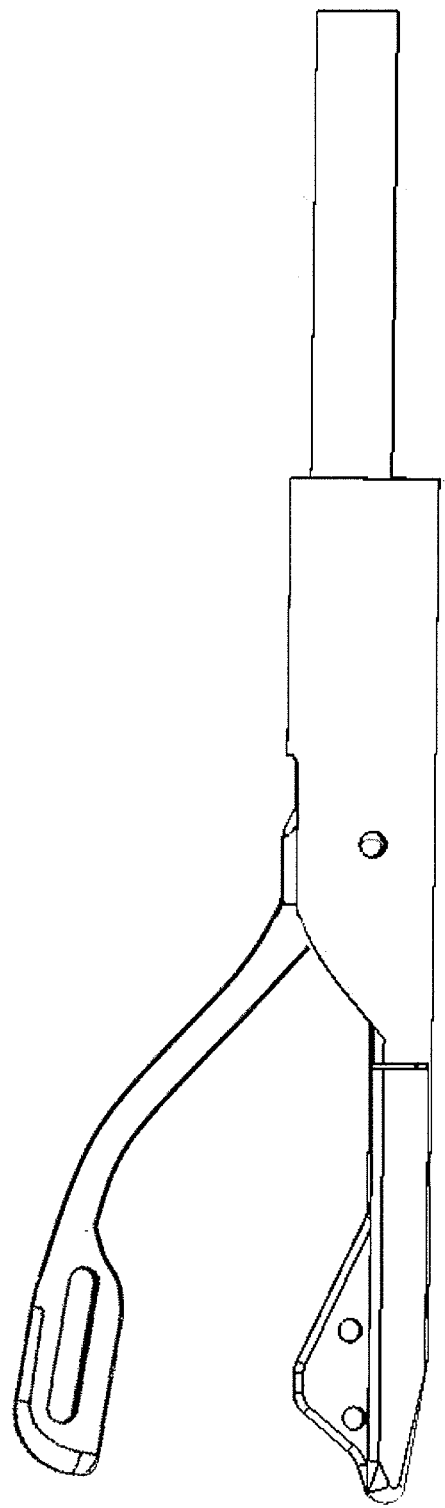
FIG. 22A
FIG. 22B

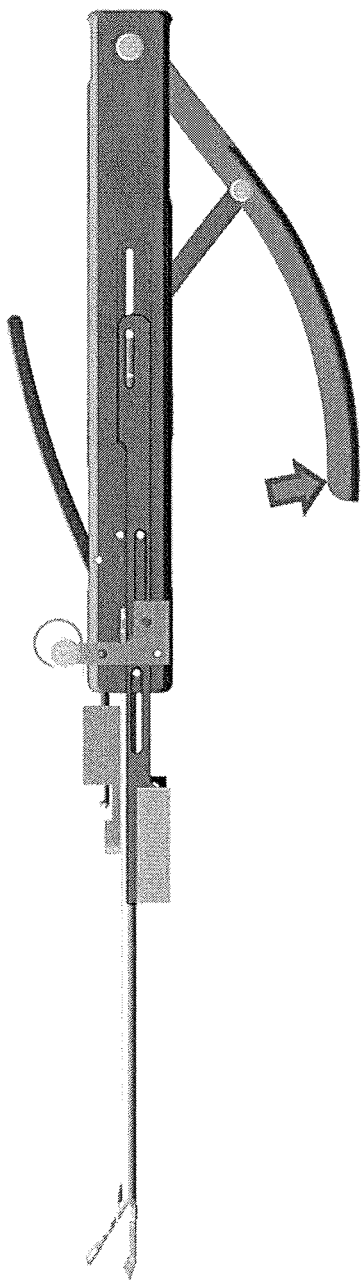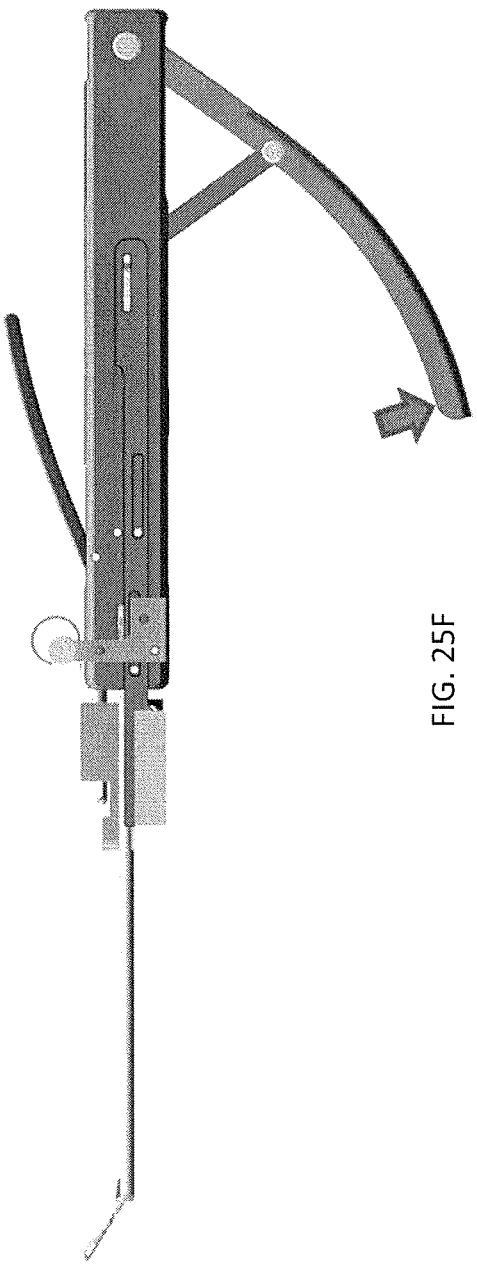
FIG. 25E
FIG. 25F

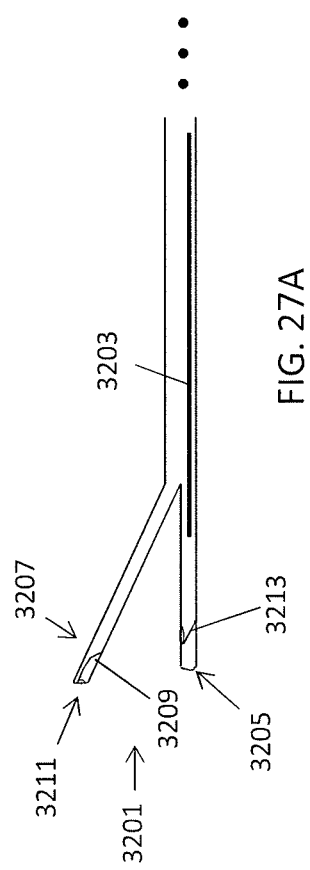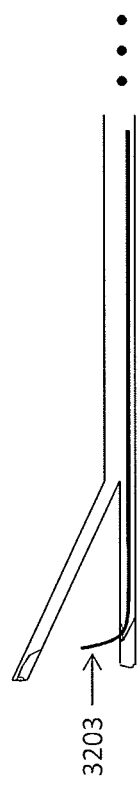

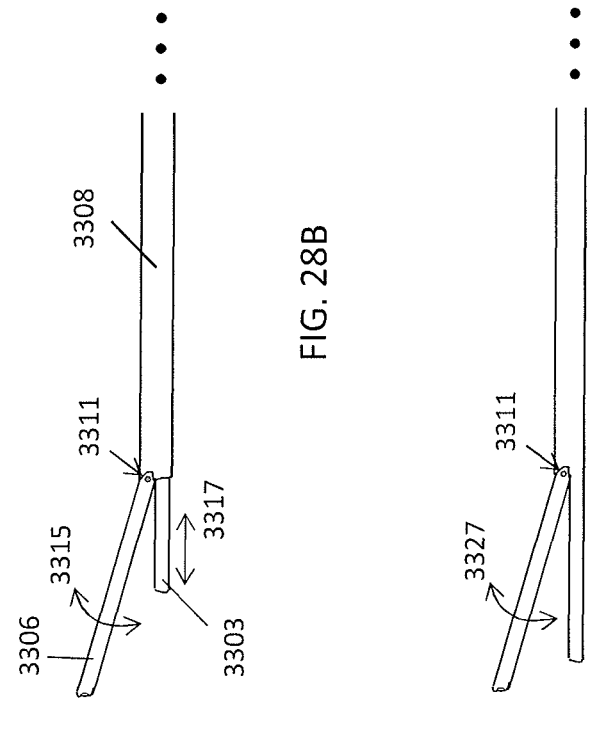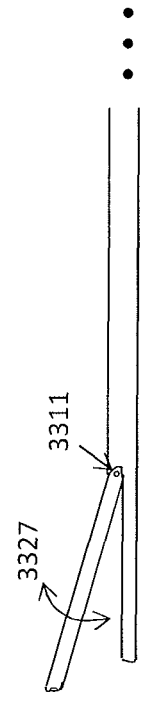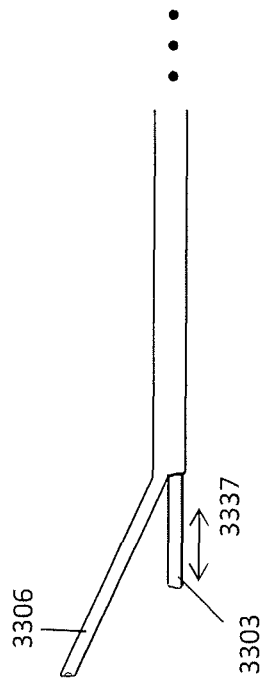
FIG. 28A  FIG. 28B  FIG. 28C  FIG. 28D
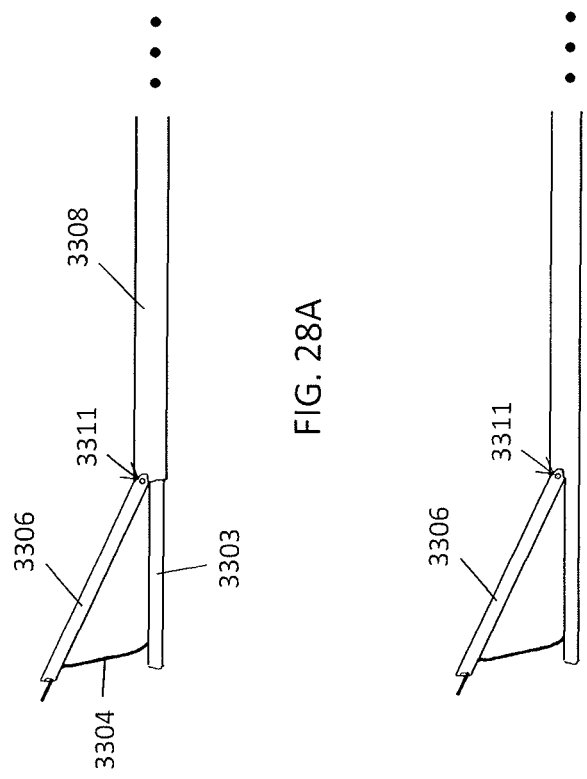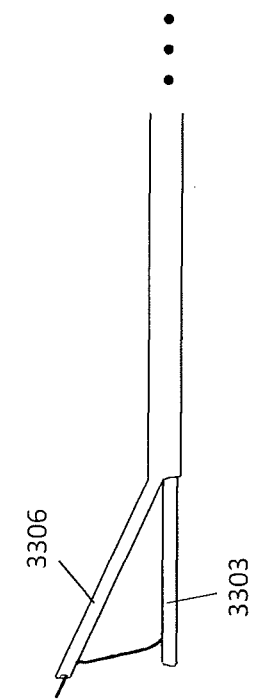
FIG. 28E  FIG. 28F

3505

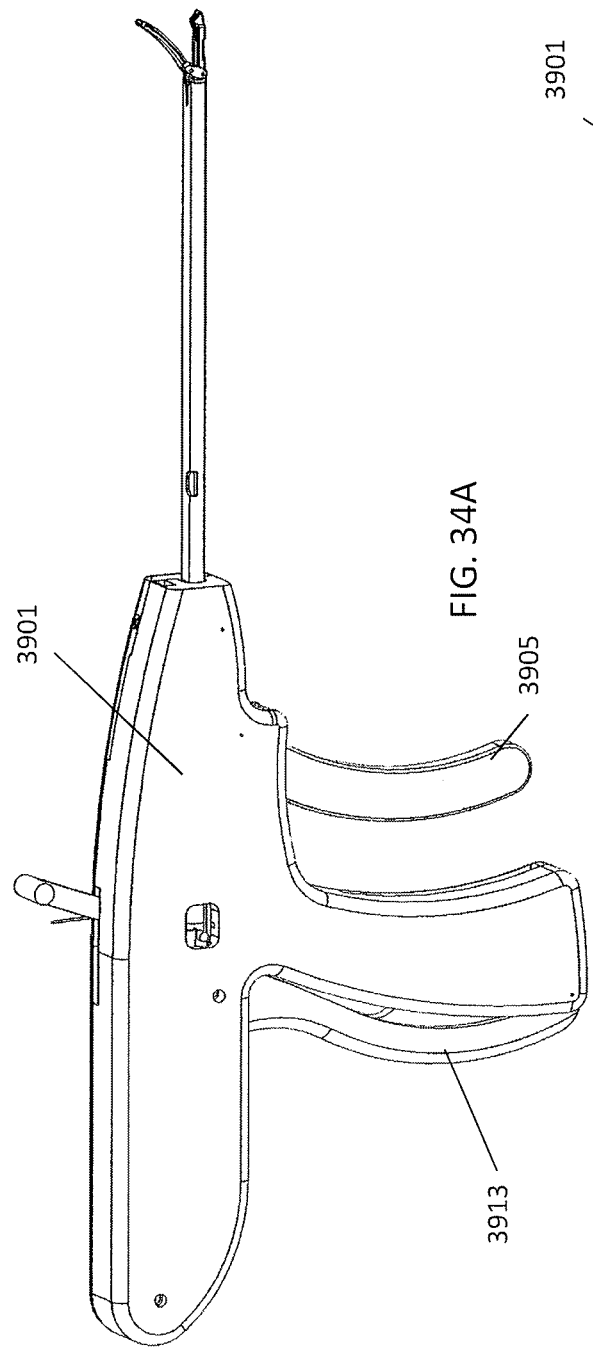
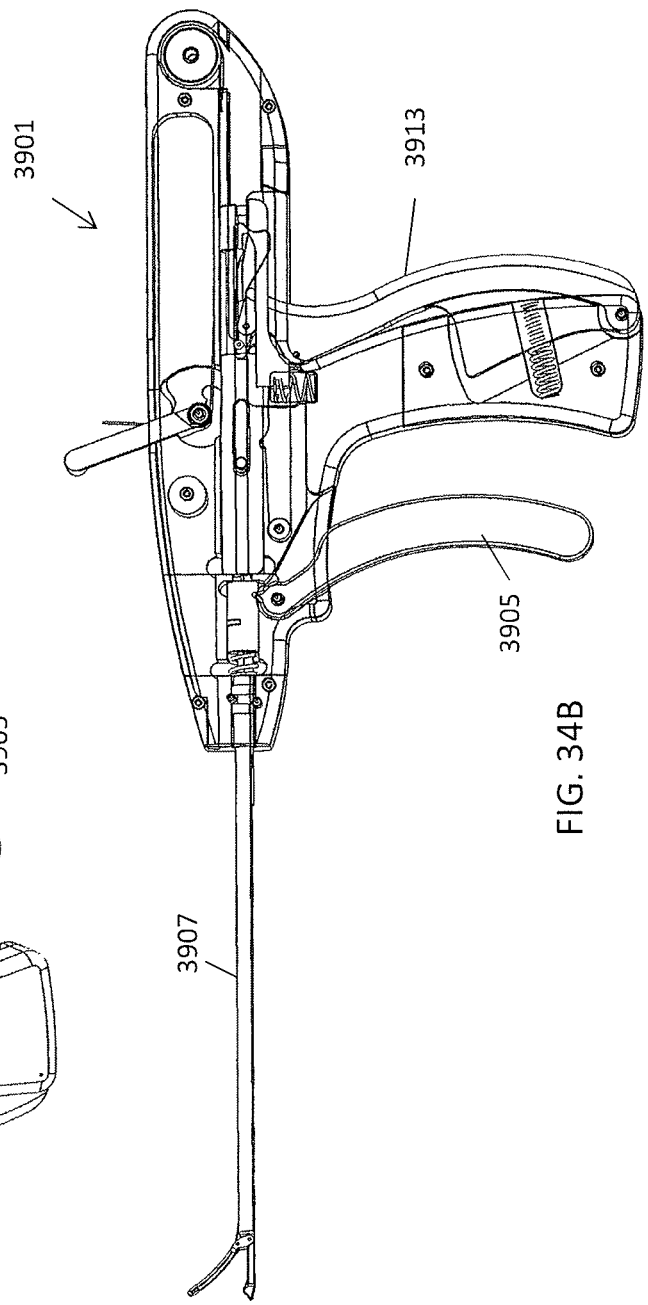
FIG. 34A
FIG. 34B

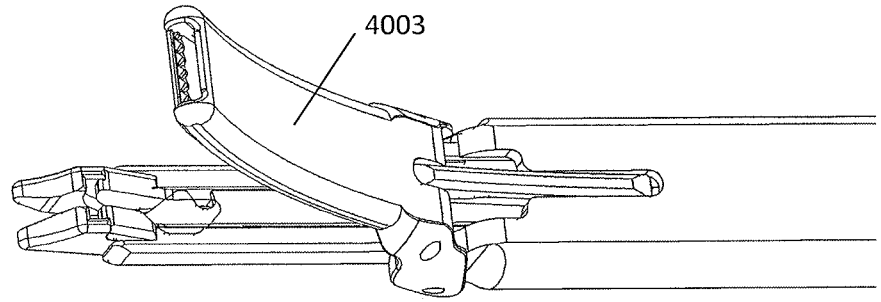
FIG. 35A
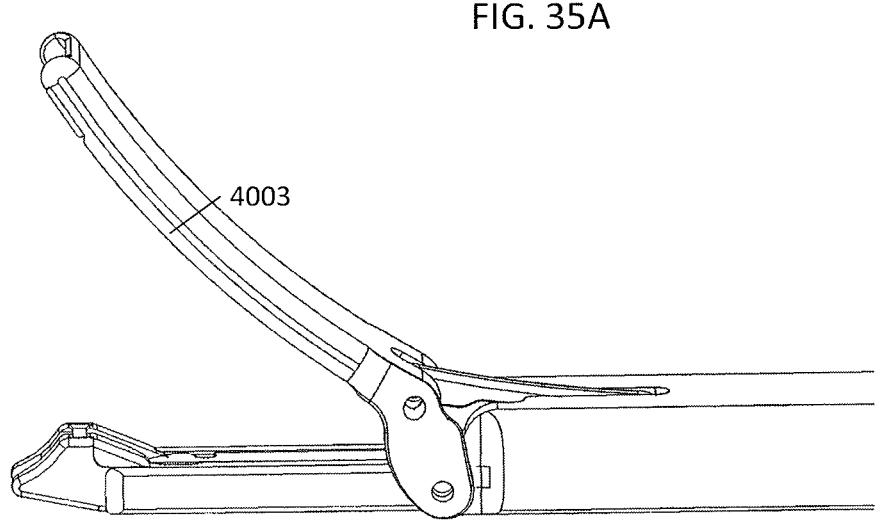
FIG. 35B
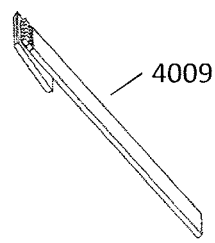
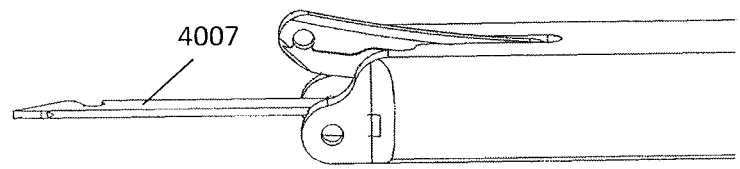
FIG. 35C

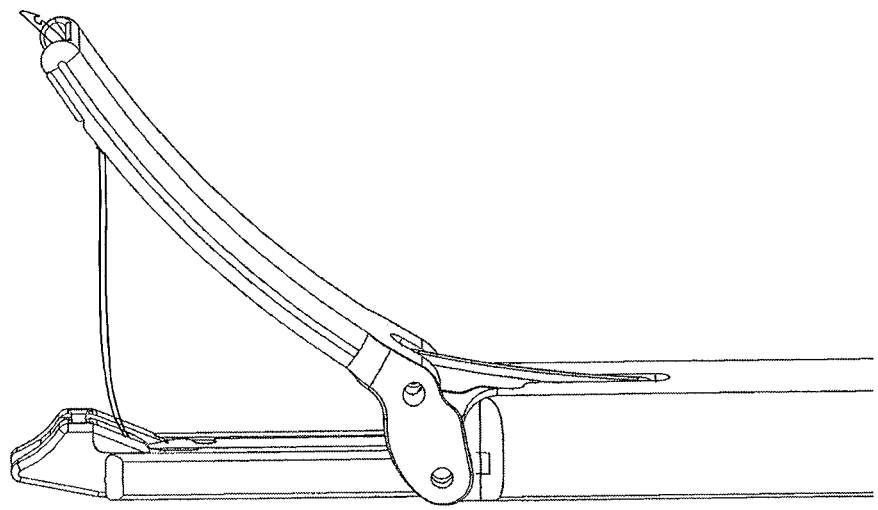
FIG. 35D
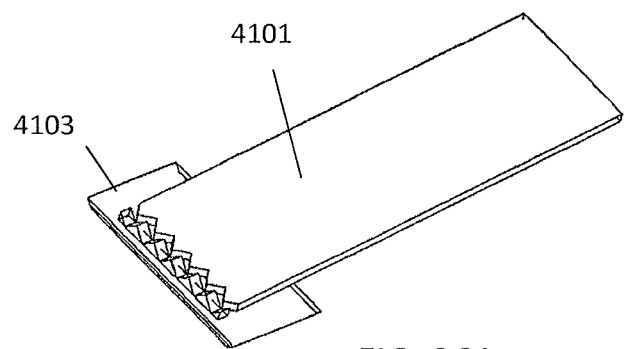
FIG. 36A
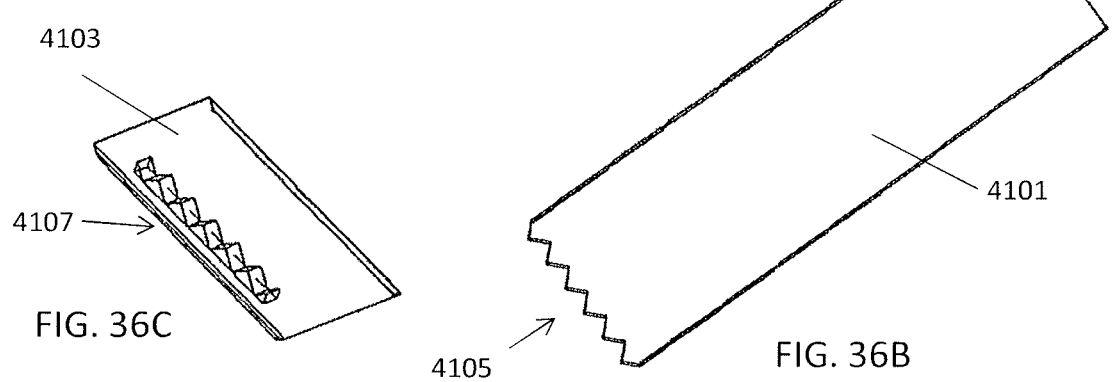
FIG. 36C
FIG. 36B

SUTURE METHODS FOR FORMING LOCKING LOOPS STITCHES

CROSS REFERENCE TO RELATED APPLICATIONS

This application is a continuation of U.S. patent application Ser. No. 14/292,695, filed May 30, 2014, titled "SUTURE METHODS FOR FORMING LOCKING LOOPS STITCHES," now U.S. Pat. No. 9,848,868, which claims priority as a continuation-in-part of U.S. patent application Ser. No. 13/893,209, filed May 13, 2013, titled "IMPLANT AND METHOD FOR REPAIR OF THE ANTERIOR CRUCIATE LIGAMENT," now U.S. Pat. No. 8,888,848, which is a continuation of U.S. patent application Ser. No. 13/347,184, filed Jan. 10, 2012, titled "IMPLANT AND METHOD FOR REPAIR OF THE ANTERIOR CRUCIATE LIGAMENT," now U.S. Pat. No. 8,500,809, which claims priority to U.S. Provisional Patent Application No. 61/431,293, filed Jan. 10, 2011, titled "IMPLANT AND METHOD FOR REPAIR OF THE ANTERIOR CRUCIATE LIGAMENT."

U.S. patent application Ser. No. 14/292,695 also claims the benefit of U.S. Provisional Patent Application No. 61/829,169, filed May 30, 2013, titled "SUTURE PASSER DEVICES AND METHODS."

All of these patents and patent applications are herein incorporated by reference in their entirety.

INCORPORATION BY REFERENCE

Field

The methods, devices and systems described herein may be used to suture tissue, particularly in difficult to access regions. In particular, described herein are suture methods and suture passers for performing them.

Background

Suturing of tissue during surgical procedures is time consuming and can be particularly challenging in difficult to access body regions and regions that have limited clearance, such as regions partially surrounded or partially covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

For example, some variations of suture passers, such as those described in U.S. Pat. No. 7,377,926 to Taylor, have opposing jaws that open and close over tissue. One, or in some variations, both, jaws open, scissor-like, so that tissue may be inserted between the open jaws. Unfortunately, such devices cannot be adequately positioned for use in hard to navigate body regions such as the joints of the body, including the knee (e.g., meniscus) and the shoulder.

A non-exhaustive list of difficult to access, and therefore difficult to properly repair, tissues includes the meniscus of the knee, the tendons and ligaments of the shoulder (e.g., rotator cuff), and non-bony spinal tissues (including the disc annulus). Any such structures may benefit from the devices and methods described herein. For example, the meniscus is a C-shaped piece of fibrocartilage which is located at the peripheral aspect of the joint (e.g., the knee) between the condyles of the femur and the tibia on the lateral and medial sides of the knee. The central two-thirds of the meniscus has a limited blood supply while the peripheral one third typically has an excellent blood supply. Acute traumatic events commonly cause meniscus tears in younger patients while degenerative tears are more common in older patients as the menisci become increasingly brittle with age. Typically, when the meniscus is damaged, a torn piece of meniscus may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult to perform because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for visualization of the structures within that joint. Then, using miniature instruments which may be as small as ¹⁄₁₀ of an inch, the structures are examined and the surgery is performed.

FIGS. 1A, 1B and 2 illustrate the anatomy of the meniscus in the context of a knee joint. As shown in FIG. 2 the capsule region (the outer edge region of the meniscus) is vascularized. Blood enters the meniscus from the menisculocapsular region 211 lateral to the meniscus. A typical meniscus has a flattened bottom (inferior surface or side) and a concave top (superior surface or side), and the outer cross-sectional shape is somewhat triangular. The outer edge of the meniscus transitions into the capsule. FIG. 3 illustrates the various fibers forming a meniscus. As illustrated in FIG. 3, there are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed.

For example, FIGS. 4A-4F illustrate various tear patterns or injuries to a meniscus. Tears may be vertical/longitudinal (FIG. 4A), oblique (FIG. 4B), degenerative (FIG. 4C), including radially degenerative, transverse or radial (FIG. 4D) and horizontal (FIG. 4E). Most prior art devices for suturing or repairing the meniscus are only capable of reliably repairing vertical/longitudinal tears. Such devices are not typically useful for repairing radial or horizontal tears. Furthermore, prior art device mechanisms have a high inherent risk for iatrogenic injury to surrounding neurovascular structures and chondral surfaces.

Thus, there is a need for methods, devices and systems for suturing tissue, particularly tissue in difficult to access regions of the body including the joints (shoulder, knee, etc.). In particularly, it has proven useful to provide a device that may simply and reliably reach and pass sutures within otherwise inaccessible tissue regions. Finally, it is useful to provide a suturing device that allows the tissue to be sutured to be held within an adjustable jaw so that it can be predictably sutured, and done so in a manner that protects fragile surrounding tissues from iatrogenic injury. The methods, devices and systems described herein may address this need.

SUMMARY OF THE DISCLOSURE

The present invention relates to devices, systems and methods for suturing tissue, including a torn meniscus. In general, described herein are methods for repairing tissue using a suture passer to form a locking loop suture pattern to repair the tissue. In particular, described herein are methods of arthroscopically repairing difficult to access tissues such as the meniscus (including a torn meniscal root), the ACL and the rotator cuff by forming one or more locking loops of suture.

In some variations, the suture passers described herein may be configured so that a tissue penetrating element (tissue penetrator, needle, etc.) is configured to travel in an approximately sigmoidal pathway when passing a suture. For example, the suture passer may be configured so that the tissue penetrator extends first distally within a first jaw member of the suture passer, then deflects from this distal direction to travel nearly perpendicular to the distal direction and across the mouth of the suture passer (and through a tissue held in the mouth of the suture passer); the tissue penetrator is then deflected to continue to extend distally within a second jaw member and eventually extend out of a distal opening in the second jaw member.

Because of their independent and dual jaw movement in both angular, allowing angular motion of one jaw and lateral (in-out) motion of the opposite jaw, and particularly with a dual-deflected tissue penetrator (needle), the suture passers described herein may readily access and be positioned around tissue to be sutured in ways not possible with more traditional suture passers. Generally these suture passers may be positioned within the tissue by adjusting the angle of the first jaw member to help avoid non-target tissue as the device is advanced so that the first jaw member is adjacent to the target tissue. The second jaw member may then be extended distally from the proximal position (e.g., by sliding axially, by swinging distally, etc.) so that the tissue is held between the first and second jaw members in a distal-facing jaw opening. The tissue to be sutured may then be clamped securely between the first and second jaw members (e.g., by adjusting the angle of the first jaw member), and a loop (e.g., "bight") of suture may be passed between the two by extending a tissue penetrator from within one of the first or second jaw members, across the opening and through the tissue, to either drop off or pick up a suture at the opposite jaw member. The tissue penetrator can then be retracted back into the jaw member that houses it.

For example, described herein are methods of arthroscopically repairing a knee tissue with a length of suture having a distal limb region, a proximal limb region and a central loop region there between. Knee tissue may be the meniscus (e.g., a torn meniscus, the root of the meniscus, etc.), a knee ligament (e.g., the ACL, etc.) or the like. Non-knee tissues may also be repaired as described herein. For example, the method may include: arthroscopically passing a first loop of the loop region of the suture through the tissue with a suture passer, from a first side of the tissue to a second side of the tissue; moving the distal limb region of the suture from the first side of the tissue to the second side of the tissue; moving the distal limb region though the first loop; and cinching the first loop region closed.

The method may also include forming a passage through bone to anchor the distal and/or proximal end regions of the suture. For example, the method may include forming a passage through either the tibia or the femur; and pulling the first and second limb regions through the passage after cinching the first loop region closed.

As mentioned, the tissue may be meniscus. For example arthroscopically passing the first loop may comprise passing the first loop of the loop region of the suture from an inferior to a superior surface of a meniscus with the suture passer. In some variations, the tissue is anterior cruciate ligament (ACL). For example, arthroscopically passing the first loop may comprise passing the first loop of the loop region of the suture from a first side of an anterior cruciate ligament to a second side of the anterior cruciate ligament.

In any of these methods, the procedure may include positioning the suture passer device around the target tissue as described in greater detail below, including any of the associated steps relevant to this positioning. For example, the method may include arthroscopically positioning the suture passer with a first jaw on one side of the tissue and a second jaw on an opposite side of the tissue.

Arthroscopically positioning the suture passer with a first jaw between a superior surface of a meniscus and a femur and a second jaw between the inferior surface and a tibia.

In general, the distal and proximal limbs may be passed through the tissue, like the loop region, using the suture passer. For example, the proximal or distal limb region of the suture may be moved from one region of the tissue to another by passing the distal limb region of the suture with the suture passer through the tissue. Alternatively, the distal ends of the suture may be moved without passing through the tissue, e.g., around the tissue. For example, a method may also include moving the proximal limb region of the suture from the first side of the tissue to the second side of the tissue; the method may also include moving the proximal limb region though the first loop.

Arthroscopically passing the first loop may be performed before moving the distal limb region of the suture from the first side of the tissue to the second side of the tissue.

A method of arthroscopically repairing a knee tissue with a length of suture having a distal limb region, a proximal limb region and a central loop region there between, may include: passing a first loop of the loop region of the suture from an inferior to a superior surface of a meniscus with a suture passer; passing the distal limb region of the suture from the inferior to the superior surface of the meniscus with the suture passer; passing the distal limb region though the first loop; and cinching the first loop region closed.

As mentioned, the methods may also include passing the proximal limb region of the suture from the inferior to the superior surface of the meniscus with the suture passer, and/or passing the proximal limb region though the first loop. Passing the first loop may be performed before passing the distal limb region of the suture from the inferior to the superior surface of the meniscus with the suture passer.

Passing the distal limb region of the suture from the inferior to the superior surface of the meniscus with the suture passer may be performed before passing the first loop.

The methods may be performed primarily or entirely arthroscopically, including arthroscopically positioning the suture passer with a first jaw between the superior surface of the meniscus and the femur and a second jaw between the inferior surface and the tibia.

For example, a method of arthroscopically repairing a knee tissue with a length of suture having a distal limb region, a proximal limb region and a central loop region there between, may include: passing a first loop of the loop region of the suture from an inferior to a superior surface of a meniscus with a suture passer; passing the proximal limb region of the suture from the inferior to the superior surface of the meniscus with the suture passer; passing the distal limb region of the suture from the inferior to the superior surface of the meniscus with the suture passer; passing the distal limb region though the first loop; and cinching the first loop region closed.

Any of these methods for repairing the meniscus may include anchoring the distal limb region and the proximal limb region to the tibia, including securing to a channel or anchoring. For example, the method may include forming a channel in the tibia to anchor the suture.

Any of the methods may include passing a second loop of the loop region of the suture from an inferior to a superior surface of the meniscus with the suture passer; and passing the proximal limb region through the second loop; and cinching the second loop region closed.

Also described herein are methods of arthroscopically repairing a knee tissue with a length of suture having a distal limb region, a proximal limb region and a central loop region there between, the method comprising: passing a first loop of the loop region of suture from an inferior to a superior surface of a meniscus having a radially tear using a suture passer, so that the first loop is on a first side of the radial tear; passing the distal limb region of the suture from the inferior to the superior surface of the meniscus using the suture passer, so that the distal limb region is on the first side of the radial tear; passing the distal limb region though the first loop; cinching the first loop region closed; passing a second loop of the loop region of suture from the inferior to the superior surface of the meniscus using the suture passer, so that the second loop is on a second side of the radial tear; passing the proximal limb region of the suture from the inferior to the superior surface of the meniscus using the suture passer, so that the proximal limb region is on the second side of the radial tear; cinching the second loop region closed; and knotting the proximal limb region and the distal limb region of the suture together to close the radial tear.

Also described are methods of repairing a tissue by arthroscopically forming a locking loop of suture through the tissue, the suture formed of a length of suture material having a distal limb region, a proximal limb region and a central loop region there between, the method comprising: passing a loop of the central loop region of the suture from a first side of the tissue to a second side of the tissue; passing the a distal limb region through the tissue from the first side to the second side of the tissue; passing the distal limb region through the loop; and cinching the loop over the distal limb.

Also described are methods of repairing a knee tissue by arthroscopically forming a locking loop of suture through the ACL, the suture formed of a length of suture material having a distal limb region, a proximal limb region and a central loop region there between, the method comprising: passing a loop of the central loop region of the suture from a first side of a torn Anterior Cruciate Ligament (ACL) to a second side of the ACL; passing the a distal limb region through the ACL from the first side to the second side of the ACL; passing the proximal limb region through the ACL from the first side to the second side of the ACL; passing the distal and proximal limb regions through the loop; and cinching the loop over the distal and proximal limbs.

Also described are methods of repairing a torn rotator cuff by arthroscopically forming a locking loop of suture through the supraspinus tendon, the suture formed of a length of suture material having a distal limb region, a proximal limb region and a central loop region there between, the method comprising: passing a loop of the central loop region of the suture from a first side of the supraspinus tendon to a second side of the supraspinus tendon; passing the a distal limb region through the supraspinus tendon to the second side of the supraspinus tendon; passing the proximal limb region through the supraspinus tendon to the second side of the supraspinus tendon; passing the distal and proximal limb regions through the loop; and cinching the loop over the distal and proximal limbs.

BRIEF DESCRIPTION OF THE DRAWINGS

FIGS. 4A-4F illustrate various tear patterns that may be repaired as described herein.

FIGS. 6A-6E show another variation of a meniscal root repair.

FIGS. 8A-8J illustrate one variation of a method to repair radial tears in a meniscus using a locking loop suture pattern as described herein.

FIGS. 10A-10H illustrate one variation of a method to repair a torn rotator cuff using a locking loop suture pattern formed by a suture passer.

FIG. 19A shows a side view of one variation of a tissue penetrator.

FIG. 19B shows a side perspective view of the tissue penetrator of FIG. 19A.

FIG. 20 shows the perspective view of FIG. 16 with a tissue penetrator partially extended between the first and second jaw members, and with a suture loaded in the first jaw member.

FIG. 22A shows a side view of one variation of the distal end region of a suture passer, showing a first and second jaw member extended in to form a distal facing opening.

FIG. 22B shows another variation of the distal end region of a suture passer with the first and second jaw member extended in to form a distal facing opening.

FIGS. 25A-25F illustrate operation of one variation of dual deployment suture passer.

FIGS. 27A-27C illustrate a generic variation of a suture passer including a tissue penetrator traveling in a sigmoidal path in which the distal end of the tissue penetrator extends distally from the upper jaw.

FIG. 28A is another variation of a suture passer having a tissue penetrator that extends distally from the upper jaw; FIG. 28B illustrates the motion of the upper and lower jaw of the suture passer of FIG. 28A.

FIG. 28C is another variation of a suture passer having a tissue penetrator that extends distally from the upper jaw; FIG. 28D illustrates the motion of the upper jaw of the suture passer of FIG. 28C.

FIG. 28E is another variation of a suture passer having a tissue penetrator that extends distally from the upper jaw; FIG. 28F illustrates the motion of the lower jaw of the suture passer of FIG. 28A.

FIGS. 34A-34C show another variation of a suture passer.

FIGS. 35A, 35B, and 35D show top and two side perspective views, respectively of the distal end of the suture passer shown in FIG. 34A.

FIG. 35C illustrates the arrangement of the tissue penetrator and suture stripper in the distal end region of the suture passer of FIG. 34A.

FIGS. 36A-36C show a suture stripper including a stripper plate (FIG. 36B) and base (FIG. 36C).

FIG. 38A shows a side sectional view and FIG. 38B shows a top perspective view.

FIG. 39A shows a side sectional view and FIG. 39B shows a top perspective view.

DETAILED DESCRIPTION

Figure 1B:
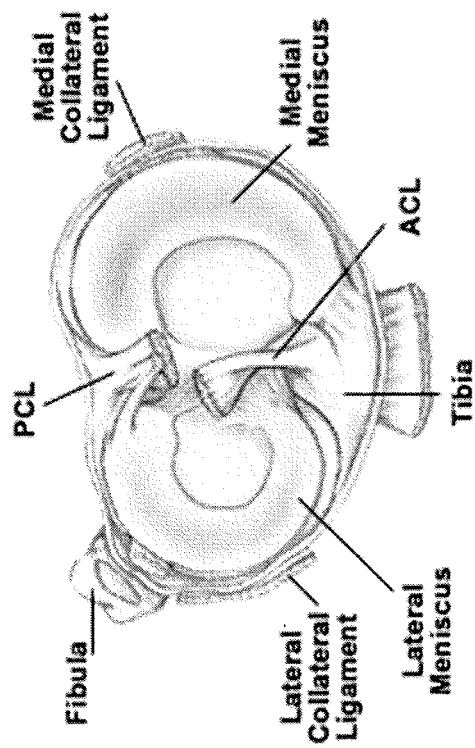
FIGS. 1A and 1B illustrate the anatomy of the meniscus of the knee.
Figure 1A:
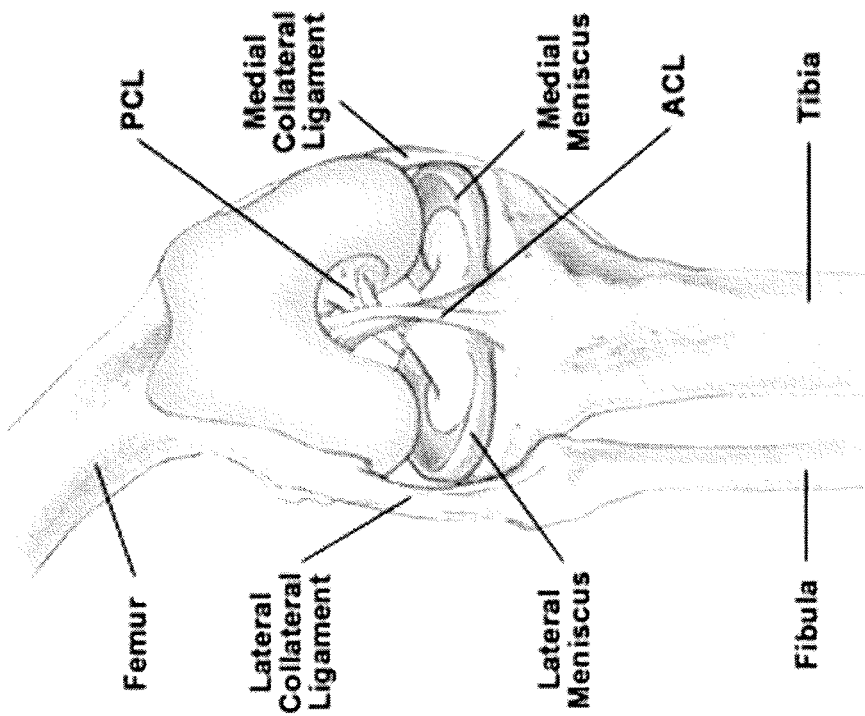
Figure 2:
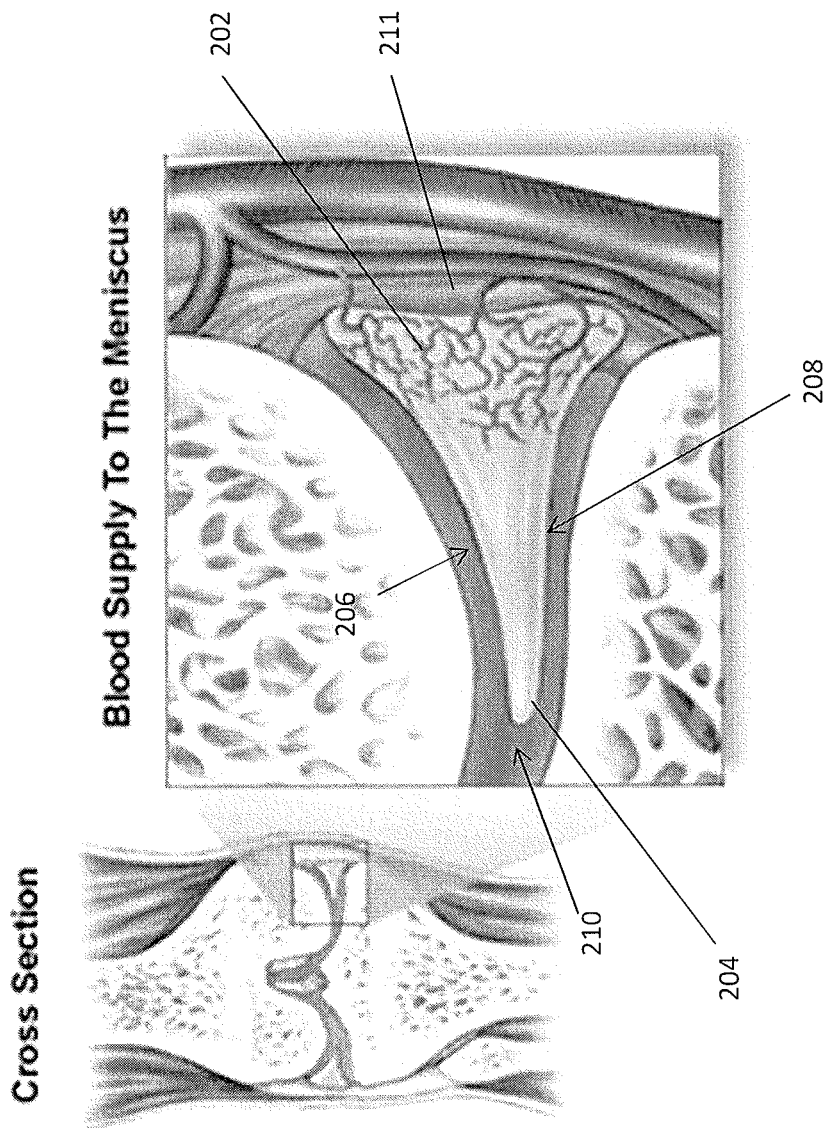
FIG. 2 illustrates the anatomy of the meniscus, including the capsule and associated vascular tissue.
Figure 3:
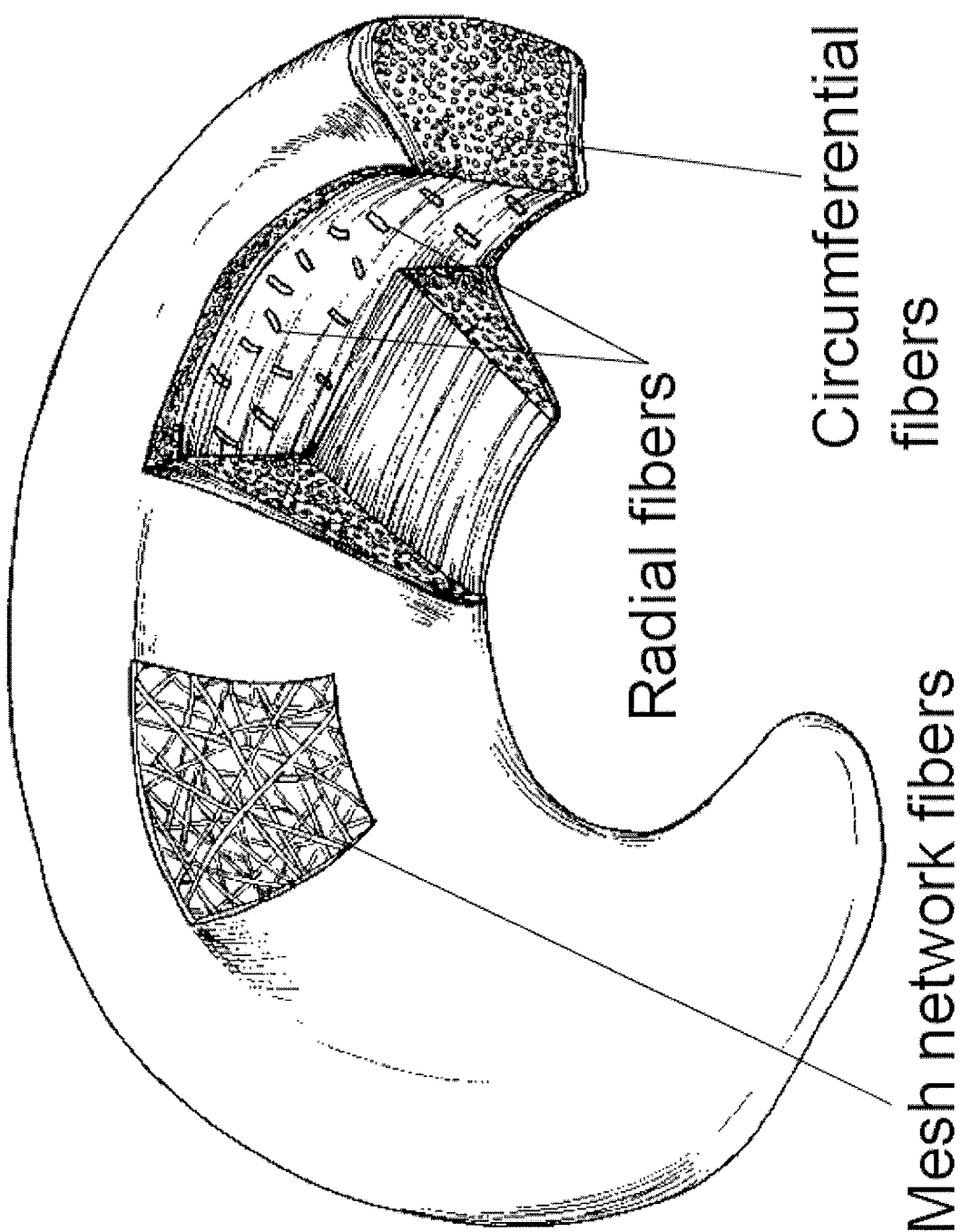
FIG. 3 illustrates the structure of a meniscus.

Described herein are methods of suturing tissue, and particularly, method of using a suture passer to create a locking loop of suture. As used herein a locking loop of suture is a loop of suture that is passed through a tissue from a first side to a second side of the tissue; one or more of the legs extending from the second side of the tissue are then passed through the loop of tissue eon the first side of the tissue, and cinched to tighten the loop closed over the one or more legs. In some variations one or both legs may be passed through the tissue (e.g., an adjacent region of the tissue) so that one or both legs of the loop of suture also extend from the first side of the tissue near the loop, before they are passed through the loop and locked down by tightening the loop. The loop may be tightened by pulling on the one or more legs to cinch it closed. In particular, these methods may be performed by a single suture passer such as the suture passers described herein which are adapted for passing a loop of suture through tissue, using the pair of distal-facing jaws in which one or the jaws may bend relative to the long axis of the suture passer, while the other jaw may slide proximally-to-distally in the direction of the long axis, and the suture passer (needle) can push or pull the loop of suture between this distal opening by being deflected from out of one of the jaws to extend across the distal opening, and then (in some variations) being deflected a second time to extend distally from the opposite jaw member.

Examples of these methods, as well as examples of the suture passers adapted to perform these methods, are described below. The examples provided illustrate repair of a meniscus root, repair of a radial tear of the meniscus, repair of a rotator cuff, and repair of a torn ACL. These examples are not intended to be limiting or exhaustive; other tissues may be similarly repaired using these methods and devices, including spinal tissues, other ligaments, fascia, and the like.

Meniscal Root Repair

In some variations, the methods of using a suture passer to for a locking loop of suture may be used for meniscal root repair. It is well-known in the art that repair of the meniscal root is both desirable and highly difficult. For any patient, even "ideal" young and highly active candidates, meniscal repair continues to represent a significant challenge. It is undisputed that vertical tears greater than 1 cm in the peripheral-third of the meniscus should be repaired, however, there has been new attention on repairing posterior root tears. With these root tear repairs, an inside-out repair is not feasible due to the posterior midline placement of the needles and the passage of the suture. (Nord and Krueger, Orthopedics Today, November 2010, at http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair, last visited May 29, 2013).

Both the medial and lateral menisci have a stout attachment at their very posterior aspects, which is called the root attachment. The root of the meniscus is the region where the meniscus attaches to the central tibial plateau. This root attachment is important because it holds the meniscus in place, provides stability to the circumferential hoop fibers of the meniscus, and prevents meniscal extrusion. When there is a tear of the meniscal root, it has been demonstrated on biomechanical testing that it is equivalent to having the whole meniscus removed. Thus, a tear of the meniscal root is considered a very serious condition. An example of a meniscal root repair is shown in FIG. 4F.

Meniscal tears within the body of the meniscus or at the meniscocapsular junction represent a well-understood and manageable condition encountered in clinical practice. In comparison, however, meniscal root tears (MRTs) often go unnoticed and represent a unique injury pattern with unique biomechanical consequences. The root attachments of the posterior horns of the medial and lateral meniscus are very important for joint health. When these are torn, the loading of the joint is equivalent to having no meniscus on the affected side. Thus, these patients can often have early onset arthritis, the development of bony edema, insufficiency fractures, and the failure of concurrent cruciate ligament reconstruction grafts. For this reason, much research has gone in to meniscal root repairs over the last several years.

However, current methods for repairing the meniscal root are not completely satisfactory. For example, meniscal repair techniques that suture the meniscus from the "outside" (e.g., though the capsule) may not properly restore the anatomy, for example, anchoring the meniscus to the posterior capsule, rather than the tibia.

A superior method of repairing a meniscal root is described below and two variations are illustrated in FIGS. 5A-5E and 6A-6F FIGS. 5A-5E show one variation of meniscal root repair using a double locking loop stitch. In this variation the root of the meniscus may be arthroscopically repaired using any of the suture passers capable of minimally invasively (e.g., arthroscopically) and being positioned on both the superior and inferior sides of the meniscus and passing a suture between the superior and inferior sides. Examples of these suture passers are described below. In this variation the legs of a loop of suture are each passed between the superior and inferior sides (e.g., from the inferior to the superior side) and then the middle region between the two is passed to form a loop on the superior side. The legs of the suture thus extend from the superior side in two different locations (e.g., radially and/or longitudinally spaced locations) and are pulled though the loop on the superior surface side then the loop is cinched (e.g., by pulling on one or both legs) to tighten it over the legs. The legs may then be secured to the tibia (e.g., into a tibial tunnel). Alternatively, the legs may be passed after the loop (the region of the suture length between the legs) is passed, or the first (e.g., distal) leg may be passed, then the loop (the region of the suture length proximal to the first leg) then the second (e.g., proximal) leg may be passed. Thus, the order in which the two legs and the loop region between them are passed between the first and second sides of the tissue may be varied in any of the methods described herein, unless otherwise specified.

Figure 5A:
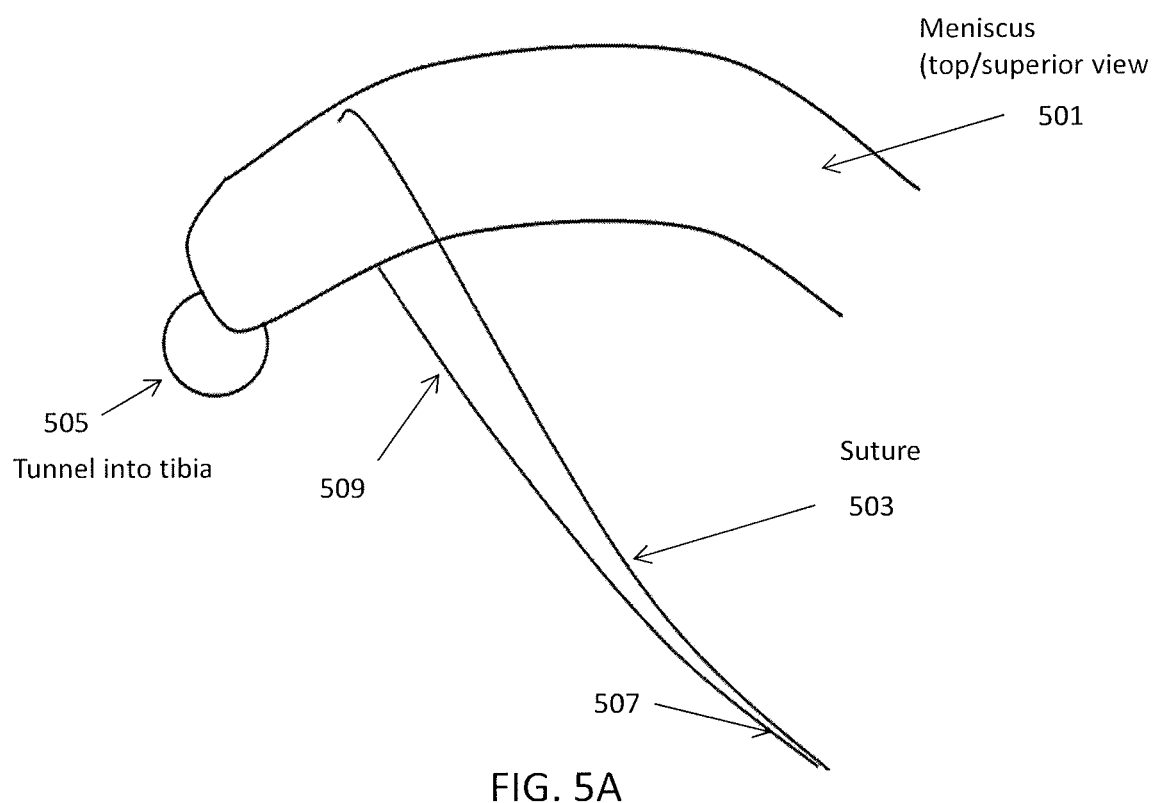
FIGS. 5A-5E show one variation of meniscal root repair using a double locking loop stitch.

In FIG. 5A, the first leg of the suture 503 has been passed from the inferior to the superior (top, facing) 501 surface of the meniscus. As described below, the suture passer may pass a distal "bight" (or loop) of suture by pushing or pulling it through the meniscus once the distal-facing mouth formed by the two jaws of the suture passer have been positioned (e.g., arthroscopically) around the meniscus. For example, the suture passer may arthroscopically access the meniscus of the knee with a first jaw retracted proximally (relative to the proximal-to-distal long axis of the shaft of the device); the second jaw may be bent or bendable (e.g., pivotable) at the distal end region of the shaft of the device. The second jaw may be positioned adjacent to the superior surface either before or concurrently with sliding the first jaw distally to extend it relative to the elongate shaft so that it is extended adjacent to the inferior surface of the meniscus, positioning the meniscus between the distal-facing jaws. The tissue penetrator (e.g., needle) may then push or pull the distal end region of the suture length through meniscus, e.g., from the inferior to the superior surface. If the suture is passed as a loop (e.g., bight) of suture, the distal most end of the suture may be drawn through the tissue until just a single-stranded length of the suture (corresponding to the first leg) passes through the tissue.

Figure 5B:
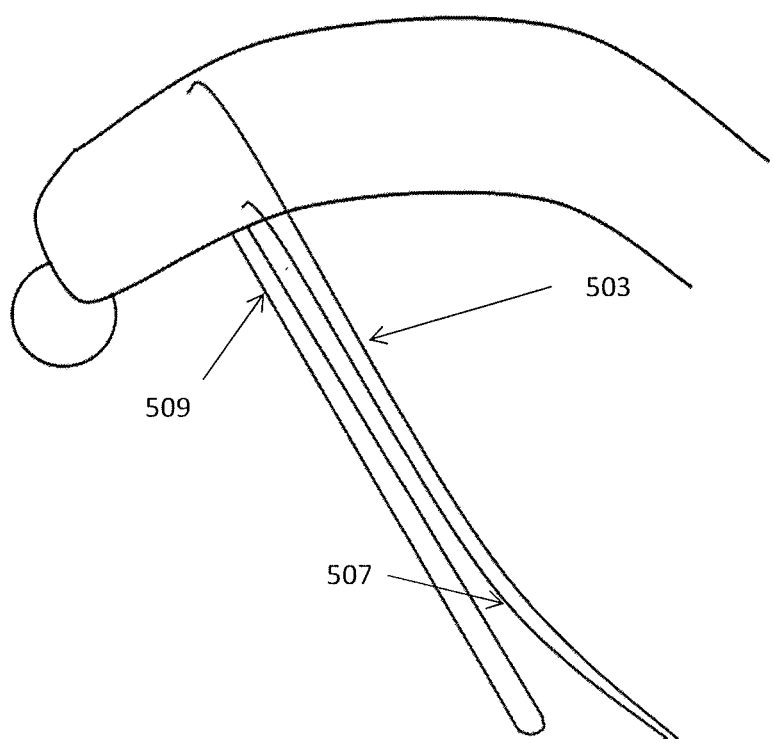
Figure 5C:
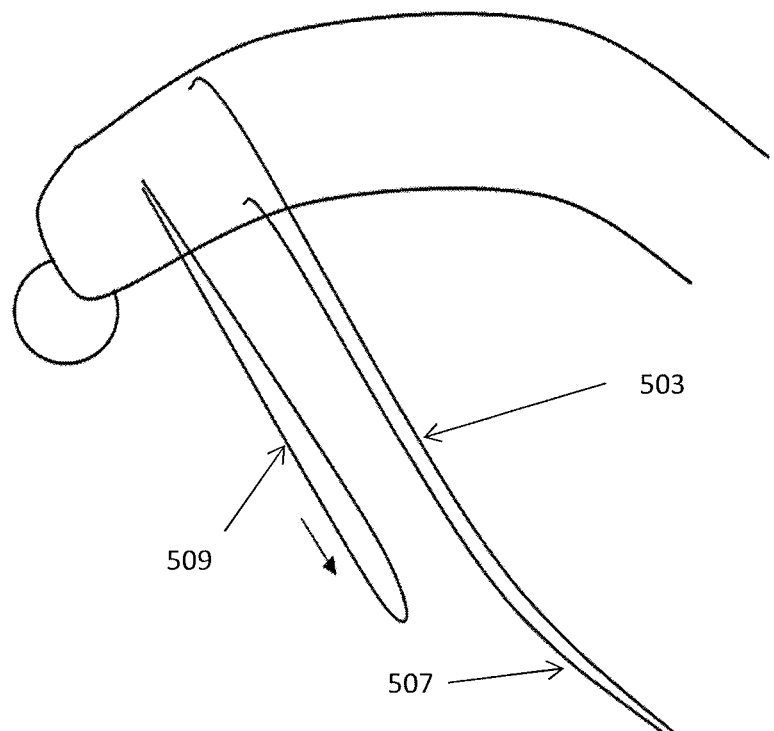

The second leg (e.g., the proximal end region) of the suture has been passed through a radially offset region of the meniscus from the inferior to the superior side as shown in FIG. 5B. In this example, the proximal end region or length 507 of suture may be loaded on to the suture passer (or it may have been pre-loaded onto the suture passer) and it is extended (e.g., as a bight or loop) though the meniscus from the inferior to the superior surface. The proximal end extended completely out of the meniscus so that both the first leg (the distal length of the suture) and the second leg (the proximal length of the suture) extend out of the superior side. The region between the first and second legs, the middle region, is located on the inferior side and may extend out of the patient, e.g., the access port for arthroscopically accessing the tissue. This central region may then be passed (as a loop or bight) by the same suture passer from the inferior to the superior surface of the meniscus, so that a loop 509 of the central region of the length of suture also extends from the superior surface of the meniscus, as shown in FIG. 5C. The loop may be passed in a radially intermediate region (between the first and second legs) transversely though the meniscus, as shown. The passage through the meniscus of the loop (and any of the legs) may also be laterally offset relative to the legs.

Figure 5D:
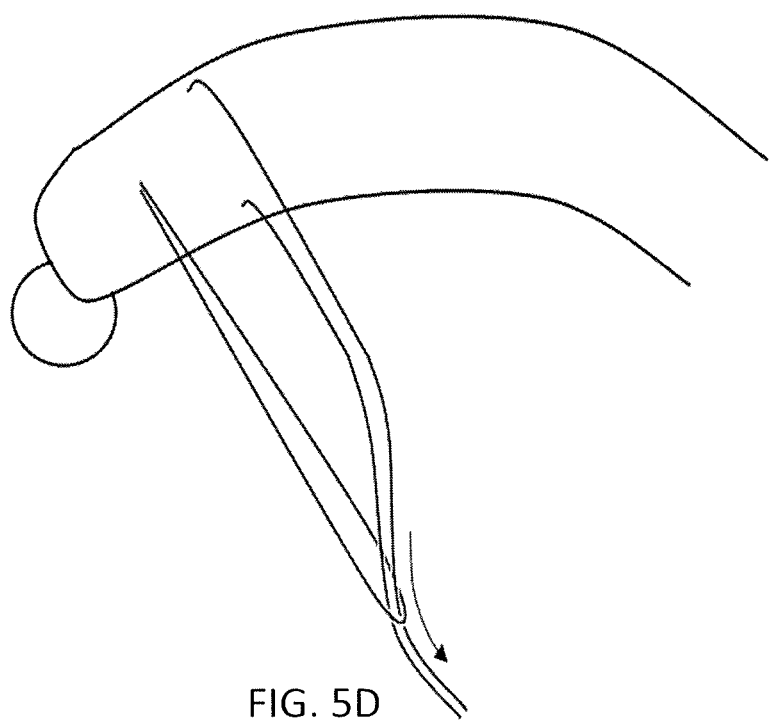
Figure 5E:
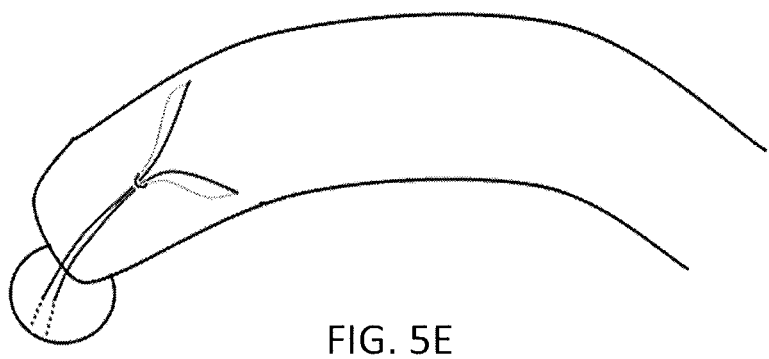

Thereafter, the first and second legs of the suture may be passed through the loop on the superior surface, as shown in FIG. 5D. This may be performed after withdrawing the suture passer, e.g., by a suture grasping instrument, hook, etc. The loop may then be cinched down over the legs of the suture, as illustrated in FIG. 5E, and the legs secured to the tibia. This may be done concurrently or separately. By pulling the legs of the suture, the loop may be cinched down, and the resulting double locking loop stitch may hold the end of the meniscus so that it can both be repositioned and secured relative to the tibial plateau. Additional sutures (including additional locking loop stitches) may be used.

Figure 6E:
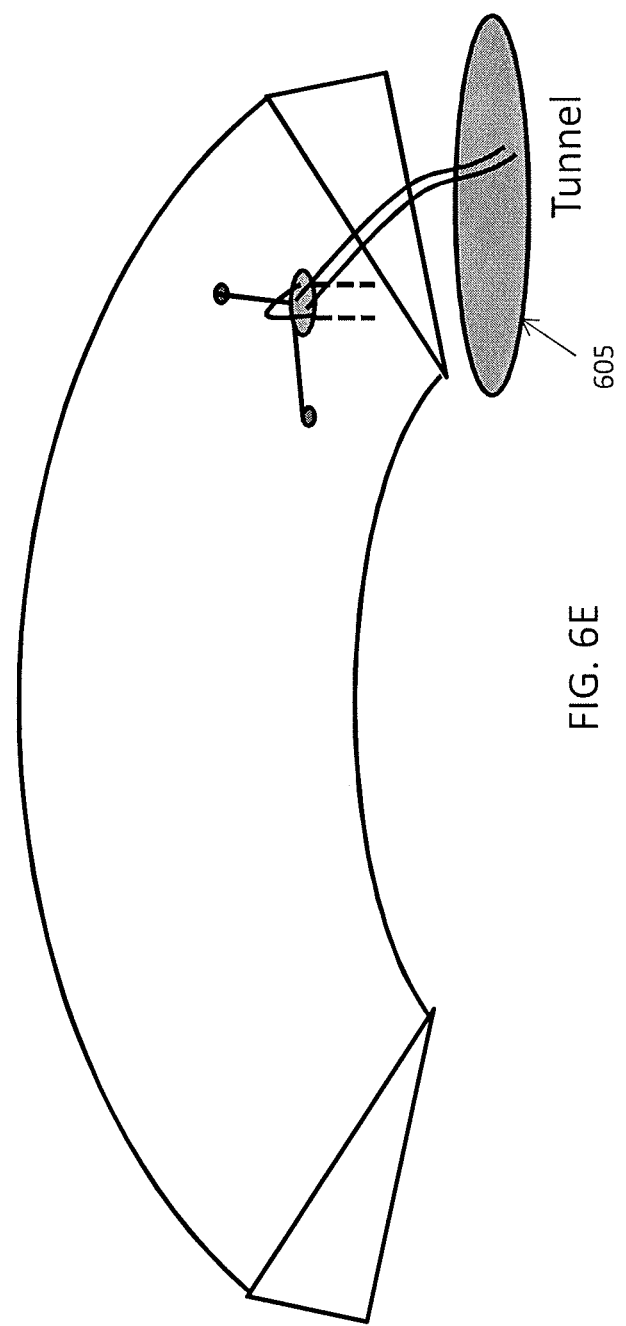

Another variation of a meniscal root repair is shown in FIGS. 6A-6E. In this variation, the perspective view shows the top/superior surface of the meniscus as well as the bottom/inferior surface of the meniscus. An access region through the tibia has been formed (tunnel 605) that may be used to secure the meniscus to the tibial plateau after forming the appropriate locking loop. A suture passer that is configured so that it can arthroscopically be positioned with a first jaw adjacent the superior surface and a second jaw adjacent the inferior surface and pass a length of suture between the superior and inferior surface may be used, and positioned as described above. In this example, the middle region of the length of suture to form the locking loop (double locking look) is passed first, as shown in FIG. 6B. For simplicity in all of these figures, the suture passer is not illustrated, but it operated as described below. Thus, a loop of the middle region 609 extends from the superior surface as shown. The suture length includes a distal region that will form a first leg and a proximal region that will form a second leg and a central region between the two forming the loop. As the central region loop is passed, the distal and proximal lengths remain outside of the subject, e.g., extending from the arthroscopic access port in the knee used by the suture passer. After passing the loop through the meniscus by the suture passer, the suture passer may be configured so that it releases the loop on the inferior side, allowing it to be repositioned to pass the first and second legs, while leaving the loop on the superior surface.

In FIG. 6C the first (e.g., distal) leg of the length of suture has been passed through the meniscus from the inferior to superior side, so that it extends from the superior side. Although only a short length of loop is shown ending form the superior side of the meniscus, the length may be longer. In addition, the figure does not show the adjacent bone regions (e.g., femur head and tibial plateau) that constrain the access to the meniscus, however, however they are typically present. Thus, the free ends of the first and second leg are shown extending away from the meniscus for convenience, in practice, they may be positioned between the superior surface of the meniscus and the femur head.

FIG. 6D shows the second leg after it has been passed by the suture passer from the inferior to the superior side of the meniscus. Finally in FIG. 6E, the ends of the first and second leg have been pulled through the loop and into the tibial tunnel 605, so that they can be used to cinch the loop and secured to hold the meniscus in place. Additional sutures (including additional locking loops) may be used.

Figure 7A:
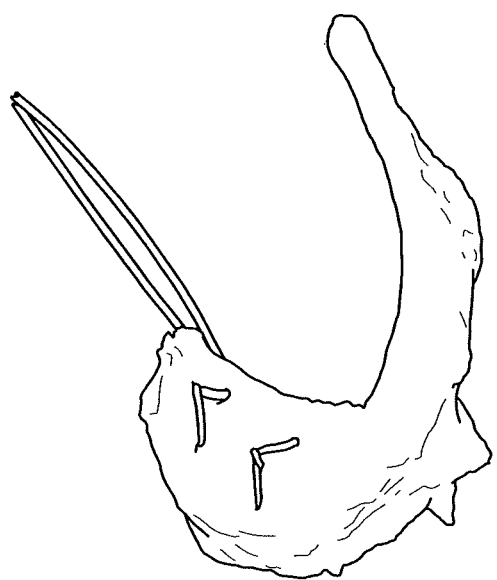
FIGS. 7A-7C illustrate a meniscus repaired by a method similar to that shown in FIGS. 5A-5E and 6A-6E.
Figure 7B:
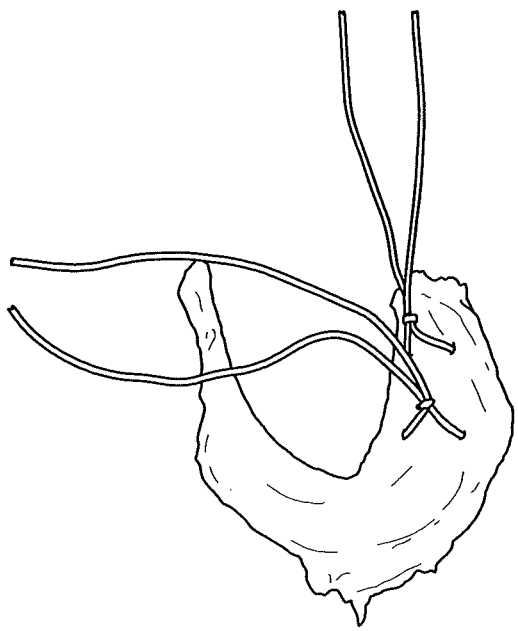
Figure 7C:

FIGS. 7A and 7B illustrate the inferior and superior sides of a meniscus that has been removed from the body after forming two locking loops as discussed above. The resulting stitches have a chevron-like pattern on the superior and inferior surfaces of the meniscus. FIG. 7C shows a model of the knee, with the femur removed, in which a meniscal root has been repaired by this method.

Meniscal Radial Tear

The method of forming a locking loop of suture may also be used to repair other tears and regions of the meniscus, including, but not limited to radial tears. This is illustrated in FIGS. 8A-J. In this example two locking loop sutures are used, one securing each side of the tear 801, and then the two may be connected or bridged to pull the sides together. Having a loop of suture on each side of the tear (laterally offset) may provide additional strength to hold the sides of the tear in apposition without placing too much strain on the side regions of the meniscus, forming a very strong suture.

In FIG. 8A, the radial tear 801 is shown. A percutaneous access port 802 is used to access the knee and the "inside" of the central region between the meniscuses. The same suture passer described above may be used. This locking loop suture pattern may be formed by a suture passer that can be positioned arthroscopically in the knee so that a first jaw is positioned between the superior surfaced and the femur head, a second jaw if positioned between the inferior surface and the tibial plateau, and a tissue penetrator can push or pull a suture bight between the superior and inferior surfaces. Examples of such suture passers are provided below. In FIG. 8A, such a suture passer has been used to pass a loop of suture 803 from the inferior to the superior side of the meniscus and back out of the knee, as shown. The first 805 and second 807 legs also extend from the knee.

Figure 8E:
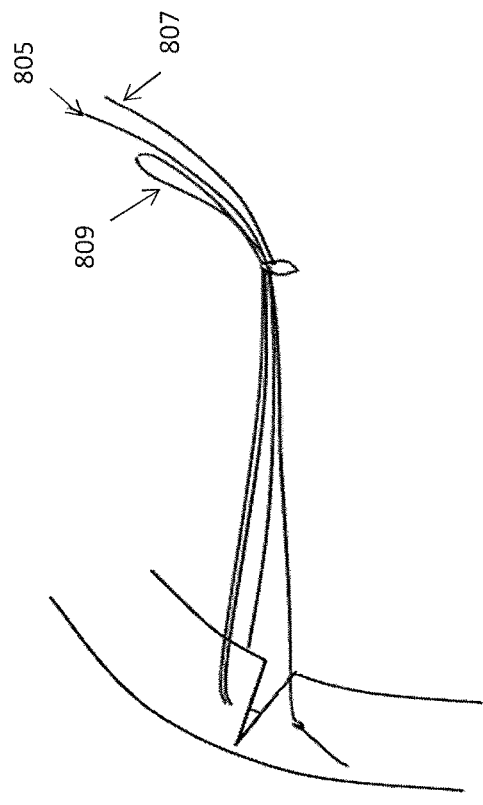

In FIG. 8B, the first leg has been passed (using the same suture passer, e.g., by reloading with the first leg length of suture) from the inferior to the superior side of the meniscus, and the first leg is drawn back out of the knee, as shown in FIG. 8C. The first leg 805 may then be passed through the loop 803. The loop may then be cinched, by pulling the first leg, as shown in FIGS. 8D and 8E.

Figure 8F:
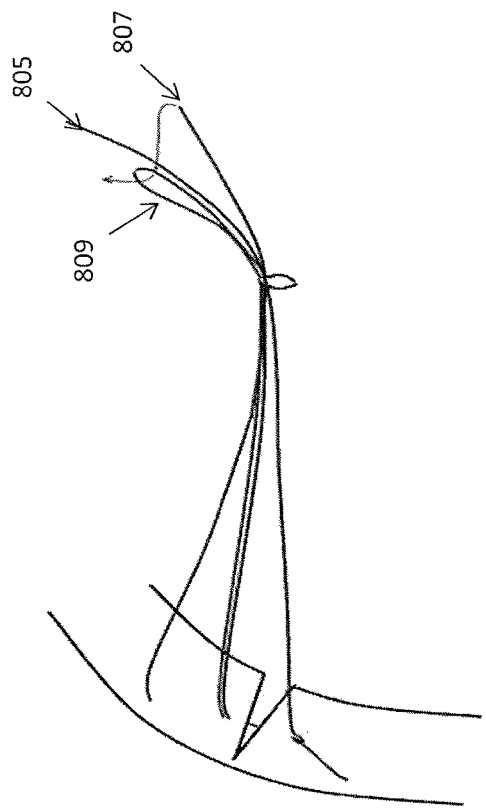
Figure 8G:
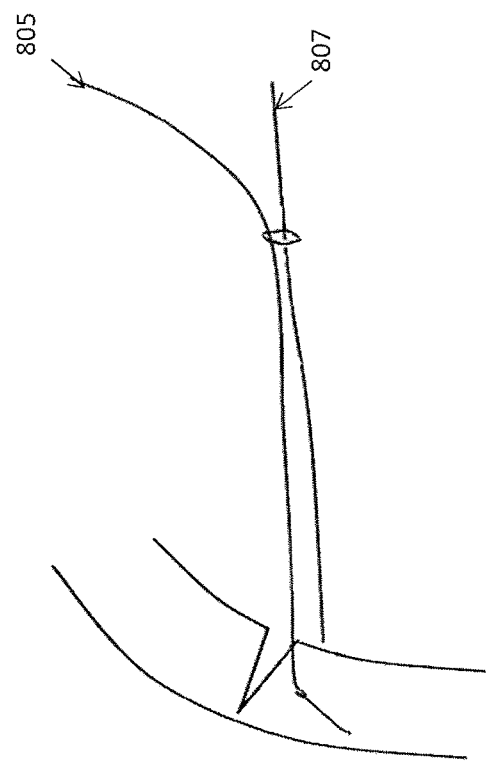

Thereafter, a loop 809 formed of the second leg or length of suture may be passed, using the suture passer, through the meniscus on the opposite side of the tear from the inferior to the superior side, as shown in FIG. 8F. This loop may be formed of a region intermediate between the cinched loop 805 and the distal end of the second leg 807. The second leg may then be loaded on to the suture passer and passed from the inferior to the superior side, and withdrawn from the knee, as shown in FIG. 8G. Although the method illustrated above include the steps of removing the passed suture lengths (loop, first and second leg) out of the knee, this is not necessary, though it may be helpful for managing the many lengths and loops of suture.

Figure 8H:
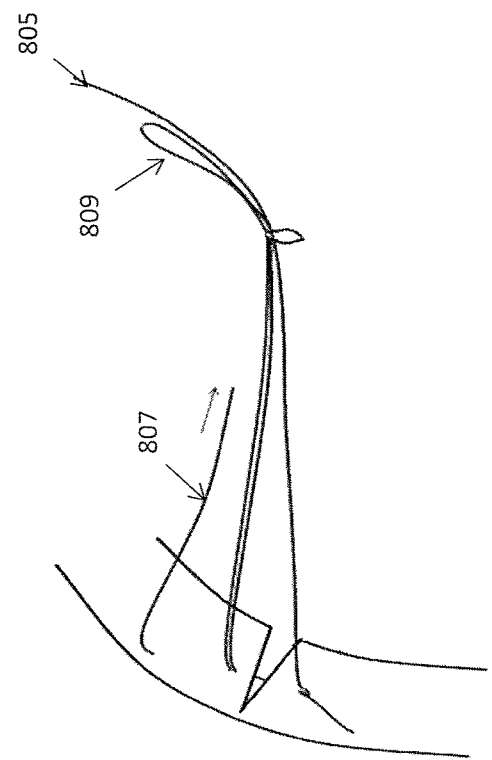
Figure 8I:
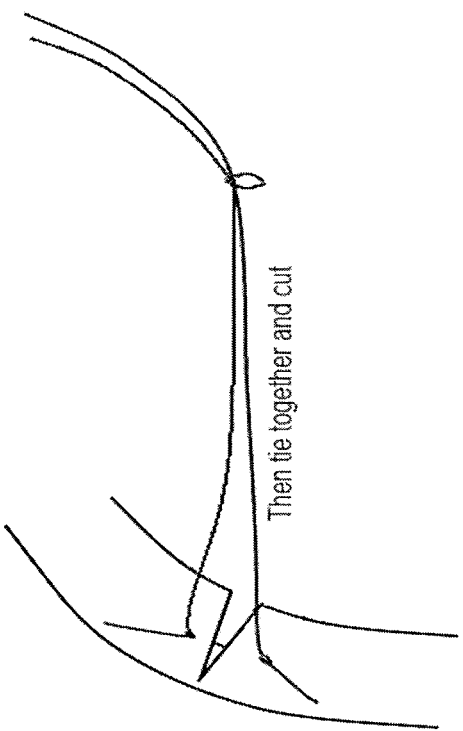
Figure 8J:
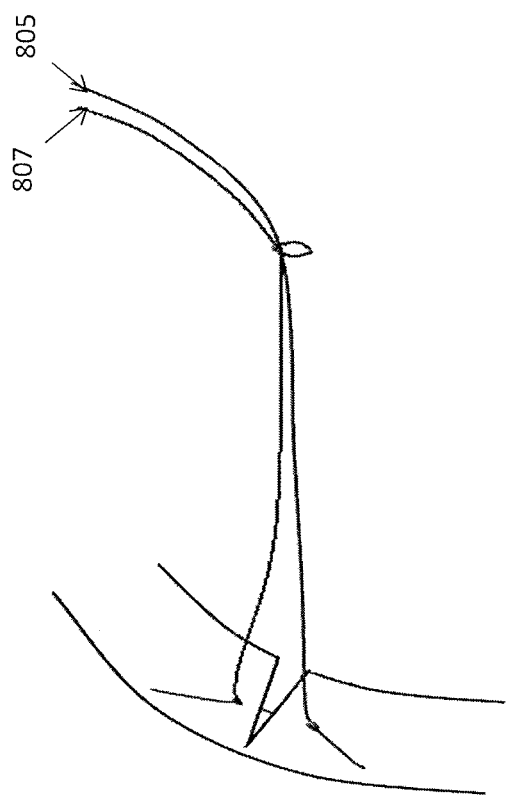
Figure 9A:
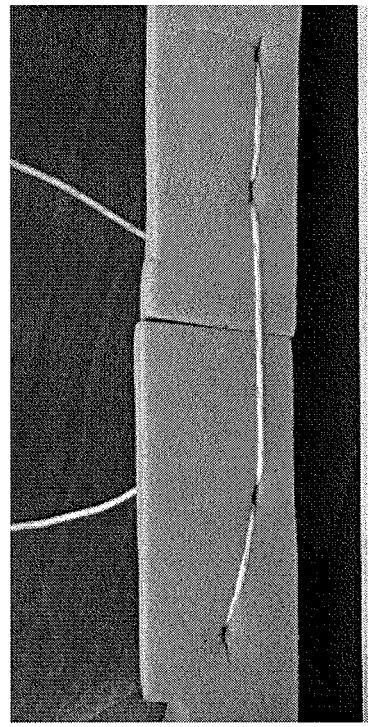
FIGS. 9A-9B illustrate the superior and inferior sides of an exemplary meniscus, sutured as shown in FIGS. 8A-8J.
Figure 9B:
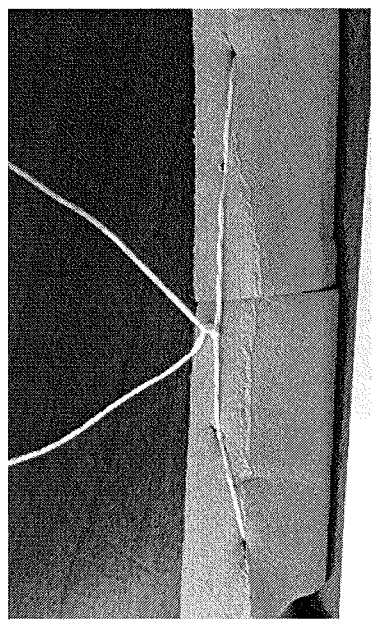

In FIG. 8H, the proximal end of the second leg 807 of suture is then passed through the second loop 809, and the second loop is cinched by pulling on the second leg, as shown in FIG. 8i, leaving the first and second legs extending out from the superior side of the meniscus. These ends may then be knotted, and the knot tightened to bring the torn sides of the meniscus in apposition and secured together, as illustrated in FIG. 8J. FIGS. 9A and 9B illustrate the superior and inferior sides of an exemplary meniscus, sutured as described above.

Figure 9C:
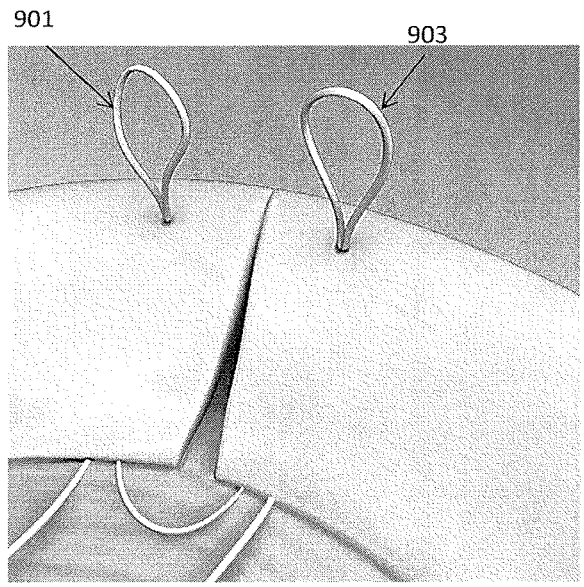
FIGS. 9C-9J illustrate another variation of a method for repair of knee tissue (e.g., radio tears in the meniscus of the knee) using a pair of locking loop structures.
Figure 9D:
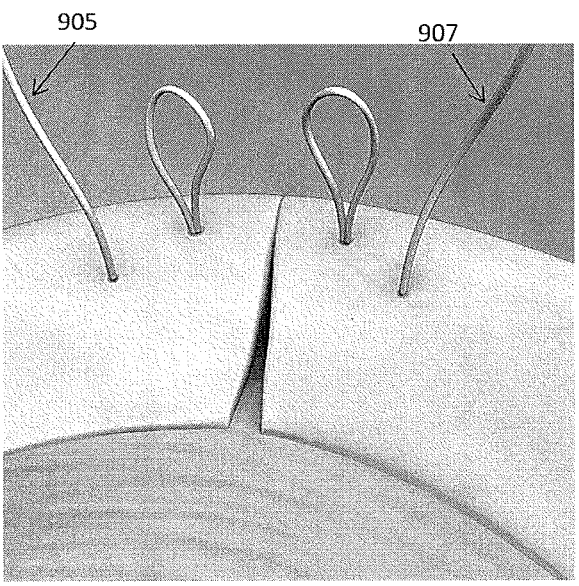

FIGS. 9C to 9J illustrate another method of using a pair of loops formed in a single loop region of a length of meniscus to repair a radial tear in the meniscus. Any of the suture passers described and incorporated by reference herein may be used to (e.g., arthroscopically) repair the torn meniscus as illustrated. In FIG. 9C, a single suture, that includes a central loop region between a proximal leg region and a distal leg region (e.g., proximal end region and distal end region) is used to initially pass a first loop 901 on one side of the radial tear and a second loop 903 on the opposite side of the radial tear. For example, a suture passer preloaded with suture may be used to pass the first loop (length) from the inferior to the superior side of the meniscus, so that the loop project from the superior side, as shown in FIG. 9C. The distal and proximal end regions of the suture may then be passed lateral to the loops, as shown in FIG. 9D. The suture passer may be re-loaded with the proximal end/leg region 905 and passed, e.g., initially as a loop, so that the proximal end of the suture can be completely pulled through the tissue so that the proximal end is on the superior side of the meniscus as shown; this procedure may then be repeated with the distal end/leg of the suture 907 on the opposite side of the tear, lateral (and slightly radially) offset from the second loop, as shown.

Figure 9E:
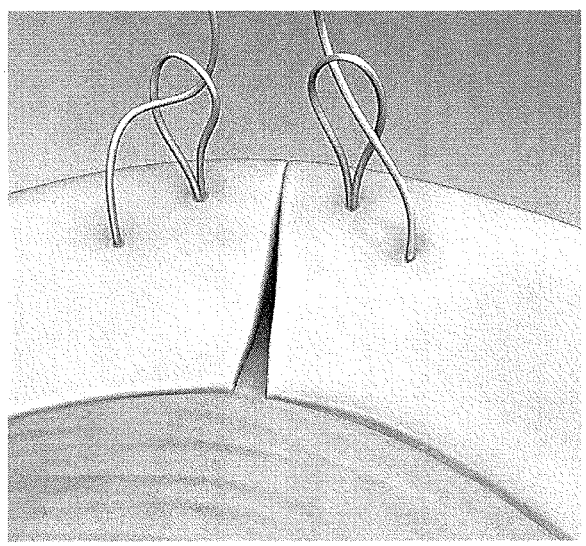
Figure 9F:
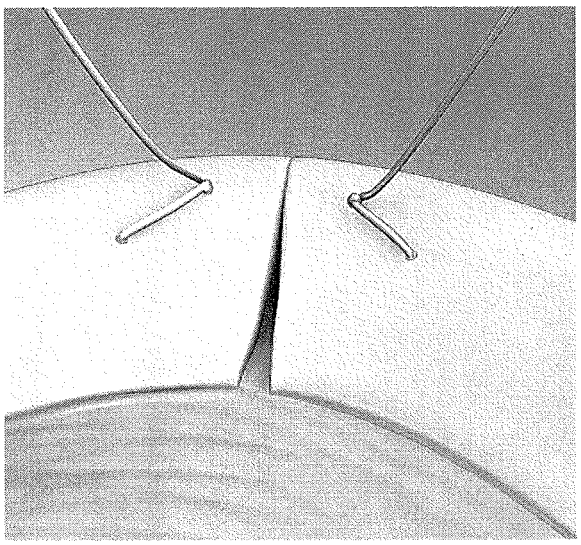
Figure 9G:
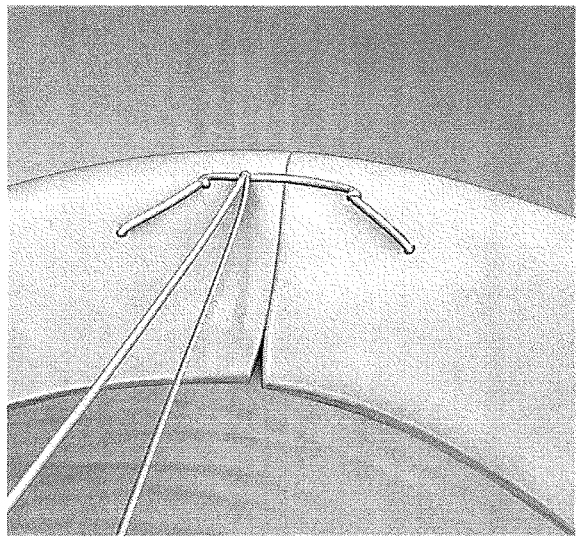
Figure 9H:
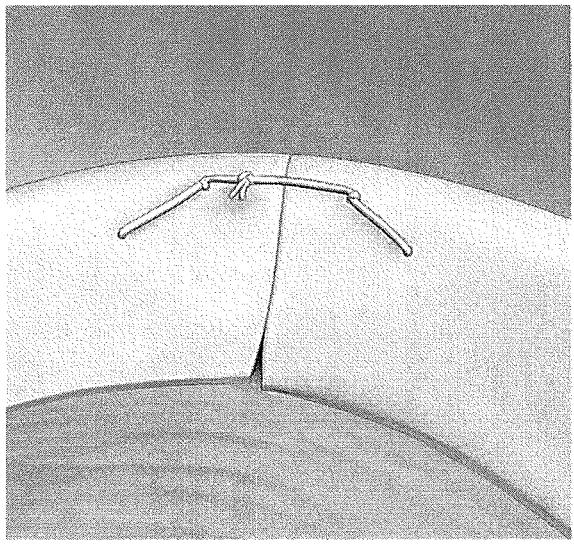
Figure 9I:
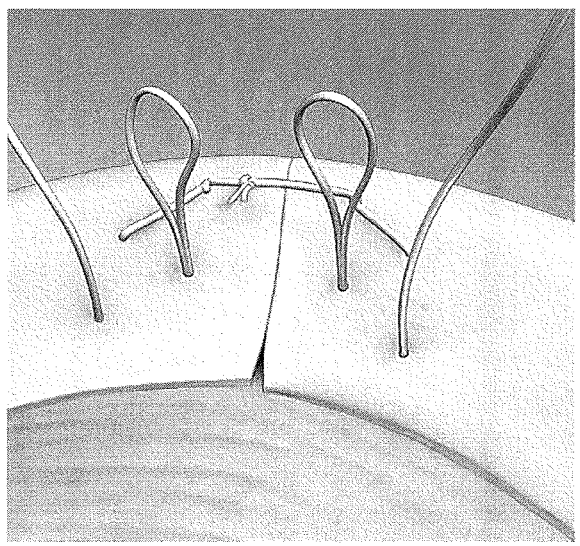
Figure 9J:
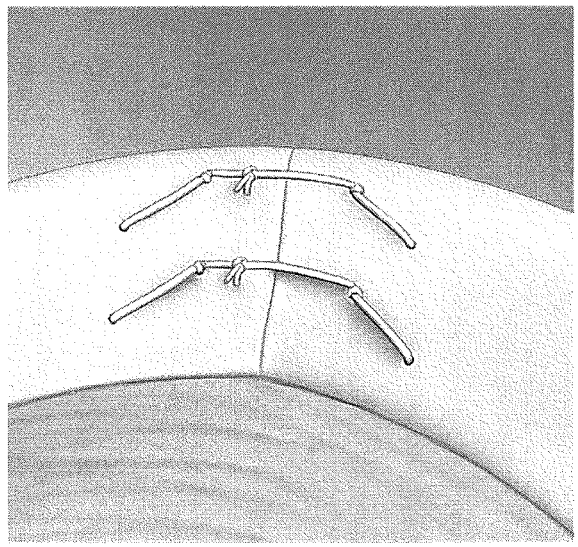

As shown in FIG. 9E, the proximal and distal ends of the suture may then be pulled through the first and second loops, respectively. These ends may then be pulled to cinch the loops and pull the tissue together, as shown in FIG. 9F. Once the loops are pulled taught, as shown, the proximal and distal legs maybe tied together over the superior surface of the meniscus, across the radial tear, as shown in FIG. 9G. Once knotted, the ends may be cut, as illustrated in FIG. 9H. This procedure may then be repeated across a second, radially offset, region of the radial tear, as summarized in FIGS. 9I and 9J. In some variations, only a single length of suture (e.g., stopping at the step shown in FIG. 9H) is performed to secure the tissue; in other variations additional length of suture (not shown) may be used.

Figure 38B:
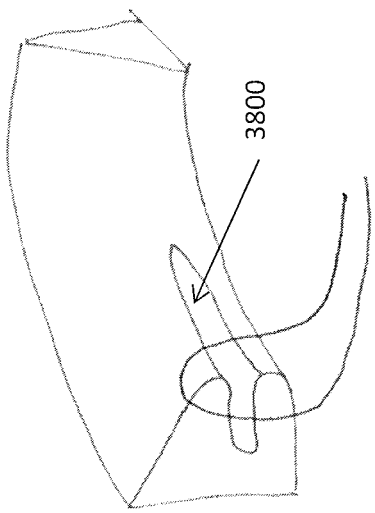
FIGS. 38A and 38B illustrate another example of a suture that may be formed arthroscopically ("hay bale stitch") to repair a torn meniscus having a horizontal cleavage tear.
Figure 38A:
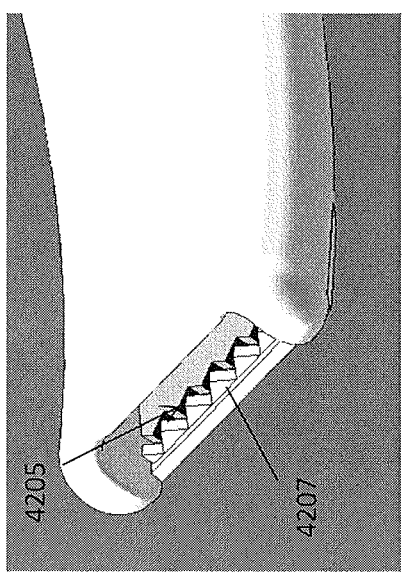

Other variations of suture patterns (stitches) that may be performed arthroscopically to repair a torn meniscus, and in particular, using the suture passers described herein, are also possible. For example, FIGS. 38A-38B illustrate a "hay bale" stich that may be used to repair a torn meniscus, and in particular a meniscus that has a horizontal cleavage tear 3800. In a horizontal cleavage tear, the meniscus is divided up into two layers, an inferior ("bottom") region and a superior ("upper") region. The inferior portion extends radially further than the superior region because of the angle of the superior surface. In a hay bale type stitch, a single length of suture is passed through the meniscus a single time through both the inferior and superior regions, as shown in the sectional view of FIG. 38A. The suture may then be cinched so that the resulting loop of suture passes has a single length of suture that passes through the meniscus and the rest of the loop extends outside, around the apex of the meniscus. The un-tied loop is shown in FIG. 38B. To form this suture, the suture passer such as the ones described herein may be positioned with a lower jaw adjacent to the inferior surface and the upper jaw adjacent to the superior surface, and the suture may be passed (e.g., from the bottom to the top or from the top to the bottom) between the superior and inferior surfaces, then one end of the suture pulled out so that both ends of the suture length may be knotted together to form the complete loop.

Figure 39B:
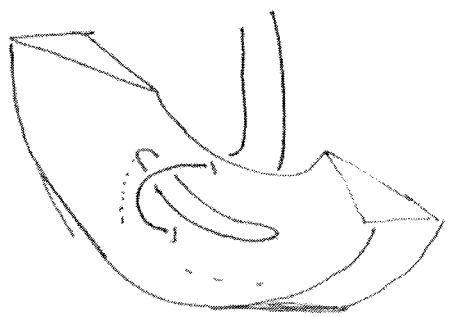
FIGS. 39A and 39B illustrate another example of a suture that may be formed arthroscopically ("cleavage stitch") to repair a torn meniscus having a horizontal cleavage tear.
Figure 39A:
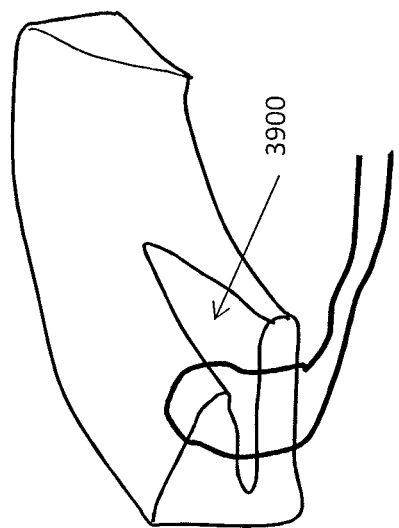
Figure 39C:
FIG. 39C illustrate another example of a cleavage suture, similar to the one shown in FIG. 39A, above, that may be formed arthroscopically to repair a torn meniscus having a horizontal cleavage tear.

Another variation of a suture that may be used to repair a horizontal cleavage tear is shown in FIGS. 39A, 39B and 39C. In FIG. 39A, the meniscus includes a horizontal cleavage tear 3900 that is repaired by forming a loop of suture in which two portions are passed through the inferior portion of the meniscus (the lower portion) formed by the tear and a single portion of the suture loop passes through the superior portion (upper) of the meniscus. The stitch shown in FIG. 39A may be knotted, e.g., with a knot pusher, by knotting the two ends of the suture together for form the complete loop. FIG. 39B shows a top view of this stitch (unknotted). This stitch may be referred to as a cleavage stitch. The stitch shown in FIGS. 39A and 39B may be formed by passing a first bight (e.g., loop) of suture from the inferior surface, e.g., by positioning the lower jaw against the inferior surface and the upper jaw against the superior surface) to the superior surface, then pulling the distal end of the suture all the way through, leaving the suture spanning the thickness of both the inferior and superior regions through the horizontal cleavage tear. The distal end of the suture (exiting the superior side of the meniscus) may then be passed from the superior side just through the inferior portion, and pulled through the inferior side, so that both ends of the suture extend from the inferior side of the meniscus, as shown in FIGS. 39A and 39B. For example, a suture passer that passes from a lower jaw to an upper jaw may be used to pass the first length of suture from the inferior to the superior side, and then the suture passer may be flipped over and used to pass the distal end of the suture extending from the superior side through the inferior portion (only) of the torn meniscus. In this example, the free ends of the suture extend from the inferior side and may be knotted so that the knot is on the inferior side.

Alternatively, FIG. 39C shows another example of a cleavage stitch in which the suture is passed from the inferior to the superior surface of the meniscus, through the horizontal cleavage tear, and the proximal end of the suture is then re-loaded and passed from the inferior to the superior surface to form the stitch shown in FIG. 39C. As before, this stitch may then be completed by knotting the two ends (proximal and distal) of the suture to form a loop in which the inferior portion has two lengths of suture passing through it while the superior portion has only a single length of suture. In this example, the knot may be formed on the superior side of the meniscus.

Rotator Cuff Repair

A method of forming a locking loop of suture as described herein may also be used to repair the rotator cuff.

The basic premise of repairing tissues such as the ACL and the rotator cuff using a suture passer to form the suture patterns (e.g., locking loop, double locking loop) described herein is same. A central portion of a length of suture is arthroscopically passed through a tissue, and then one or both terminal ends (arms, limbs, etc.) is arthroscopically passed through and/or around the tissue and through the previously passed loop, and the loop is cinched down. Thus, generally described herein are methods of arthroscopically passing a locking suture pattern through a tissue by: passing a non-terminal portion of the length of suture through the tissue, passing a terminal portion of the suture through a different location on the tissue, and passing the terminal portion of the suture through the loop so that a locking pattern is achieved.

Figure 10F:
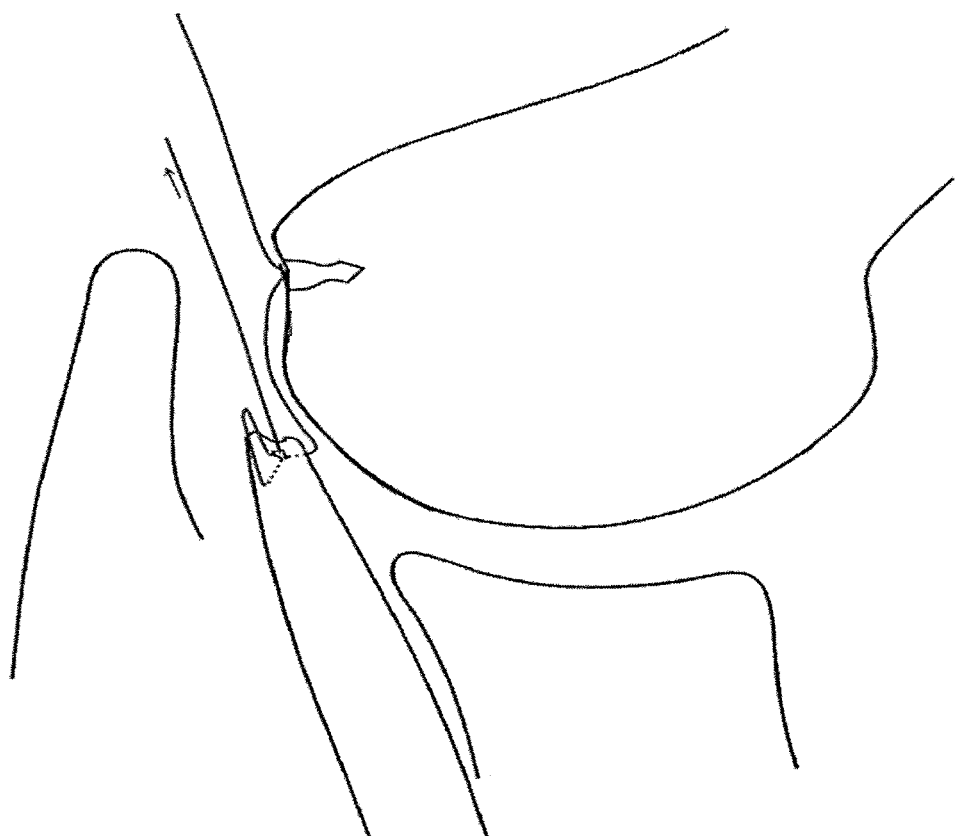
Figure 10E:
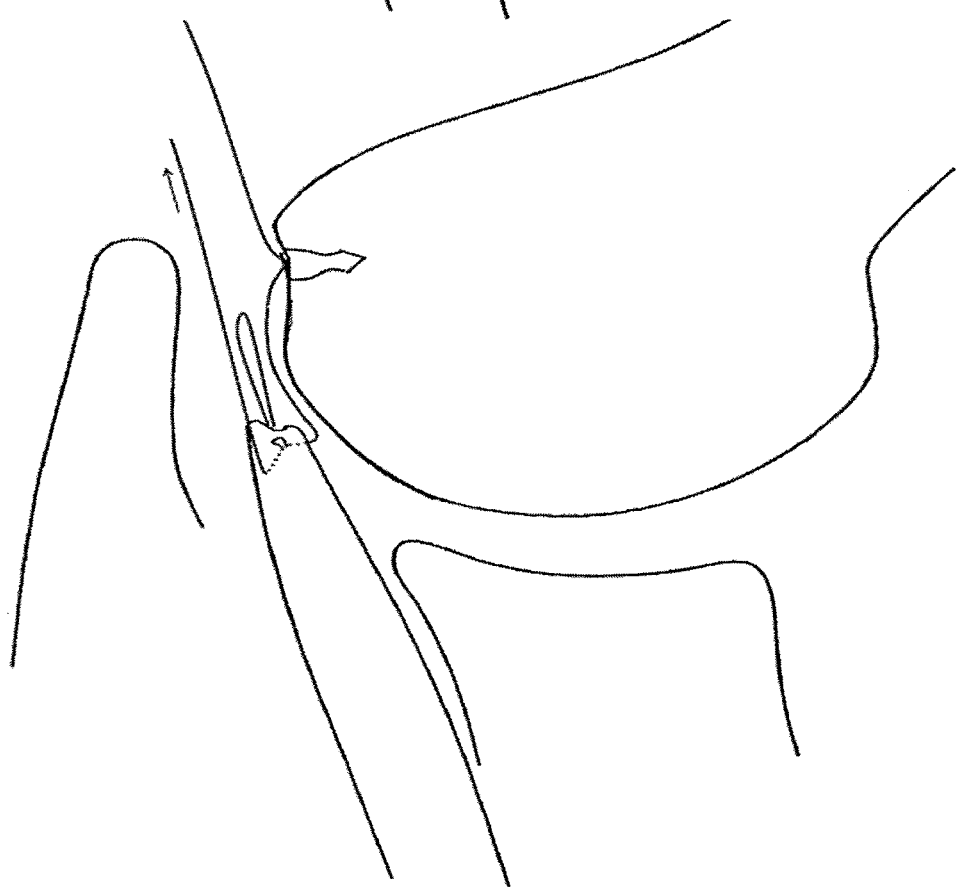
Figure 10H:
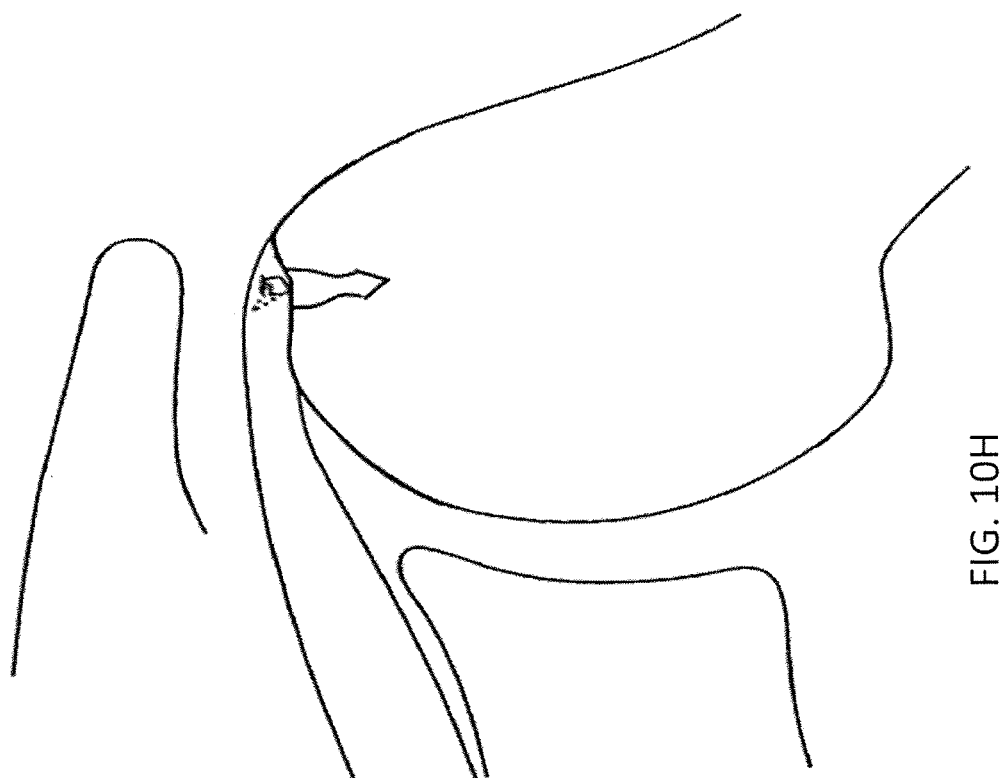
Figure 10G:
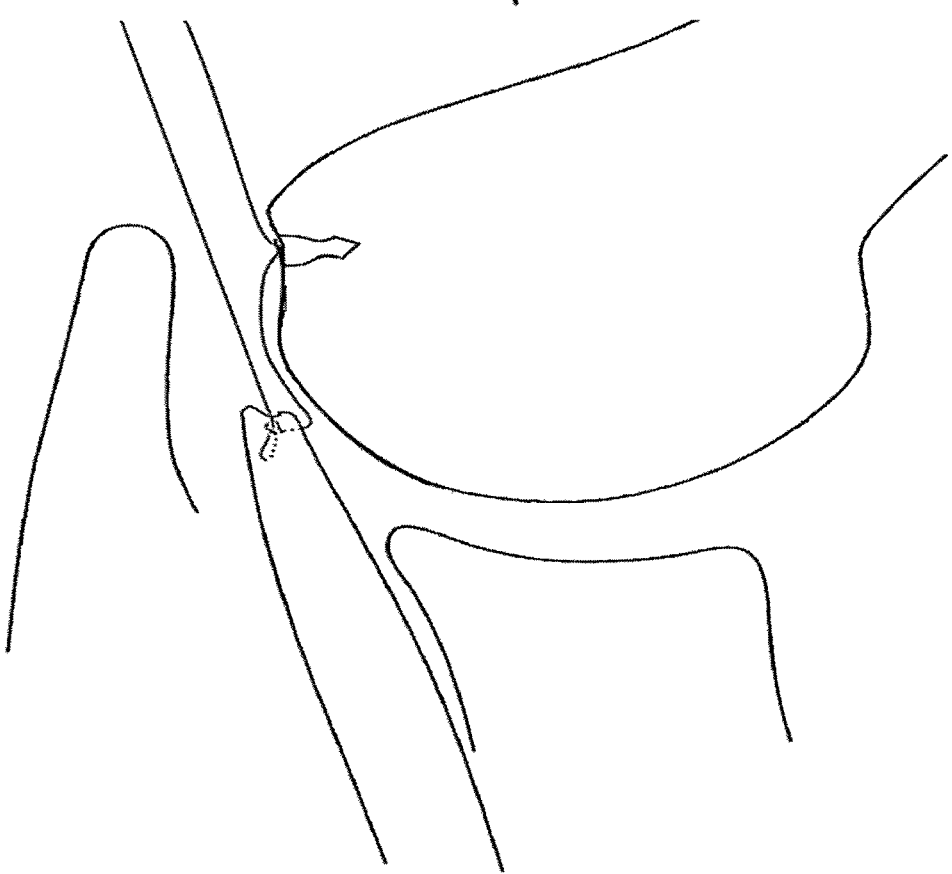

FIGS. 10B-10i illustrate rotator one method of repairing a torn rotator cuff using a suture passer to form a locking loop, in conjunction with a suture anchor. FIG. 10A shows an intact shoulder region in which the supraspinatus is attached to the humeral head. In FIG. 10B, this tendon is shown torn from the humeral head. The suture passers described herein may be used to repair the tissue arthroscopically by passing the suture to form a locking loop, even despite the space restrictions of the shoulder region. In FIG. 10C, an anchor has been secured to the humeral head; in practice, the anchor may be attached before or after the tendon has been sutured, so that it may be connected by the suture to the anchor and therefore the humeral head. In this example, a suture anchor has been secured to the humeral head and a length of suture is attached. This length of suture may be used to form the locked look by the suture passer. In some variations, the suture passer can be loaded with the pre-attached suture to pass the suture through the tendon, as shown in FIG. 10D. In this example, a distal end of the suture extending from the anchor is passed through the torn tendon from a first side of the tendon to a second side of the tendon. Although it may be passed as a bight or loop, the end is pulled completely through the tendon, so that it extends through as a single strand. Thereafter, as shown in FIG. 10E, the same suture passer may be used to pass a loop region of the same suture (proximal to this distal end region) through in the same direction, from the first side to the second side of the tendon. The free distal end of the suture may then be passed through the loop, and the loop may be "locked" by drawing on the distal end of the suture to cinch the loop closed, as shown in FIGS. 10F and 10G. The locked loop may then be secured (e.g., tied) to the anchor, as shown in FIG. 10H. For example, the free end of the locked loop may be tied off to the free end of the anchor, pulling the tendon in position and securing it to the humeral head, as illustrated. The loose ends of suture may then be removed.

Is should be noted in any of the methods described herein that the locking or locked loop formed may be freely cinchable; the loop is locked relative to the tissue, so that it does not pull out or come off of the tissue. However, the portions of the suture forming the locking loop may slide relative to each other.

Any appropriate anchor may be used with any of the method described herein when suturing tissue with a locking loop as described. For example, a knotless anchor may be used, or a traditional anchor. FIGS. 10C-10H illustrate a traditional anchor, where only one end if the suture is passed (the other end may be used to tension the repair to the bone).

ACL Repair

Figure 11B:
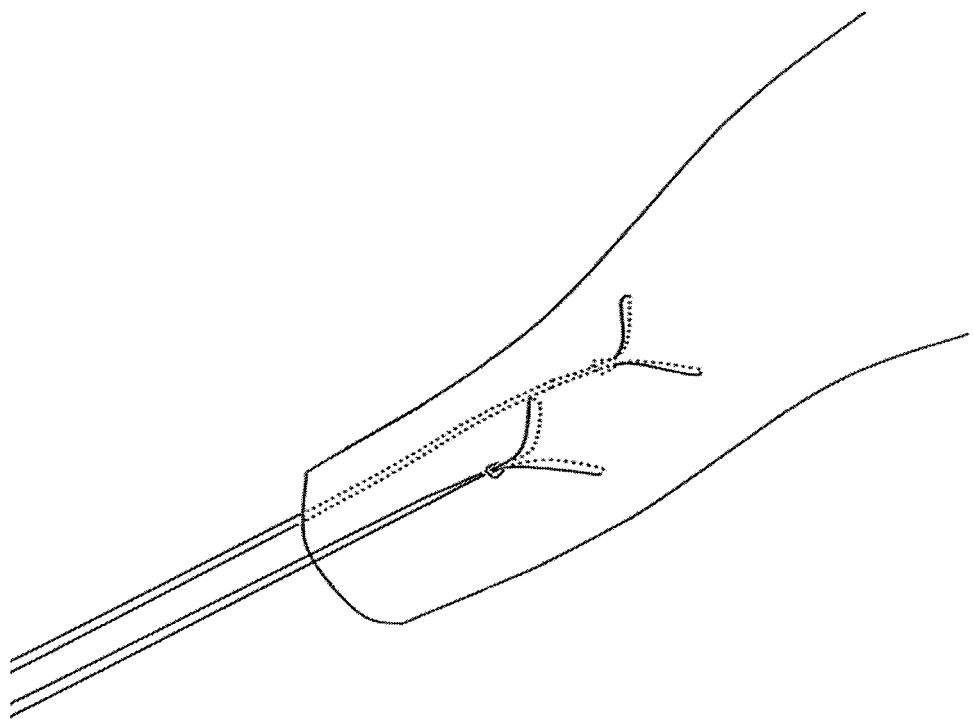
FIGS. 11A-11E and 12A-12C illustrate variations of locking loops used as part of an ACL repair.
Figure 11A:
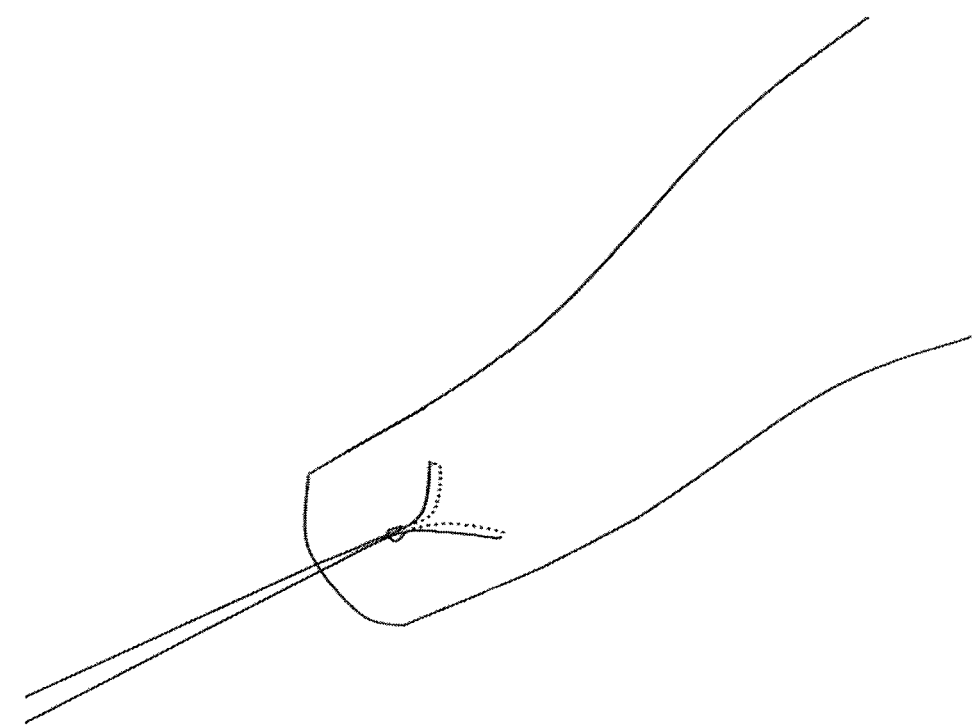

The locking loop pattern described herein may also be used to repair a torn ACL. FIGS. 11A-12C illustrate variations of locking loops used as part of an ACL repair. For example, in FIG. 11A, a dual locking loop has been passed through the torn end region of the ligament. Both legs and a loop region of the suture have been passed forming a triangle between the two, with the two leg regions passed through the loop before cinching it down, similar to the dual locking loop illustrated above in FIGS. 5A-6E. FIG. 11B is another example of a method of repairing the ACL in which to separated locking loops have been passed; both sets of free suture legs may be secured to the femoral head in this example.

Figure 11D:
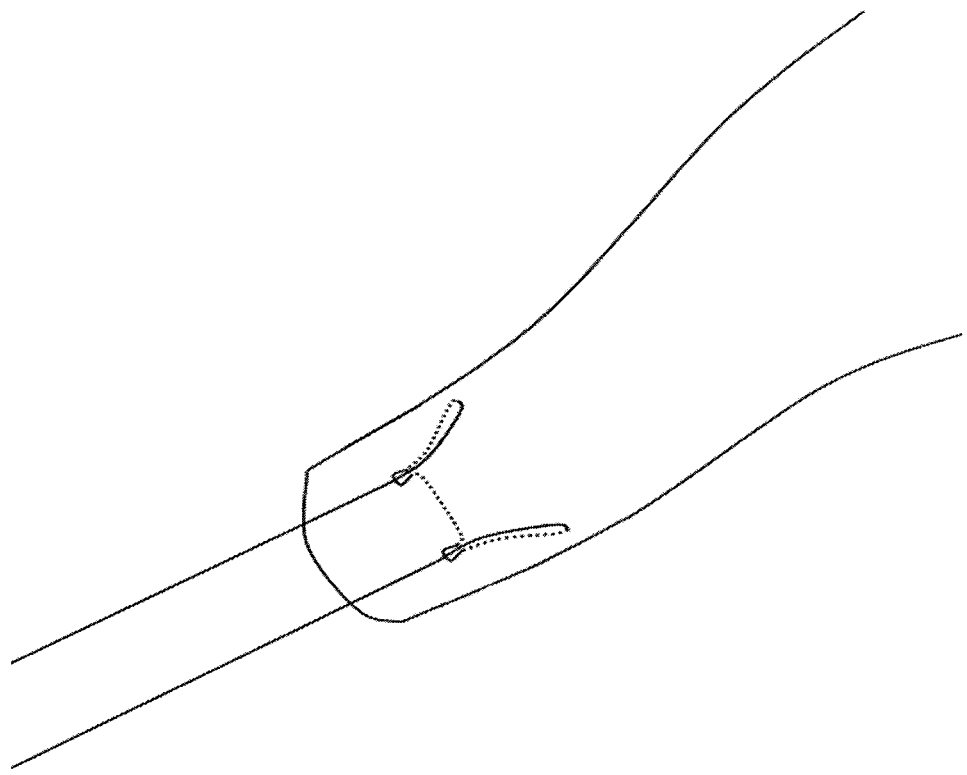
Figure 11C:
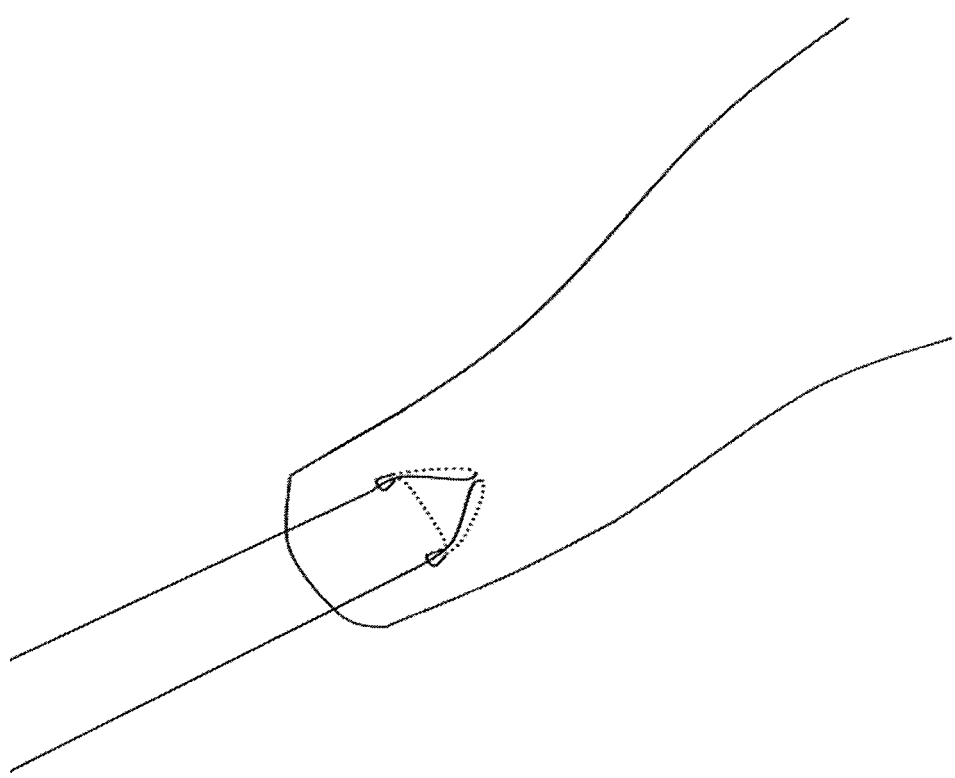
Figure 11E:
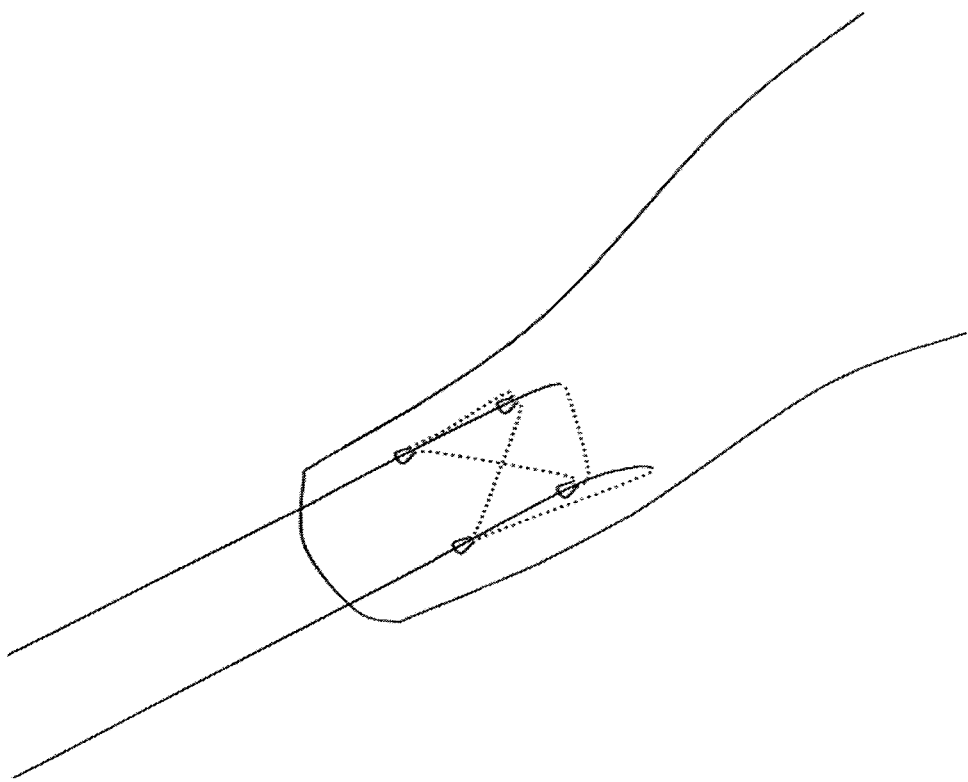

FIG. 11C illustrates another variation of a suture that may be formed with the suture passers described herein, having an extremely low delivery profile, yet able to be attached around the target (e.g., ACL) tissue. In FIG. 11C, two locking loops of suture have been formed then the limbs (legs) have been brought back through centrally, forming a triangular shape. FIGS. 11D and 11E show other variations of locking loop patterns that may be used.

Figure 12A:
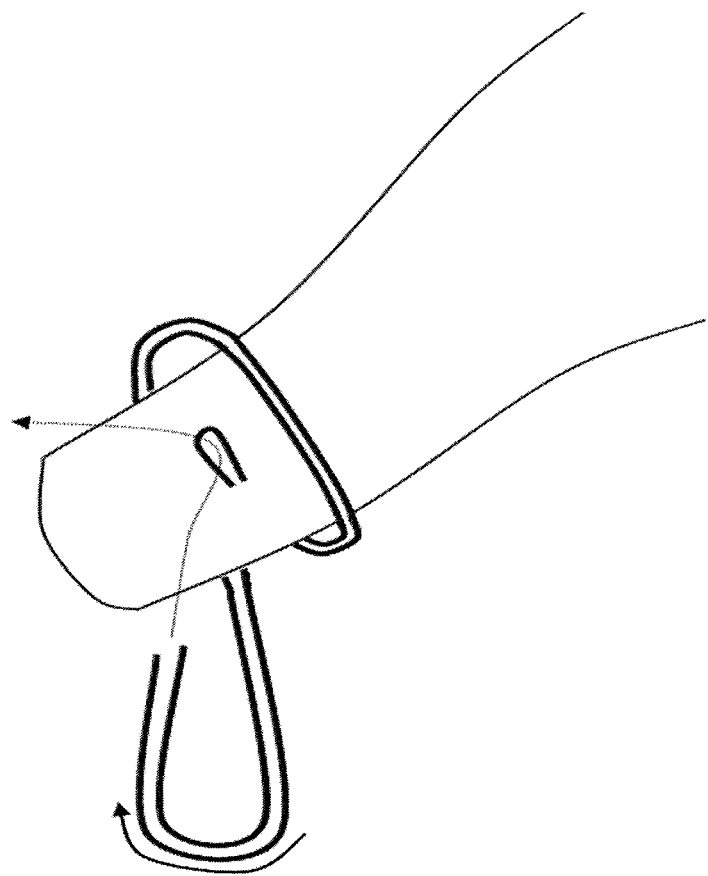
Figure 12C:
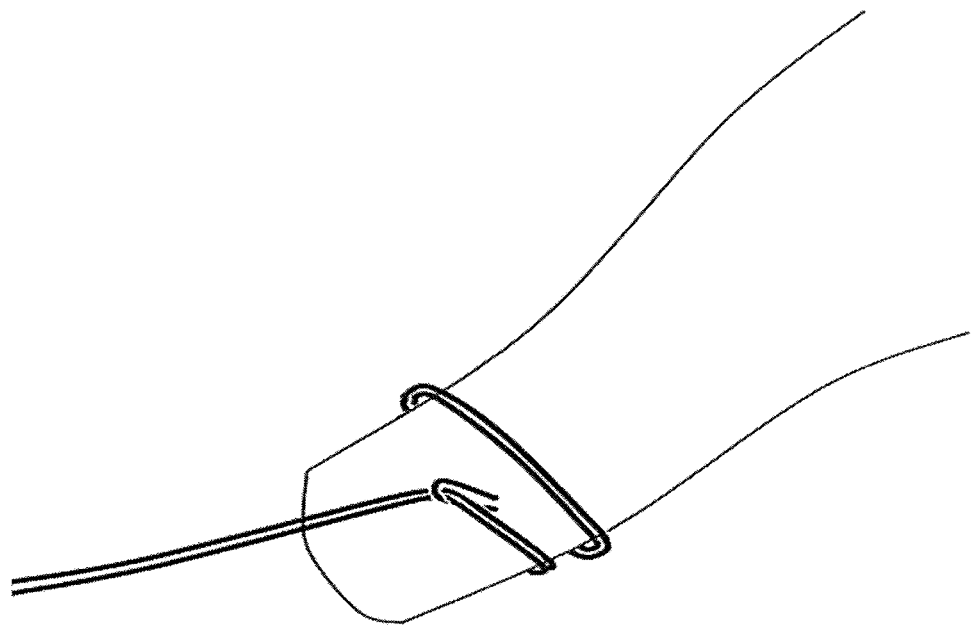
Figure 12B:
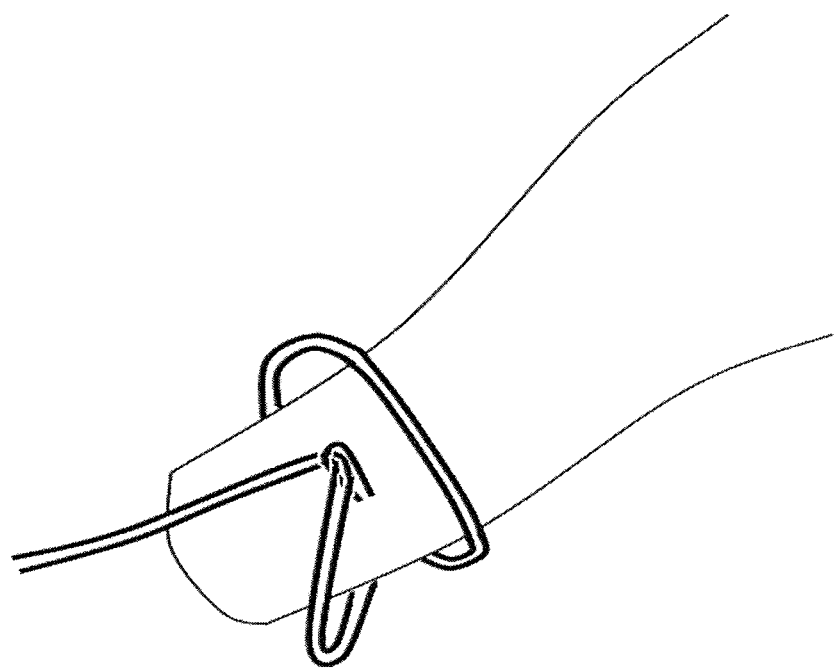

FIGS. 12A-12C illustrate another variation of a locking loop suture pattern in which a central loop of suture (as shown in FIG. 12A) is first passed through the ACL, and the legs of the suture (first and second legs) are wrapped around the tissue (in FIG. 12B) before being passed through the loop and drawn to tighten the loop as shown in FIG. 12C.

Also, in some methods, including methods of repairing ACL, meniscus and other tissues, multiple loops of the length of suture may be passed, and one or both proximal and distal ends (distal leg region/proximal leg regions) may be passed through these loops to form more complex locking patterns, as suggested by FIG. 11E.

Suture Passers

In general, the suture passers described herein may be used as a low-profile suture passer that can be arthroscopically inserted into a very tight (e.g., congested) region and positioned around a target tissue to pass a suture from one side of the tissue to another side, as illustrated above. The suture passer devices described herein may be referred to as suture passers and/or suturing devices. Different variations of the devices described herein may also be referred to as snake-tongue, sigmoidal, dual deployment suture passers, and/or clamping/sliding suture passers.

Figure 13:
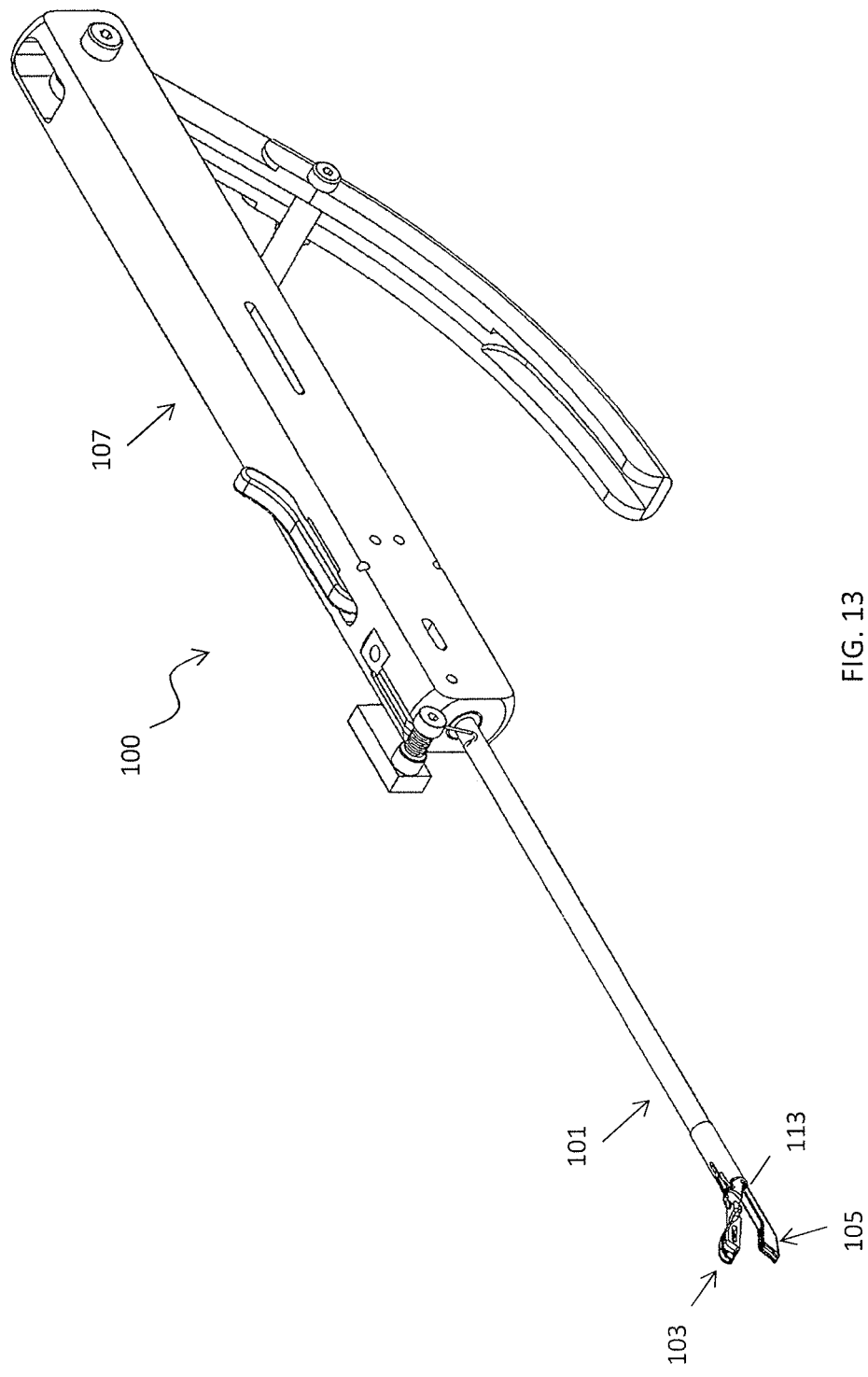
FIG. 13 shows one variation of a dual deployment suture passer as described herein.

In general, the suture passers described herein include a first jaw member and second jaw member that extend from the end of an elongate body region to form a distal-facing mouth into which tissue to be sutured fits. In some variations one or both jaws forming the mouth may be independently moved. FIG. 13 illustrates one variation of a dual deployment suture passer 100. In this example, the device has a first (upper) jaw member 103 extending distally from the distal end of a more proximal elongate member 101. A second jaw member 105 is shown extended distally beneath the first jaw member 103. A handle 107 is located at the proximal end of the device and includes multiple controls for independently controlling the movements of the first jaw member, second jaw member, and tissue penetrator. The handle in this example also includes a second jaw member lock for locking/unlocking the movement of the second jaw member.

The suture passer shown in FIG. 13 is positioned with the first jaw member held at an angle relative to the long axis of the proximal elongate member. The first jaw member in this example is shown having a hinge region 113 about which the first jaw member may be angled relative to the elongate member. In some variations this hinge region is a pinned hinge; non-pinned (e.g., living hinges) regions may be used. Any appropriate articulating region that allows the first jaw member to move at an angle relative to the proximal portion of the device (e.g., the elongate member) may be used. In some variations this first jaw member is referred to as an upper jaw member, but alternative variations (in which the first jaw member is a lower jaw member) are also possible.

The first jaw member may be actuated by any appropriate mechanism, including a tendon member (e.g., push rod, pull rod, or the like), and may be held (locked) at any angle (e.g., between about 0° and 90°, between about 0° and 60°, etc.). In some variations the device has a neutral position during which no force is applied to the controller to move the first jaw member, so that the first jaw member is angled "open" (e.g., at 30°, 45°, 50°, 90° or at any angle between about 15° and about 90°) relative to the elongate body; actuating the control on the handle results in the first jaw member moving towards the "closed" position (e.g., reducing the angle with respect to a line extending from the distal end of the elongate body). In some variations the jaw member is in the neutral position when angled with 0°/180° relative to the elongate body.

The first jaw member shown in FIG. 13 also includes a suture retainer region near the distal end (described in greater detail below). This suture retainer region may hold the suture or be configured to hold a suture. In some variations the suture retainer includes a channel or guide for holding the suture in a preferred position. In some variations the suture retainer includes a pair of graspers, or deflectable members into which the suture may be pushed and held (e.g., handed off from the tissue penetrator). A suture retainer generally holds the suture so that it can be either removed by the tissue penetrator, or so that a suture can be passed into the suture retainer from the tissue penetrator. In FIG. 13, the suture retainer is a channel across which the suture extends so that it can be reliably engaged and pulled down by the tissue penetrator as described in more detail below. In some variations the second jaw member includes a suture retainer, rather than the first jaw member.

The second jaw member is shown in FIG. 13 as a lower jaw member. In this variation, the lower jaw member is configured to slide proximally towards and into the proximal elongate body of the device. The second jaw member typically moves axially, in the direction of the proximal-distal axis of the suture passer. In some variations the second jaw member moves axially completely past the distal end of the elongate body; alternatively, the second jaw member slides axially in the proximal direction only partially (e.g. to align with the hinge region of the first jaw member). The second jaw member shown in FIG. 13 retracts completely into, and extends out of, the lower portion of the elongate body. In some variations the second jaw member moves axially in parallel with the lower jaw member, or only a portion of the lower jaw member extends into the elongate body.

A tissue penetrator (not shown in FIG. 13) may be housed within either the first or second jaw member. As described in more detail below, the tissue penetrator may be configured as a needle, wire, knife, blade, or other element that is configured to extend from within either the first or second jaw members and across the opening between the jaw members to engage a suture retainer and either drop off or pick up a suture therefrom. In general, the tissue penetrator may be configured to completely retract into the jaw member housing. It may be extended across the opening between the jaws by actuating a member in the handle to push or otherwise drive it across the opening, and though any tissue held between the jaws.

The second jaw member 105 shown in FIG. 13 completely houses the tissue penetrator and includes a deflection region that drives the tissue penetrator up and out of the second jaw member by deflecting it across the opening between the two.

The elongate body 101 shown in FIG. 13 is illustrated as a relatively straight cylindrical body, though other shapes may be used. For example, the elongate body may be curved, bent, or angled. In some variations the elongate body is configured to be bent, curved or angled dynamically (e.g. by changing the bend or curve).

The elongate body may be any appropriate length. For example, the elongate body may be between about 6 and about 24 inches long, e.g., 6 inches long, 8 inches long, 10 inches long, 12 inches long, etc. The suture passers described herein may be used for arthroscopic surgeries and therefore may be dimensioned for use as such. Thus the diameter of the device may be configured to be small enough for insertion into a cannula, tube or the like for insertion into the body.

FIGS. 14A-14D illustrate one variation of the distal end region of a dual deployment suture passer forming a distal-facing opening and extending a tissue penetrator across the distal opening. For example, in FIG. 14A the distal end of the device is shown with the first jaw member 201 (shown here as an upper jaw member) extended distally at 0° relative to a line extending from the distal end of the elongate body 203. This "straight" configuration may be helpful for inserting and/or removing the distal end of the device into the tissue (e.g., through a cannula). The first jaw member can then be bent, or allowed to bend in some variations, at an angle relative to a line extending from the distal end of the elongate body.

Figure 14A:
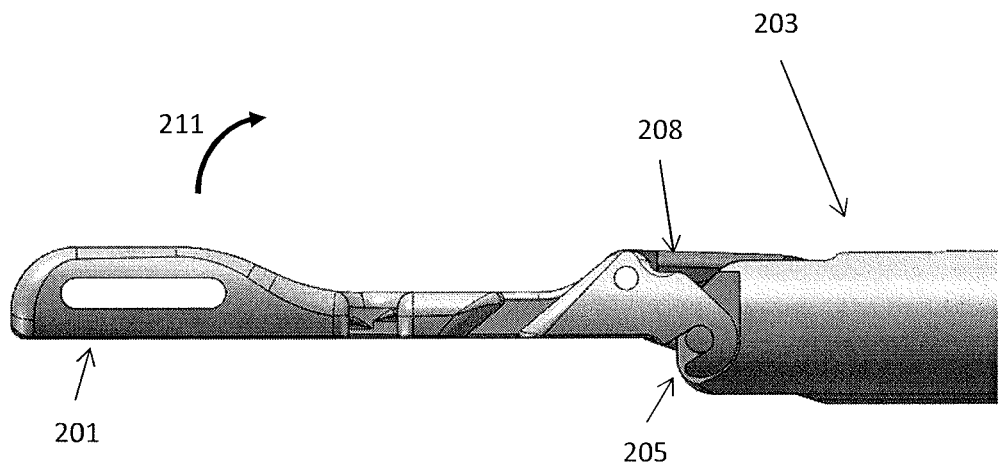
FIGS. 14A-14D illustrate actuation of the first jaw member, second jaw member and tissue penetrator for one variation of a suture passer.

In this example, the first jaw member pivots around a hinge point 205, and is controlled by a pulling member 208 that pushes and/or pulls proximally and/or distally to control the bend of the first jaw member. The pulling member may include a shaft, wire, tendon, tube, cannula, or the like, and may extend to the proximal end of the device where it can be controlled. The arrow 211 in FIG. 14A illustrates the plane and direction of motion of the first jaw member.

Figure 14B:
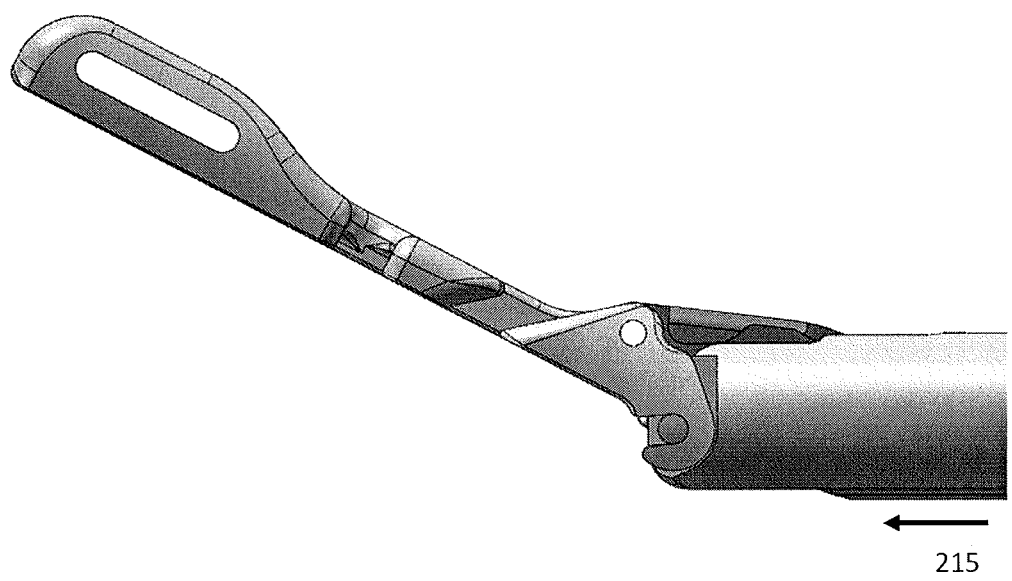
Figure 14C:
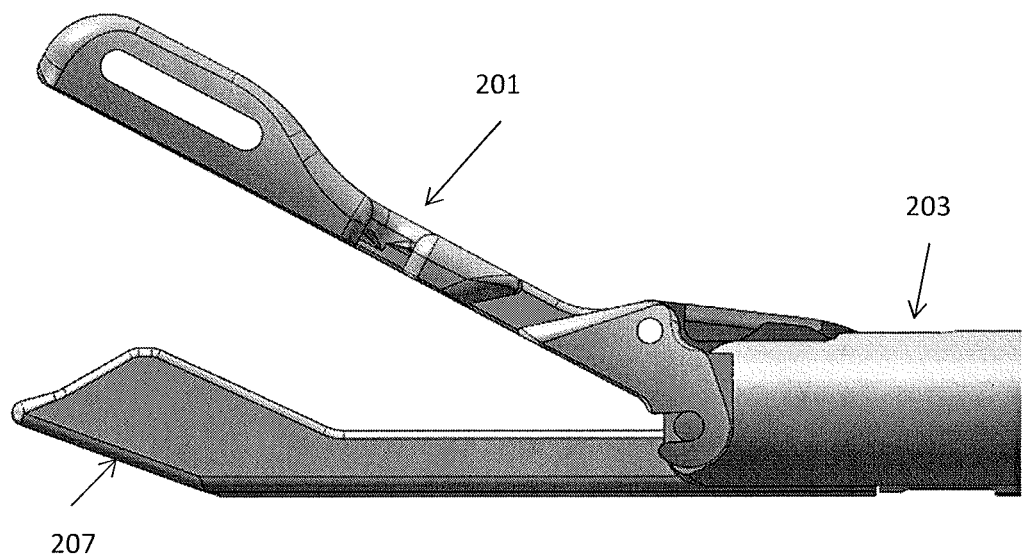

In FIG. 14B the first jaw member has been moved (or allowed to move) so that it forms an angle of approximately 30° with a line extending from the distal end of the elongate body. The arrow 215 in FIG. 14B illustrates the direction of axial motion that the lower jaw (not yet visible in FIG. 14B) will be moved. This is illustrated in FIG. 14C, in which the lower jaw member 207 has been extended distally from the proximal region of the device. In this example the second jaw member 207 is shown fully extended distally relative to the elongate body region 203. Although this example shows the second jaw member extending from completely within the elongate body region (as in FIG. 14B), in some variations the lower jaw member is held outside of the elongate body region, or only partially within the elongate body region. In some variations the second jaw member is completely retracted proximally so that much (or all) of the second jaw member is held proximal to the distal end of the elongate body region 203.

Figure 14D:
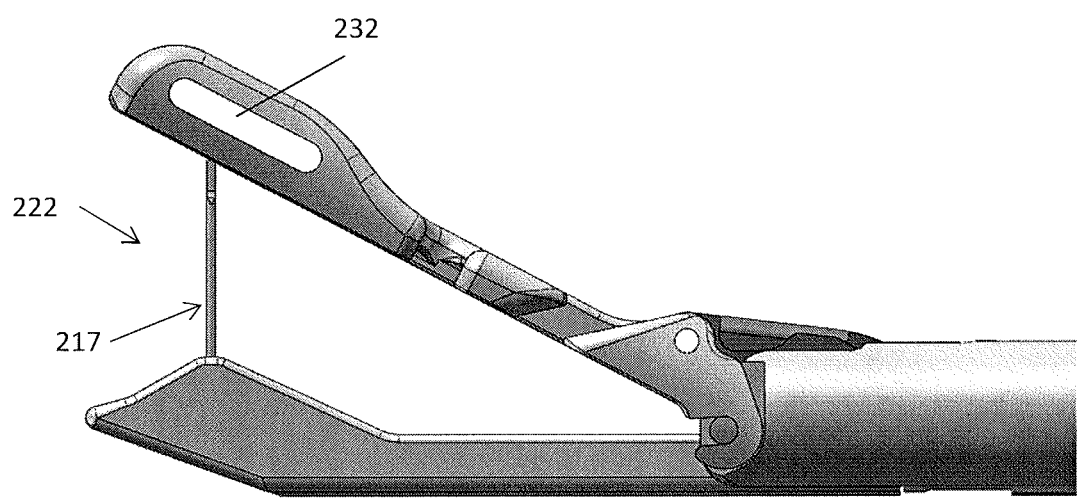

Once the first and second jaw members are completely extended distally (as shown in FIGS. 14C and 14D, the tissue penetrator may be sent across the distal-facing opening 222 as shown in FIG. 14D. Although (as described in greater detail below) in some variations the distal end of the tissue penetrator may be configured to extend distally from an opening in a jaw member, in other variations, the tissue penetrator may be prevented from exiting the opposite side of the jaw member. For example, the tissue penetrator may be prevented from extending distally beyond the jaw member by a limiter (e.g., a travel limiter and/or a movement limiter). In FIGS. 14A-14D the first jaw member includes a cage or shield region 232 that prevents the tip of the tissue penetrator from extending out of the first jaw member where it may cut or damage the non-target tissue. In some variations the device may also include a movement limiter, which limits the movement of the tissue penetrator so that it can only extend to just couple with the opposite jaw member (and pass or grab a suture held therein). Since the jaws may be open to varying positions, a movement limiter may help prevent the tissue penetrator from overextending even when the first jaw member is only slightly angled with respect to a line extending from the distal end of the elongate body.

In some variations the tissue penetrator may be prevented from extending across the opening between the first and second jaw members unless the second (axial moving) jaw member is extended distally relative to the elongate body. This may allow the tissue penetrator to mate properly with the suture engagement region on the first jaw member. For example, a lock or other mechanism may be used to prevent the tissue penetrator from engaging with a control at the proximal end of the device until the second jaw member is fully extended.

Figure 15:
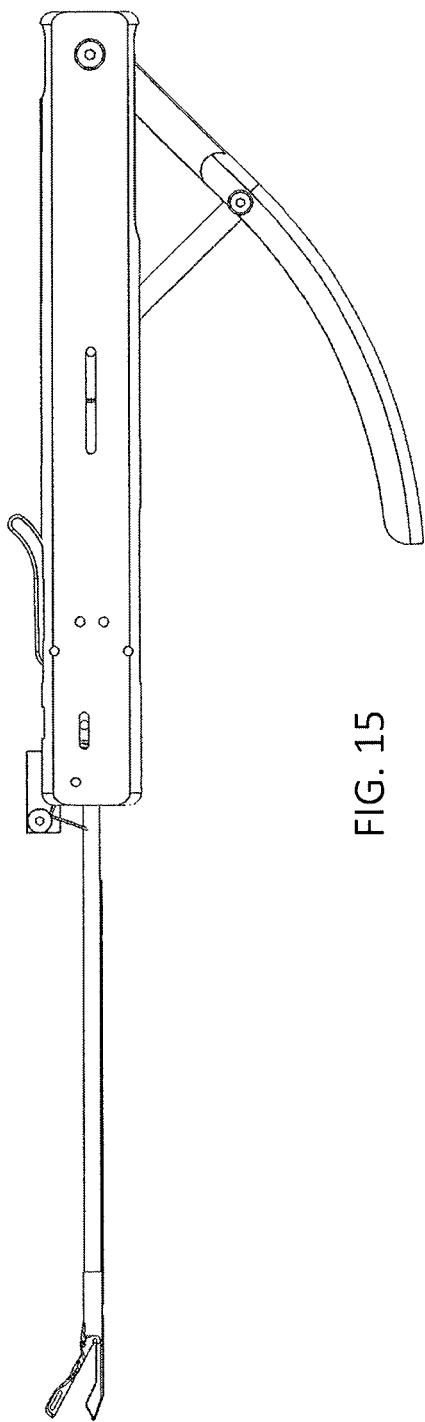
FIG. 15 is a side view of the suture passer shown in FIG. 13.

A side view of the device shown in FIGS. 13-14D is provided in FIG. 15.

Figure 16:
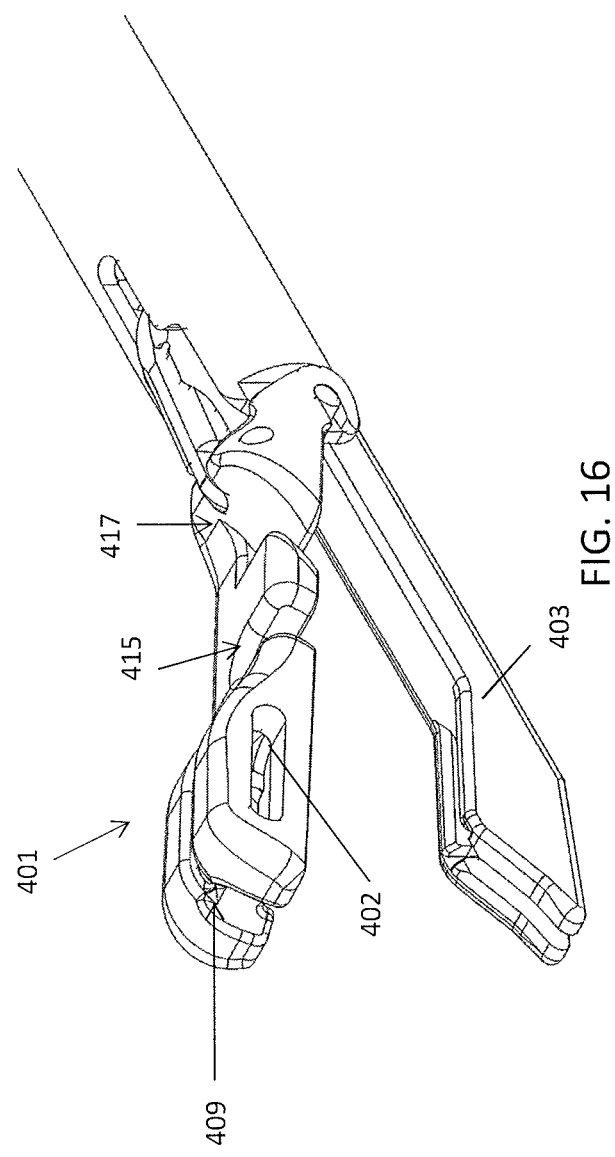
FIG. 16 is a front perspective view of the suture passer shown in FIG. 15 in which the first jaw member is positioned at an angle relative to the longitudinal axis of the elongate body of the device, and the second jaw member is extended fully distally relative to the elongate body to form a distal-facing jaw opening.

FIG. 16 shows a front perspective view of the distal end region of the device of FIGS. 13-15 with the second jaw member extended fully distally and the first jaw member angled slightly (e.g., approximately 30° relative to a line extending distally from the longitudinal axis of the elongate body). In this variation the lower jaw member 403 may be configured to fit within the upper jaw member 401 when the two jaw members are closed down on one another (not shown). Thus the upper (first) jaw member 401 is wider than the lower (second) jaw member 403. The first jaw member in this example also includes optional side windows 402. The first jaw member may also include a suture engagement region; in FIG. 4, this suture engagement region includes a channel 409 through the midline (extending proximally to distally) and a first 415 and second 417 notch or protrusion cut into the first jaw member. A suture may be wrapped around the first jaw member by passing from the proximal end of the device, under the proximal notch 417 and along the bottom (e.g., the side of the first jaw facing the extended second jaw) around the distal end of the first jaw member and along the top (e.g., the side of the first jaw facing away from the second jaw) and, under the distal notch 415 and back up out of the proximal notch 417 so that the suture may extend distally. This loop of suture held by the suture engagement region of the jaw member may be held under sufficient tension so that the suture may be engaged by the suture engagement region of the tissue penetrator (e.g., hook, grasper, etc.). In some variations a tensioning member may be included in the suture engagement region.

In some variations (not shown here) the suture may be contained within the elongate body of the device. Alternatively, the suture may be kept outside of the device. In some variations the suture may be loaded by the user. For example, a user may load a suture on the device by placing a loop of suture over the first jaw member. In some variations the suture holder may be placed along the length of the device to hold or manage the suture so that it doesn't interfere with the operation of the device or get tangled.

Figure 17A:
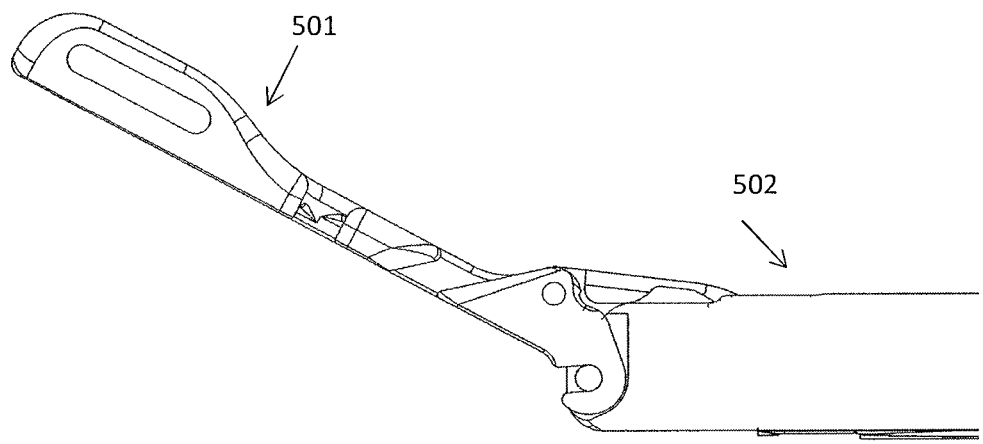
FIG. 17A is a side perspective view of the suture passer variation shown in FIG. 16 with the second jaw member retracted proximally.
Figure 17B:
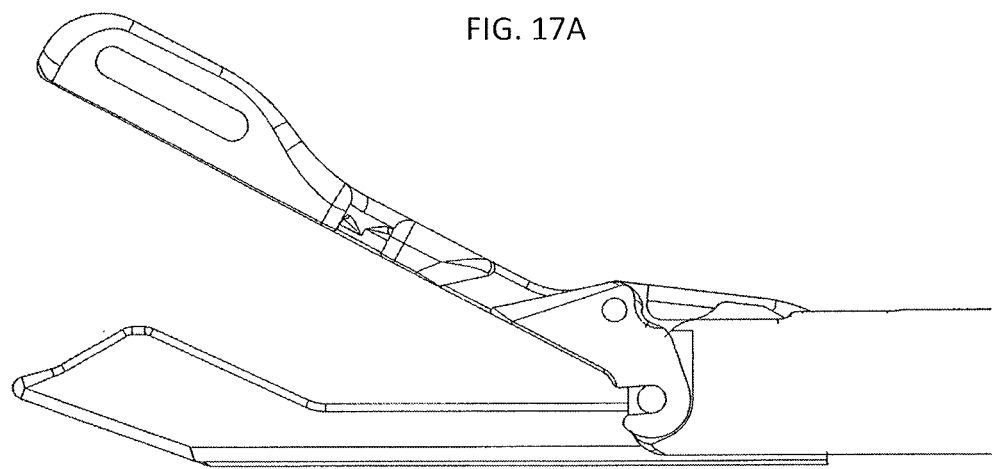
FIG. 17B shows the suture passer of FIG. 17A with the second jaw extended distally.
Figure 17C:
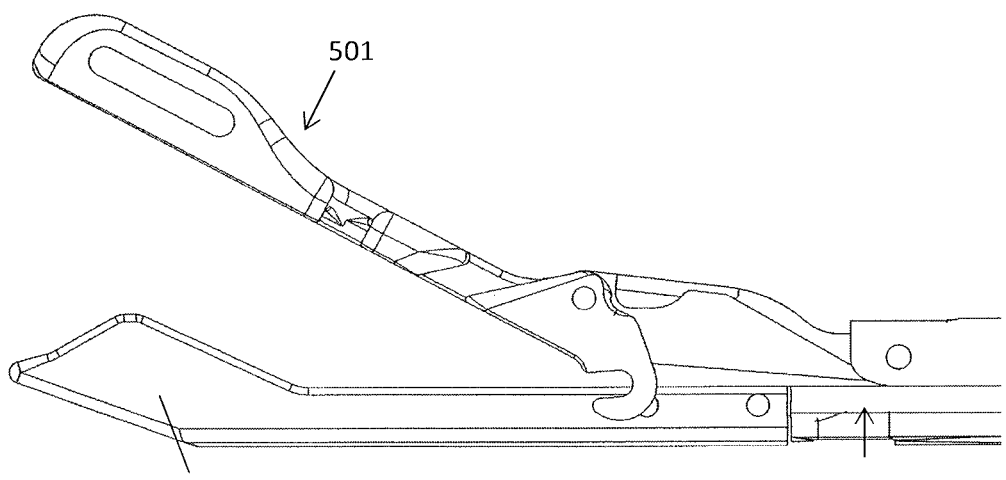
FIG. 17C shows FIG. 17B with the outer region of the elongate body removed.
Figure 18A:
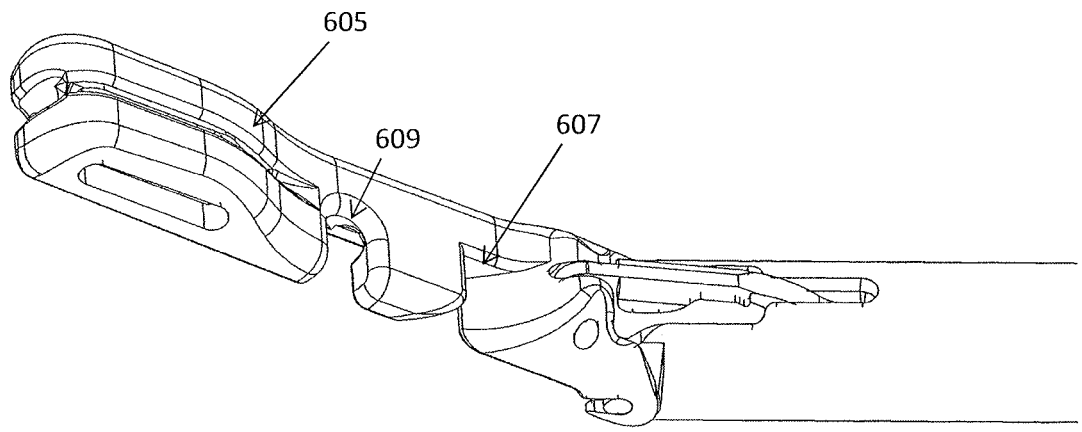
FIG. 18A shows a top perspective view of the suture passer shown in FIG. 17A.

FIGS. 17A-17C and 18A-18C illustrate different views of the first and second jaw members in one variation. For example, in FIG. 17A the first jaw member is shown with the second jaw member retracted proximally. FIG. 18A shows a top perspective view of the same first jaw member shown in FIG. 17A. In FIG. 18A, the first jaw member includes a channel 605 extending along the longitudinal length of the first jaw member; this channel may form part of the suture engagement region. The channel may hold the suture so that it extends along the midline of the first jaw member on the underside of the first jaw member. The notches 607, 609 in the first jaw member near the proximal end extend toward the midline of the first jaw member and allow the suture to pass from the top of the first jaw member to the bottom and back out, as discussed above. Thus, the suture may be held close to the elongate body of the device even when the first jaw is open to various angles.

Figure 18B:
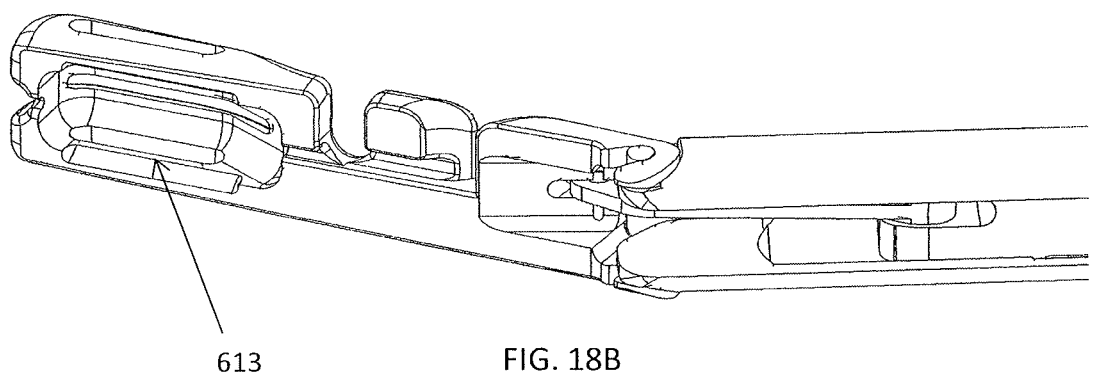
FIG. 18B shows a bottom perspective view of the suture passer of FIG. 17B.
Figure 18C:
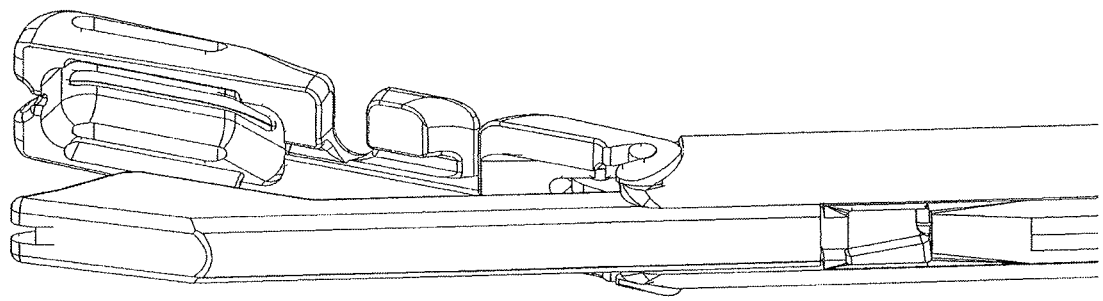
FIG. 18C shows a bottom perspective view of the suture passer of FIG. 17C.

FIG. 18B illustrates the underside or bottom of the first jaw member shown in FIG. 18A. The suture management region is the entire opening formed at the distal end. This cavity 613 is surrounded by the inside of the first jaw member, and (as mentioned above) may act as a limiter to limit the tip of the tissue penetrator from extending outside of the first jaw member. FIG. 18C shows the same view as in FIG. 18B, but with the second jaw member axially extended distally.

Returning now to FIG. 17B, a side view of the distal end of one variation of a suture passer is shown with the second jaw member extended distally. FIG. 17C shows the same view as in FIG. 17B but with the outer cannula covering for the elongate member removed, showing the connection between the second jaw member and the pushing/pulling element (rod 505). The pushing/pulling element may be a wire, shaft, tendon, or the like, allowing the second jaw member 503 to be controllably slid distally and proximally.

Not visible in FIGS. 17A-18C is the tissue penetrator, which is fully retracted into the second jaw member in this exemplary embodiment.

FIG. 19A shows one variation of a tissue penetrator 700 as described herein. In this example, the tissue penetrator includes a sharp, pointed distal tip 701 and just proximal to the distal tip is a suture engagement region configured as a hooked cut-out region 703. The proximal end of the tissue penetrator includes a coupling region for coupling the tissue penetrator with a pusher/puller mechanism, such as a shaft, rod, wire, tendon, or the like.

FIG. 20 shows the same perspective view of FIG. 16, but with the tissue penetrator 805 partially extended across the distal-facing opening formed between the first jaw member 801 and the second jaw member 803. A suture 808 is looped around the first jaw member 801. Both ends of the suture pass into the notched region and are held close to the elongate body, allowing the loop of suture to be held in tension within the suture engagement region.

Figure 21A:
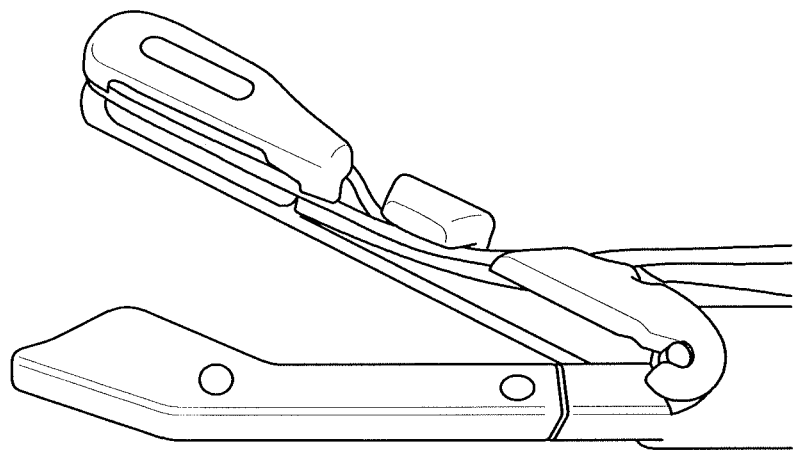
FIGS. 21A-21C illustrate actuation of a suture passer such as the one shown in FIG. 20 to pass a suture from the upper jaw to the lower jaw.
Figure 21B:
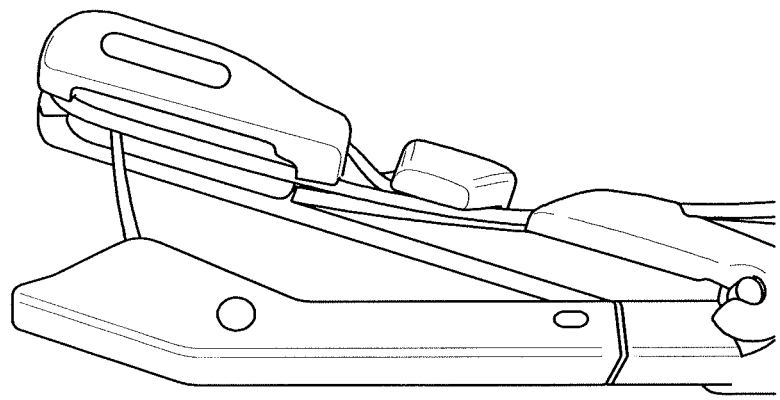
Figure 21C:
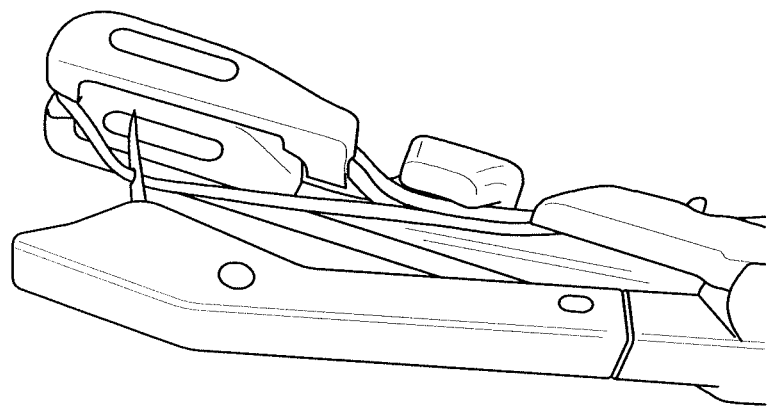

FIGS. 21A-21C illustrate the variation of the device described above passing a suture from the first jaw member to the second jaw member. In FIG. 21A, the distal end of the second jaw member for the dual deployment suture passer has been extended fully. The upper jaw is held at an angle relative to the elongate body region of the device proximal to the joint (e.g., hinge, bend region, etc.) of the first jaw member. A suture has been loaded into the suture engagement region, and extends along the length of the midline of the first jaw member. In FIG. 21B, the first jaw member has been moved slightly (decreasing the angle between the first jaw and the fully extended lower jaw member). This may be typical of situations in which tissue is held between the first and second jaw members. Clamping the tissue to be sutured in this manner allows the tissue to be secured within the jaws, preventing it from moving undesirably, and helping the tissue penetrator to penetrate through the tissue. Further, in FIG. 21B the tissue penetrator has been extended from the lower second jaw member across the distal-facing opening, towards the first jaw member and the suture retained therein. Once the tissue penetrator contacts the suture, it may be grabbed or otherwise engaged by the suture engagement member of the tissue penetrator. Thereafter, the suture can be pulled back down with the tissue penetrator as it retracts back into the second jaw member. In this variation, the loop of suture is pulled back through the tissue.

Although the variation of the suture passer shown and discussed above includes relatively straight first and second jaw members, other configurations of jaw members are possible. For example, FIGS. 22A and 22B illustrate two variations of the upper jaw member. In particular, FIG. 22B shows a variation in which the straight jaw member of the first jaw member is instead a curved jaw member; the curve may allow a greater thickness of tissue to be placed between the jaws and may also be useful for navigating certain tissue regions, such as the labrum and ACL.

In general, the first jaw member in many of the variations described herein may be dynamically angled with respect to the elongate body of the device. The first jaw member may be connected to and extend from the distal end of the elongate body, or may be connected to an intermediate region between the elongate body and the first jaw member.

Figure 23A:
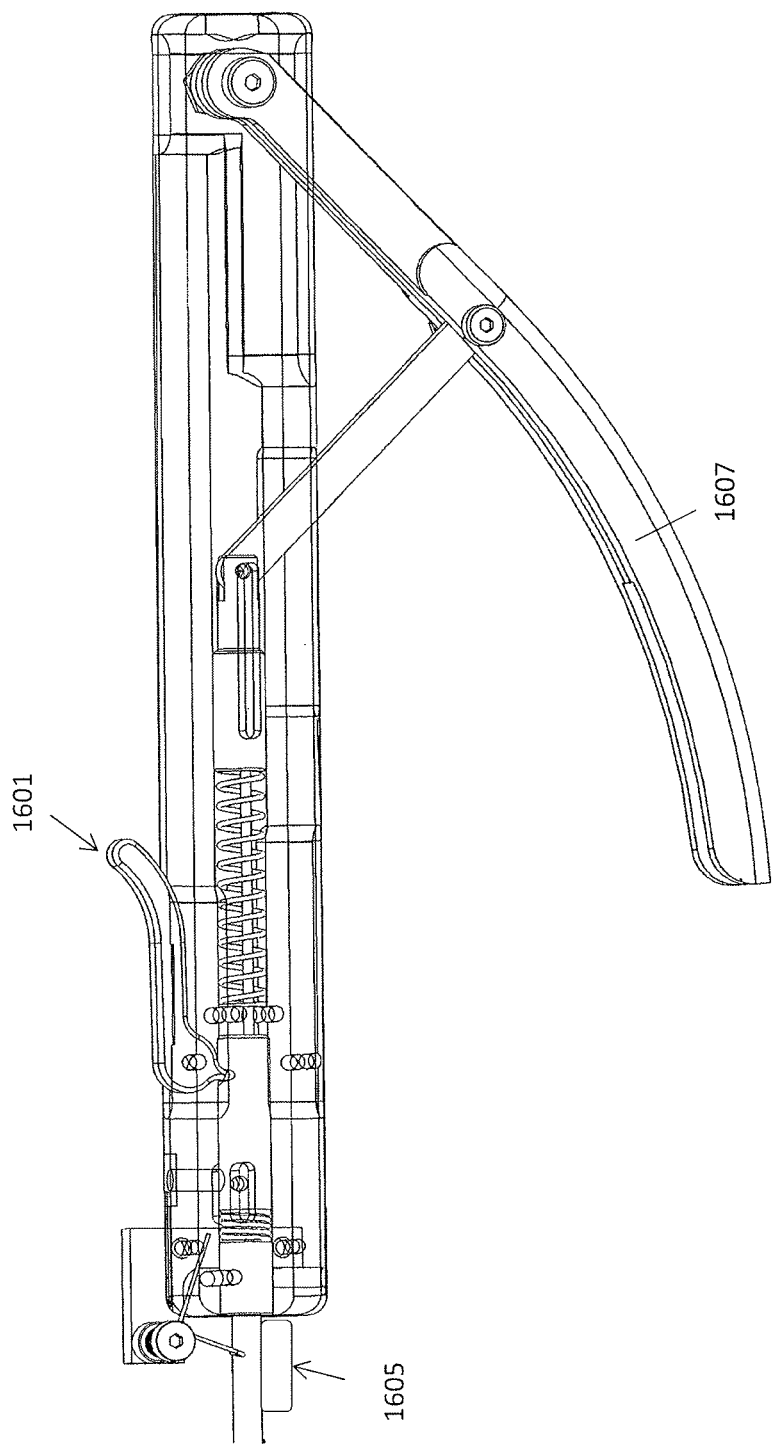
FIG. 23A shows one variation of a proximal handle with controls for controlling action of a dual deployment suture passer.

The position of the first jaw member and the second jaw member may be separately and/or independently controlled. For example, any of the variations described herein may include a proximal handle having controls for controlling the activation of the first jaw member, the second jaw member, and the tissue penetrator. For example, FIG. 23A is an enlarged view of the handle region of the suture device discussed above in FIGS. 13-15. In this example, the handle includes a control to control the motion of the first jaw member (which may also be referred to herein as a clamp trigger), a second jaw member control 1605 (or lower jaw handle), and a tissue penetrator control 1607 (or needle trigger). Additional controls may include a lower jaw screw lock to lock the position of the lower jaw member. The operation of this handle variation in controlling a dual deployment suture passer is described below with respect to FIGS. 25A-25F.

Figure 23B:
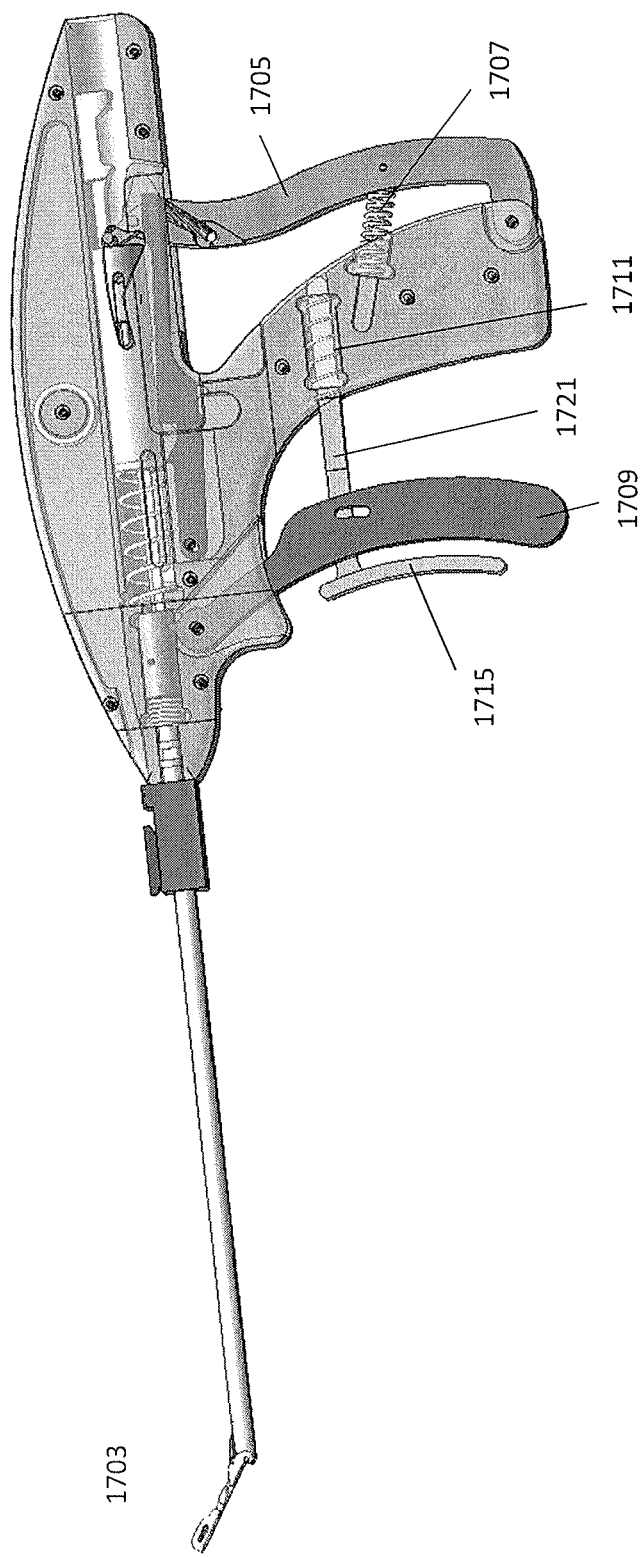
FIG. 23B shows another variation of a proximal handle with controls for controlling action of a dual deployment suture passer.

FIG. 23B illustrates another variation of a handle for a dual deployment suture passer. In this variation the handle controls are triggers/handles. The proximal trigger 1705 is a squeeze handle that controls the angle of the first jaw member relative to the elongate body. The control and handle are configured with a bias element (spring 1707) that tends to keep the first jaw member at an angle with respect to the elongate member; in this example, the angle is about 30° relative to a line extending distally from the long axis of the elongate body region of the device. A second grip control 1709 controls the extension of the second (lower) jaw member (not visible in FIG. 25B). In this variation a second biasing element (spring) 1711 tends to hold the control so that the second jaw element is retracted proximally and, in this example, into the elongate member. A third trigger control 1715 controls the extension of the tissue penetrator. This control is arranged to include a lock that prevents the control from engaging with the tissue penetrator until the second jaw member is completely extended. Further, the control also includes a travel limiter 1721 that limits how far the tissue penetrator may be extended from within the second jaw element based on how angled the first jaw member is, preventing the tissue penetrator from trying to extend beyond the first jaw element.

In any of the devices described herein, the controls may be handles or triggers (as illustrated in FIGS. 23A and 23B) or other controls, such as dials, buttons, sliders, switches, or the like.

Figure 26A:
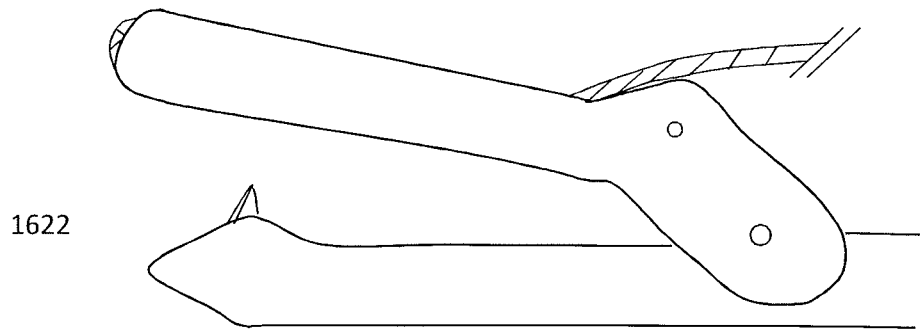
FIGS. 26A-26C illustrate another variation of a dual deployment suture passer configured so that the distal end of the tissue penetrator extends distally from the first jaw.
Figure 26B:
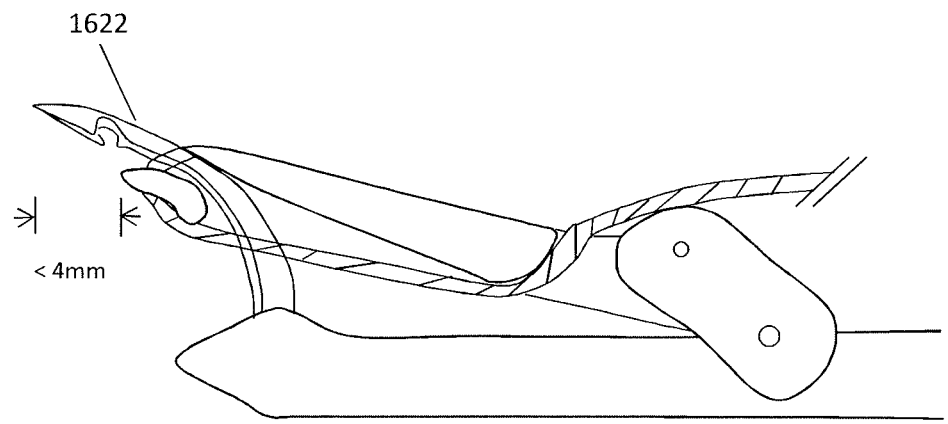
Figure 26C:
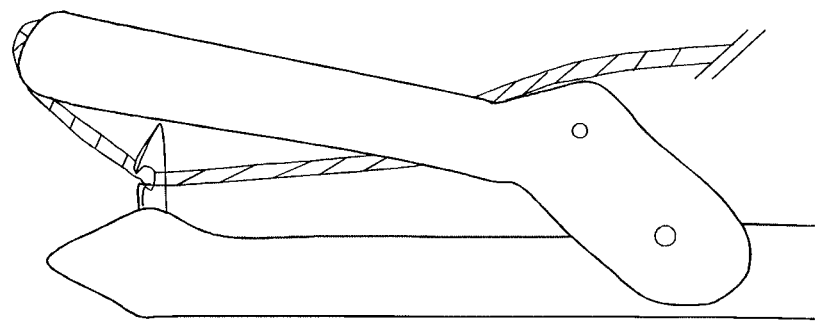

As mentioned above, although many of the suture passer devices (including the dual deployment suture passers described above) limit the travel of the tissue penetrator to prevent it from extending beyond the opposite jaw member from where it is housed when not extended, in some variations it may be beneficial to allow the tissue penetrator to extend distally out of the opposite jaw member, as illustrated in FIGS. 26A-26C. In this example the tissue penetrator is deflected within the opposite jaw member and allowed to extend distally out of the opposite jaw member some amount (e.g., less than 5 mm, about 5 mm, less than 4 mm, about 4 mm as shown in FIG. 26B, less than 3 mm, about 3 mm, etc.). For example, as shown in FIG. 26A, the tissue penetrator may be housed in the second jaw member and may be deployed across the distal-facing opening formed when the first and second jaw members are extended fully distally. The tissue penetrator is shown partially extended from the second jaw member in FIG. 26A, however it should be understood that the tissue penetrator (including the tip of the tissue penetrator) may be fully retraced or retractable into the second jaw member. Also, for convenience in FIGS. 26A-26C, the jaw members are shown close together, e.g., with only a little space between the first and second jaw members; the jaws may be more opened, for example, by moving the first (upper) jaw member at an angle with respect to the more proximal region of the device.

In FIG. 26B the tissue penetrator 1622 extends from within the second jaw and across the distal-facing opening to pass into an opening on the opposite (first or upper) jaw member. The tip of the needle is pointed in this example, and a side region of the needle proximal to the pointed distal tip is recessed to form a suture engagement region that is hook-shaped. Extending the needle into and partially out of the first jaw member as shown in FIG. 26B allows the suture engagement region on the tissue penetrator to engage the suture held by the first jaw member, as shown. The tissue penetrator in this example extends out of the distal end of the first jaw member distally (not laterally) and is limited to extending just a finite amount (e.g., less than 4 mm) from the distal tip of the first jaw member. In FIG. 26C, the tissue penetrator is retracted back to the second jaw member, pulling the suture with it in the suture engagement region.

The variation of the suture passer illustrated in FIGS. 26A-26C in which the tip of the tissue penetrator extends distally, has various features or advantages including simplifying the coordination between the various parts. For example, less coordination is required to limit the needle motion (e.g., stopping it before it crashes into the first or upper jaw). This may allow greater tolerances, and the parts may require less precision. Also, extending the tissue penetrator distally may allow for "over travel" of the tissue penetrator and provide for more reliable engagement (hooking) of the suture by the suture engagement region. The distal end of the first jaw member may include sufficient space for the tissue penetrator to over-travel the suture so that the hook (suture engagement feature) on the tissue penetrator can grab the suture on its way back to the lower (second) jaw member. With this variation, the height of the first jaw member can be compressed sizably, and the over-travel necessary to pick up the suture is directed in a manner that doesn't require additional height. Further, the additional over-travel opportunity offered by this configuration may allow use of a symmetric distal tip region for the suture penetrator, e.g., having a point in the middle of the tissue penetrator distal tip region. Asymmetric tissue penetrators may also be used (e.g., having a point on one side of the tissue penetrator). Other examples of suture passers (including dual deployment suture passers) having tissue penetrators configured to extend beyond the distal end of a jaw member are described and illustrated below, including in FIGS. 27A to 37B.

Figure 24A:
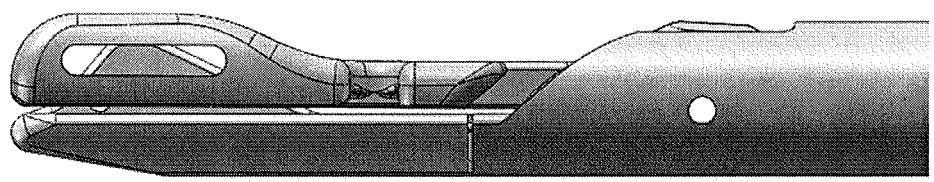
FIGS. 24A-24C show another variation of a suture passer as described.
Figure 24B:
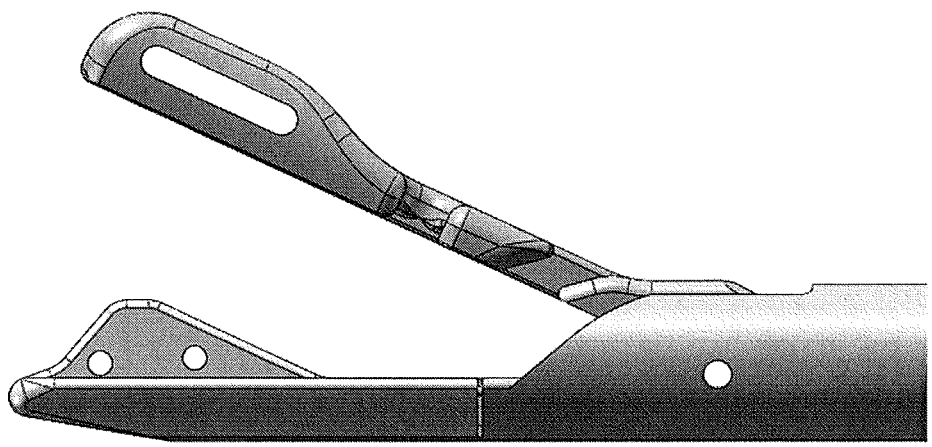
Figure 24C:
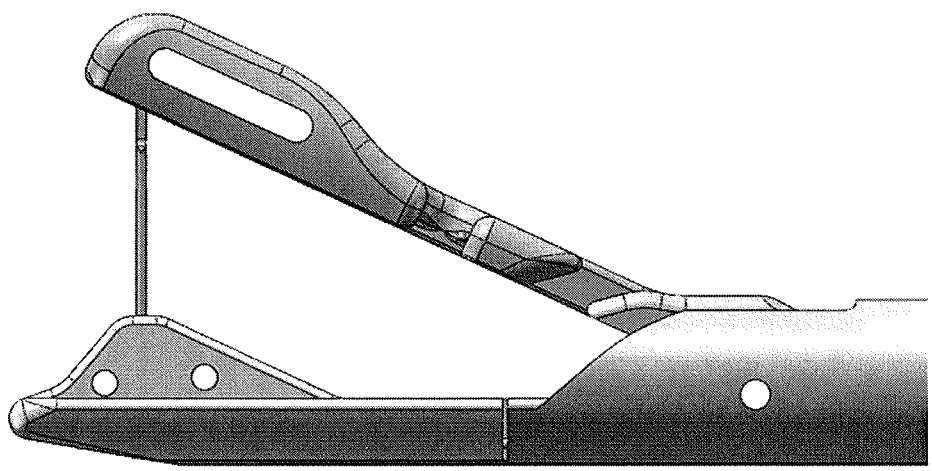

FIGS. 24A-24C illustrate another variation of a suture passer. In FIG. 24A, the second jaw member is not retracted proximally, and the first and second jaw members are clamped together. The first jaw member may be opened as shown in FIG. 24B, and the tissue penetrator may be extended across the distal-facing opening, as shown in FIG. 24C.

In general, the suture passer devices described herein may be used to suture any appropriate tissue. These devices are particularly well suited for passing a suture in a minimally invasive procedure to reach difficult to access regions. Examples of the use of these devices are provided below, and illustrated in FIGS. 25A to 25F.

Figure 25A:
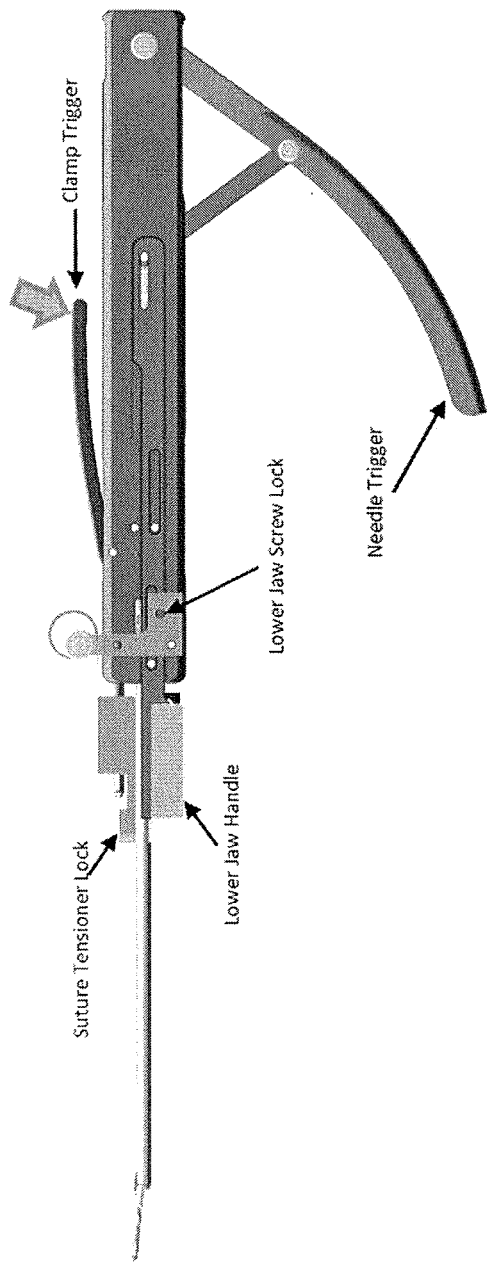

The general operation of one variation of a dual deployment suture passer is illustrated in FIGS. 25A-25F. The clamping/sliding suture passer illustrated in FIG. 25A includes a handle such as the one shown in FIG. 23A, above. Before use, a suture may be loaded on the first jaw member of the device. For example, a loop of suture may be loaded onto the first jaw member. The free ends of the suture may be coupled to a suture control element such as a tensioning screw, as shown in FIG. 25A. For example, the two free ends may be cinched onto a tensioner screw. The suture passer may be loaded outside of the body by the user, or it may be pre-loaded. Once loaded, the suture passer may be inserted into the body near the target tissue. For example, the device may be inserted into the body through a cannula. As shown in FIG. 25A, the second (lower) jaw member may be fully retracted proximally, and the upper jaw may be clamped down fully so that it is in-line with (straight) relative to the elongate member; the first jaw member may be locked in this position for insertion, or it may be moved or dynamically adjusted as it is inserted.

Figure 25B:
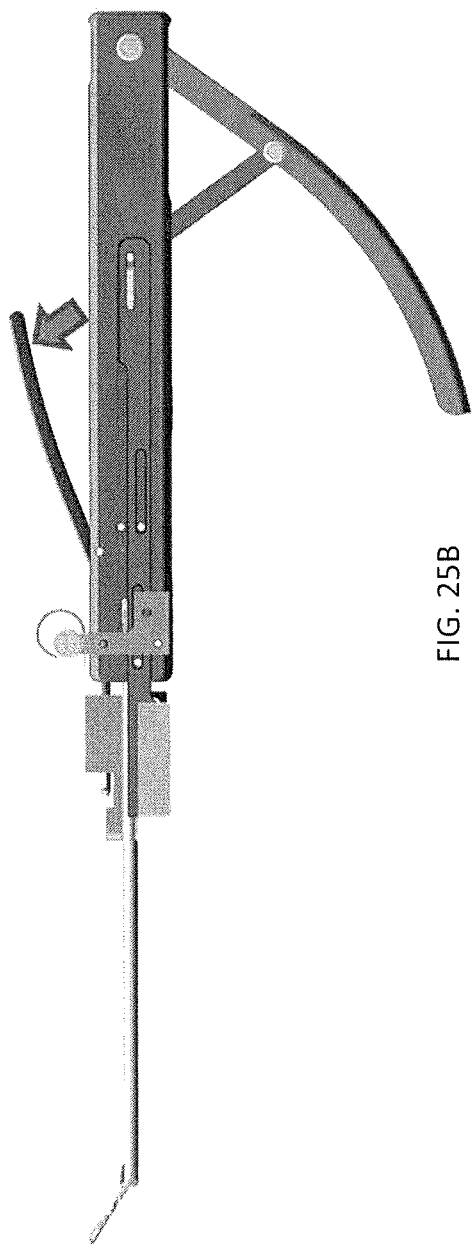

Thereafter, the device may be positioned relative to the target tissue. For example, the first jaw member may be positioned adjacent to the target tissue. As shown in FIG. 25B, the device may then be positioned and the clamp trigger adjusted or released.

Figure 25C:
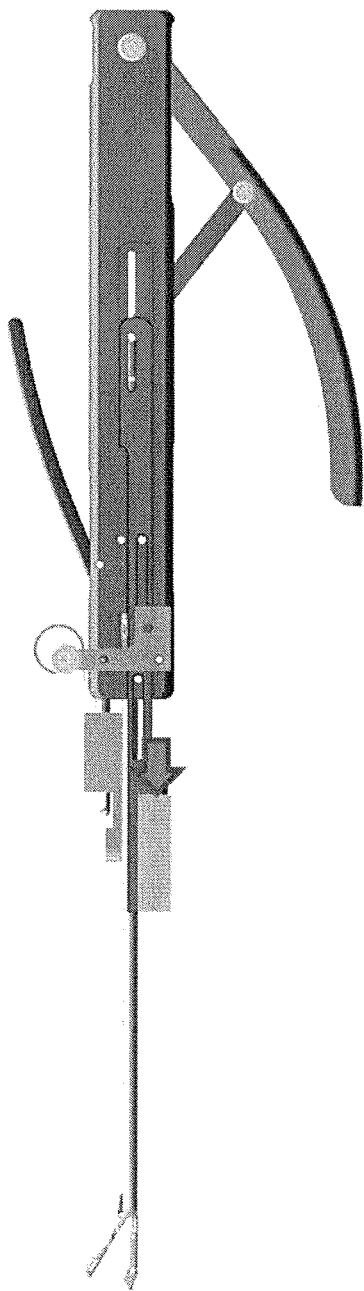

Once the tissue is adjacent to the first jaw member, the second jaw member may be extended to surround a target tissue, as shown in FIG. 25C. In this example, the control for the second jaw member (the lower jaw lock) may be actuated to slide the lower jaw member distally, forming the distal-facing opening, and surrounding (at least partially) the target tissue to be sutured. As shown in FIG. 25C, this may be achieved by sliding in and locking the lower jaw with the lower jaw handle by releasing the lower jaw screw lock and sliding the lower jaw into position. The lower (second) jaw may then be locked in a fully extended position.

Figure 25D:
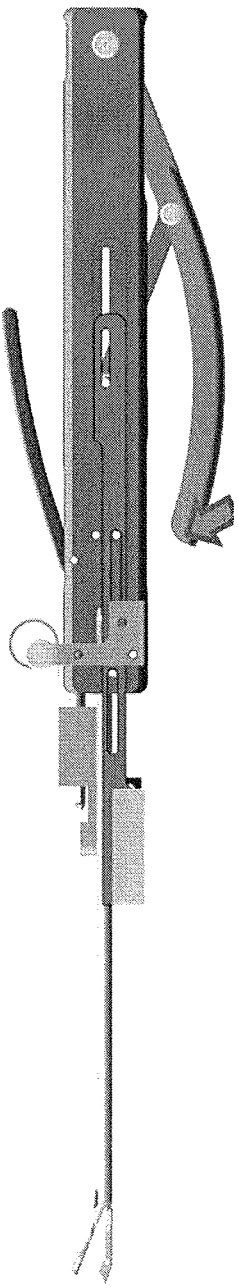

The upper (first) jaw member may be adjusted to clamp or hold the target tissue securely between the upper and lower (first and second) jaw members, as illustrated in FIG. 25D. Thereafter, the tissue penetrator may be actuated (e.g., by squeezing the needle trigger) to extend from within the lower jaw member, through the tissue between the first and second lower jaw members, and across to the upper jaw. To engage a suture held within the suture engagement region in the upper jaw. The tissue penetrator may then pick up the suture from the upper jaw and pull it back down through the tissue, as shown in FIGS. 25D and 25E.

Once the suture has been hooked, the tissue penetrator may be retraced back into the second jaw member (in this example), as shown in FIG. 25F, and the lower jaw member may be retraced proximally, in the reverse to the process described above, so that the suture passer, which having passed the suture successfully, may be withdrawn from the patient.

Sigmoidal Tissue Penetrators

As discussed above, in reference to FIGS. 26A-26C, any of the devices described herein may be configured so that the tissue penetrator may extend distally from the distal end of one of the jaw members. Thus, in some variations, a tissue penetrator includes a mouth that opens in a distal-facing direction. The mouth is formed from a first jaw (e.g., upper jaw) and a second jaw (e.g., lower jaw); the tissue penetrator may extend between the first and second jaw in an approximately sigmoidal pathway. This is illustrated in FIGS. 27A-27C.

FIGS. 27A-27C show a schematic of one variation of a tissue penetrator having a distal-facing mouth 3201. The tissue suture passer has been made semi-transparent to show the tissue penetrator 3203 within the lower jaw member in FIG. 27A. In this example, the suture passer is configured so that the tissue penetrator may be extended distally first (in FIG. 27A) through the lower jaw member 3205 until it is deflected out of the lower jaw and across the distal facing mouth 3201. In this example, the lower jaw includes a deflector 3213 that redirects the tissue penetrator out of the lower jaw and towards the upper jaw, as shown in FIG. 27B. The tissue penetrator may pass through any tissue held within the open mouth 3201, and eventually meet the upper jaw member 3207. Once within the upper jaw member 3207, the tissue penetrator may then be deflected so that it extends distally within the upper jaw member. As shown in FIG. 27C, the tissue penetrator 3203 may be deflected distally by an internal deflector 3209 within the upper jaw member 3207. The tissue penetrator 3203 may extend distally out of a distal opening 3211 at the distal end of the upper jaw member 3207.

Although many of the suture passer variations configured for sigmoidal movement of the tissue penetrator, in which the tissue penetrator extends distally from a jaw member, may be configured as dual deployment suture passers (e.g., in which the two jaw members move independently with different types of motion), suture passers with fixed jaws or suture passers in which only one jaw moves relative to the suture passer may be used. For example, FIGS. 28A-28F show three different variations of suture passers having a distally extending tissue penetrator that travels in an approximately sigmoidal path.

For example, in FIG. 28A the upper and lower (first and second) jaws forming the distal-facing mouth of the suture passer are both movable, as described above for the dual deployment configuration. The tissue penetrator 3304 is shown extending from the lower jaw member 3303, across the distal-facing opening, and into the upper jaw member 3306, where it then extends distally slightly beyond the distal end of the upper jaw 3306. The suture passer of FIG. 28A is also shown in FIG. 28B, illustrating the movement of the upper and lower jaw members. As indicated in FIG. 28B, the upper jaw 3306 can pivot 3315 around a hinge point 3311 at the distal end region of the elongate member 3308. The lower jaw member 3303 can move axially (proximally and distally) 3317 relative to the elongate member 3308.

In FIGS. 28C and 28D, only one of the jaw members (the upper jaw member) may move; the opposite jaw member is fixed. In FIG. 28C, similar to FIG. 28A, the tissue penetrator extends distally from the upper jaw member 3306 out of a distal opening (not shown), along a sigmoidal path. As shown in FIG. 28D, the upper jaw includes a hinge point 3311 so that it can be controllable pivoted 3327 (using a proximal control) to form an angle with respect to the distal end region of the elongate shaft.

In FIGS. 28E and 28F, the upper jaw is shown as fixed (e.g., in a pre-formed bend or angle relative to the distal end of the elongate member) and the lower jaw may be moved axially distally/proximally 3337.

Figure 29A:
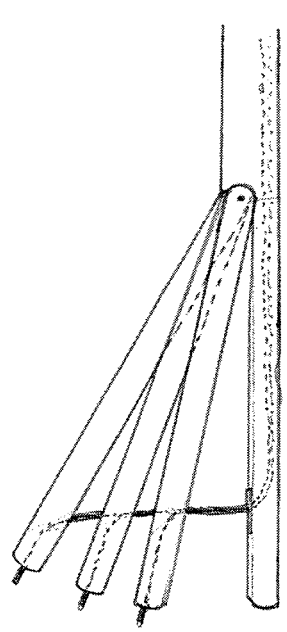
FIG. 29A illustrates different paths for a tissue penetrator in a suture passer having an upper jaw member that pivots.
Figure 30A:
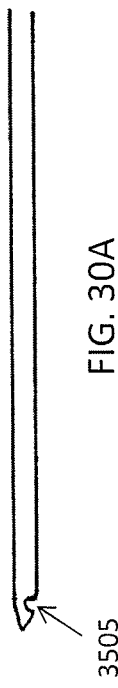
FIGS. 30A and 30B show top and side views, respectively of one variation of a tissue penetrator.
Figure 30B:
Figure 29B:
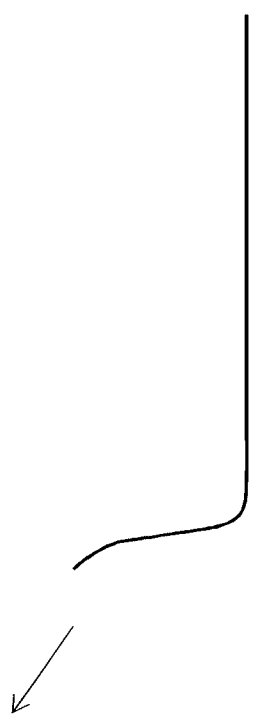
FIGS. 29B-29E illustrate sigmoidal paths that may be taken by a tissue penetrator as described herein.
Figure 29C:
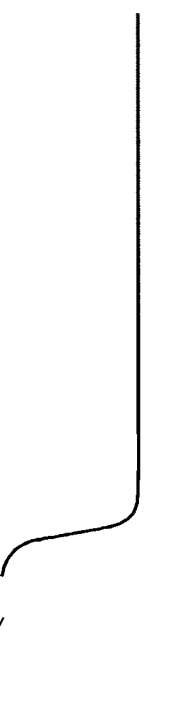
Figure 29D:
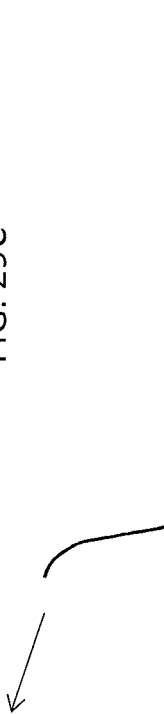
Figure 29E:

The path taken by the tissue penetrator may be approximately sigmoidal, as illustrated in FIGS. 29A-29E. FIG. 29A illustrates the different paths for a tissue penetrator in a suture passer having an upper jaw member that pivots. In any of the angled positions shown the suture passer may take an approximately sigmoidal path. FIGS. 29B-29E illustrate different sigmoidal paths for the tissue penetrator. In general the term sigmoidal path should be understood to be approximately sigmoidal when viewed in profile, as shown in FIGS. 29B-29E. In these examples the distal end of the tissue penetrator may extend distally at approximately the same angle as the upper jaw member (as indicated by the arrows to the left of each of FIGS. 29B-29E), rather than horizontally and parallel to the lower jaw member, as in a completely sigmoidal path. FIGS. 30A and 30B show one variation of a tissue penetrator from a top (FIG. 30A) and side (FIG. 30B) view. The distal end region of the tissue penetrator includes a suture retainer region 3505 configured as a hook.

In general, the needle width may be between 0.1" and 0.02". For example, in some variations the needle is approximately 0.058" in width. The needle may be relatively thin, e.g., having a thickness between about 0.02" and about 0.005". For example, in some variations the needle is approximately 0.0115" thick. In some variations the needle has a thickness of about 0.008". In general, the needles described herein have sufficient column strength to push through the tissue, and can be bent or deflected with sufficiently low force to accomplish the sigmoidal bend described herein; these needles may also have sufficient fatigue life to withstand multiple (e.g., 5×, 10×, 20×) extensions and withdrawals between the upper and lower jaw members and out of the distal opening in the upper jaw member.

Figure 31A:
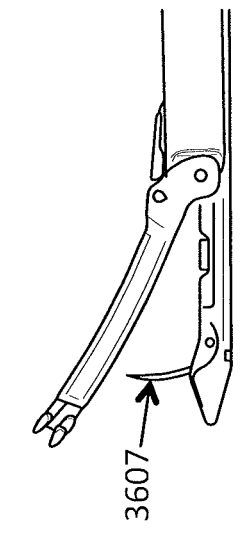
FIGS. 31A-31E illustrate operation of one variation of a suture passer having a tissue penetrator that extends distally from the upper jaw and travels in a sigmoidal path.

FIGS. 31A-31E illustrate another variation of a dual deployment suture passer having a tissue penetrator that is configured to travel in a sigmoidal path and extend distally from a distal opening in the distal end of the device. In this variation, the upper jaw may pivot and the lower jaw extends distally/proximally in the axial direction. A suture (not shown) may be loaded in the upper jaw so that it may be captured by the suture passer and pulled back through the tissue down to the second (lower) jaw member, as described in FIGS. 26A-26C, above. In FIG. 31A, the suture passer is shown in an undeployed state, with the pivoting upper jaw member 3601 at a 45° angle relative to the long axis of the elongate body 3603. As discussed above, in practice the device may be easily inserted into the tissue and adjacent to the target tissue, and the angle of the upper jaw member may be adjusted to help position the device. In this variation the upper jaw is relatively flat (e.g., has a narrow profile).

Figure 31B:
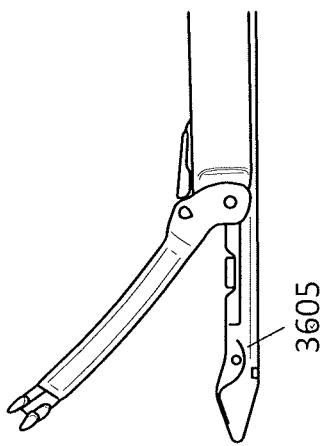
Figure 31C:
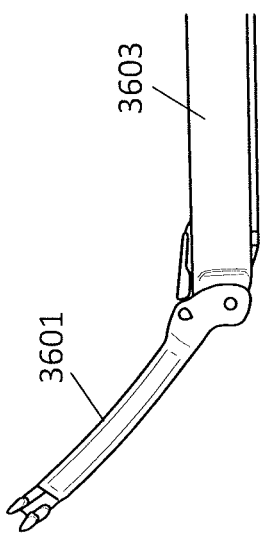
Figure 31E:
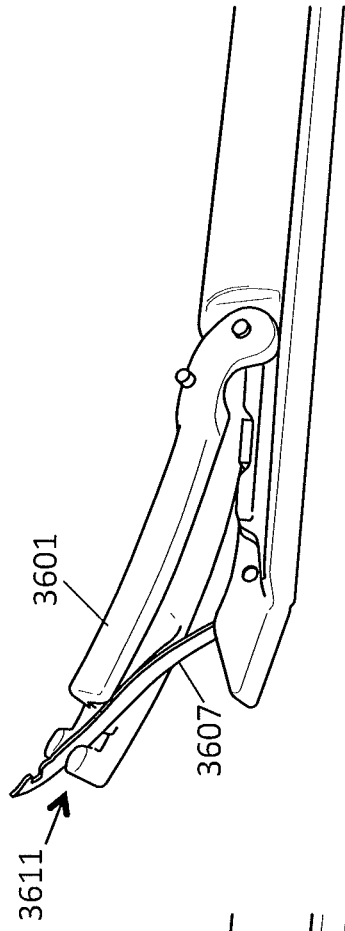
Figure 31D:
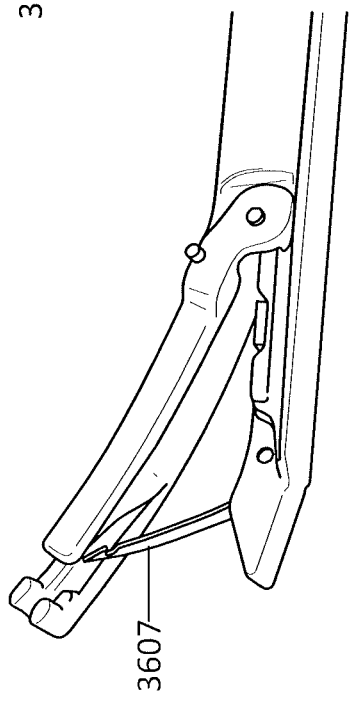

In FIG. 31B, the lower jaw 3605 has been extended distally from the distal end of the elongate body. In FIG. 31C, the upper jaw member has been pivoted downward ("clamping" down) so that the angle relative to the long axis of the elongate body is approximately 30°, and the tissue penetrator 3607 is being extended from the lower jaw 3605 and across the distal-facing mouth to the upper jaw, as also shown in FIG. 31D. The tissue penetrator finally extends distally from the opening 3611 at the distal end of the upper jaw 3601 as shown in FIG. 31E.

Figure 32A:
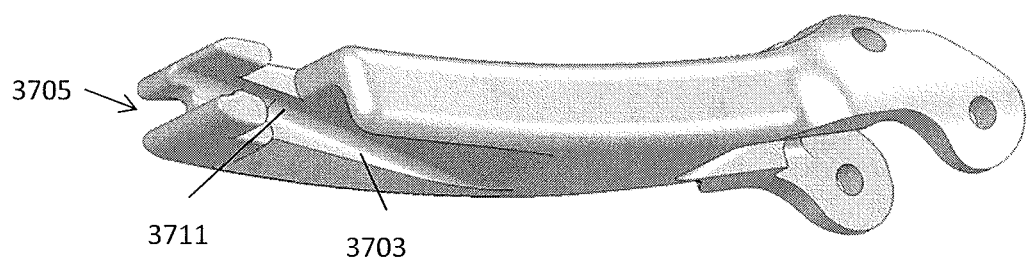
FIGS. 32A and 32B show side perspective views of one variation of an upper jaw member for a suture passer such as the suture passer shown in FIG. 31A.
Figure 32B:
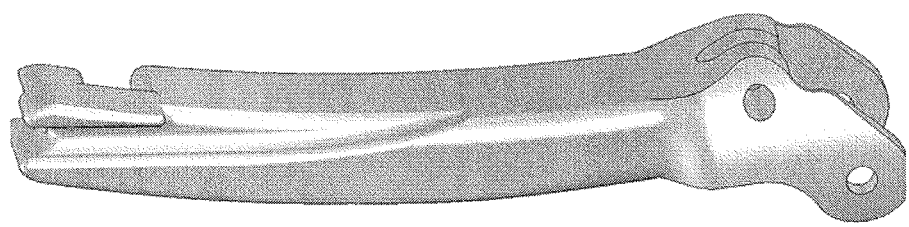

FIGS. 32A and 32B show side and top perspective views, respectively, of one variation of such an upper jaw member. This variation is similar to that shown in FIGS. 31A-31E, and allows loading of a suture on the upper jaw member as previously shown in FIG. 26A-26C. In FIGS. 32A and 32B, the upper jaw member includes a deflection surface 3703 and a distal opening 3705 out of which the tissue penetrator (not shown) may exit distally. The upper jaw shown in FIGS. 32A to 32B also includes a suture loading region 3711 into which one or more sutures may be threaded and/or pre-loaded so that they may be engaged by the tissue penetrator and pulled from the upper jaw to the lower jaw. In this variation the suture loading region is a channel that is adjacent to the deflection surface 3703. A tensioning element (not shown) may be used to hold the suture in the loading region. The tensioning element may be on the upper jaw member, or it may be located more proximally, including on the proximal handle. The tensioning element may be configured to pinch or bind the suture to hold it in position (and in tension) so that it can be engaged by the suture retainer region on the tissue penetrator.

Figure 33A:
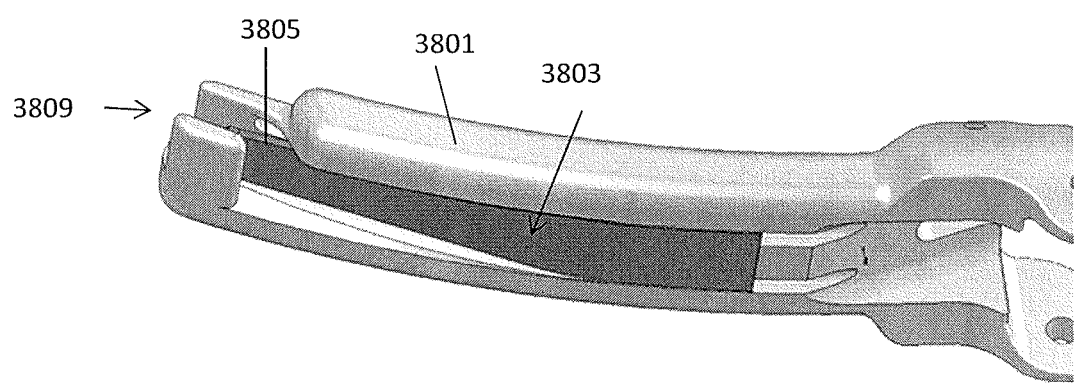
FIGS. 33A and 33B show side perspective views of another variation of an upper jaw member for a suture passer including a suture stripper.
Figure 33B:
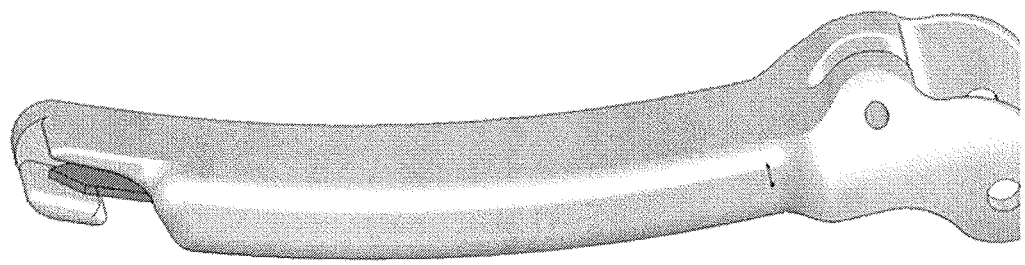

FIGS. 33A and 33B illustrate another variation of the upper jaw member of a suture passer, in which the upper jaw member includes a suture stripper for removing (stripping) the suture off of the suture retainer region of the tissue penetrator and holding the suture (or a loop or bight of suture) in the upper jaw. In FIG. 33A, the upper jaw member 3801 includes a deflector region 3803 that is formed, in part, from the suture stripper 3805. The stripper is formed of a flexible material (e.g., a metal, polymer, or other material, including shape memory alloys) that can be resiliently deflected to allow the tissue penetrator to pass and extend distally from the distal opening 3809, while stripping the suture off of the tissue penetrator and holding the suture in the upper jaw. This is described in more detail below. In FIG. 33A, the suture stripper is configured as a leaf-spring structure that is secured to the upper jaw member at the proximal end and the opposite end is free and held in tension against a distal surface of distal opening at the distal end of the device; the tissue penetrator may push against the stripper and past it, forcing a suture held in the tissue penetrator's retainer region against the stripper. As the tissue penetrator is withdrawn, the suture may be pinched against the stripper and the upper jaw, holding it in place while allowing the tissue penetrator to be withdrawn. In some variations the end of the stripper and/or the distal opening includes an edge (e.g., having serrations, teeth, etc.) to hold the suture as the tissue penetrator is withdrawn.

Figure 34C:
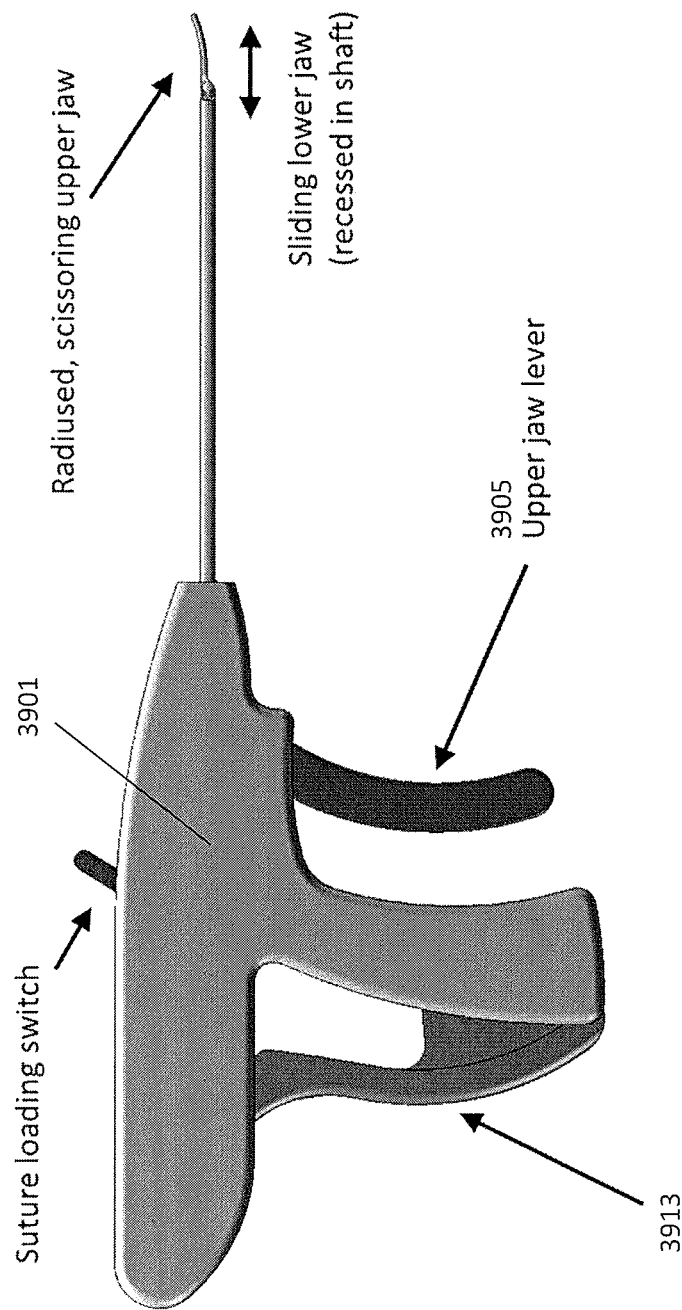

FIGS. 34A-34C illustrate one variation of a suture passer having a tissue penetrator that extends distally from a distal opening in the upper jaw. The tissue penetrator travels in a sigmoidal path from the lower to upper jaw. In this variation, two lengths of a suture (including two lengths of the same suture, e.g., two ends of the same suture) can be loaded into the lower jaw and sequentially passed from the lower jaw, through different regions of the tissue and retained in the upper jaw, to pass a loop of suture through the tissue. The suture passer show in FIGS. 34A-34C is also configured so that the upper jaw member can pivot to assume a different angle relative to the elongate body of the device, and the lower jaw member is axially extendable distally from the distal end of the elongate member to form a distal-facing mouth with the upper jaw member. The proximal handle includes a plurality of controls for controlling the pivoting of the upper jaw member, the axial sliding of the lower jaw member, and the extension/retraction of the tissue penetrator from the lower jaw member.

FIG. 34B shows the device of FIG. 34A with the outer housing of the proximal handle 3901 removed, revealing some of the connections between the controls and the device. In FIG. 34B, the distal most control 3905, the proximal handle is configured as a trigger or lever that controls the motion of the upper jaw member ("upper jaw control"). The upper jaw control may be pulled to reduce the angle of the upper jaw relative to the long axis of the elongate member 3907. In this variation the upper jaw control is pinned and allowed to drive a tendon in the elongate member distally when compressed to drive the upper jaw down (reducing the angle between the upper jaw and the long axis of the elongate member). This pivoting motion may also be referred to as scissoring (scissoring motion).

A distal control 3913 is also configured as a lever or trigger, and may be squeezed or otherwise actuated to extend and/or retract the lower jaw to form a distal-facing mouth with the upper jaw, as shown in FIGS. 34A-34B. In some variations the control is further configured to control deployment of the tissue penetrator in the sigmoidal path. For example, in some variations squeezing the distal control after completely extending the lower jaw may deploy the tissue penetrator from the lower to the upper jaw so that the distal end of the tissue penetrator extends out of the upper jaw. As it extends between the upper and lower jaw, the tissue penetrator may carry a first length (bight) of suture through the tissue. Upon reaching the opposite jaw member, the suture may be removed from the tissue penetrator and held (e.g., by a stripper) in the upper jaw. Upon release of the distal control, the tissue penetrator may withdraw back into the lower jaw. Actuating (e.g., squeezing) the distal control 3913 again may result in the extending the tissue penetrator (along with any second length of suture) back through the tissue from the lower jaw to the upper jaw, where the second length of suture can be retained. Alternately, in some variations, the controls (e.g., to control motion of the upper and/or lower jaw) may be separate from each other, and/or from extending/withdrawing the tissue penetrator. Additional controls may also be included in the proximal handle, include a suture loading control (e.g., switch, toggle, etc.) for loading and/or tensioning the suture within the lower jaw member.

FIGS. 35A-35D show an enlarged view of the distal end of the device of FIGS. 34A-34C. For example, in FIGS. 35A and 35B the upper jaw 4003 is thin and slightly radiused (e.g., curved), and is hinged to the elongate shaft region of the device. The upper jaw is also connected to a control (handle, etc.) on the proximal handle by a push/pull member (tendon, wire, rod, etc.), allowing adjustment of the angle of the upper jaw member relative to the elongate member.

Figure 37B:
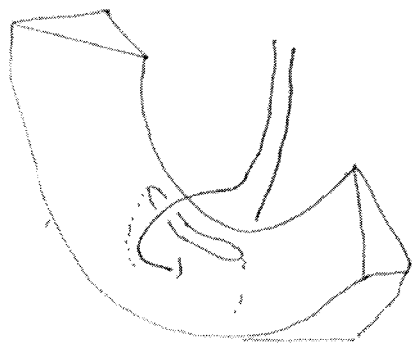
FIGS. 37A and 37B show side perspective views of the distal end region of a jaw member including a suture stripper.
Figure 37A:
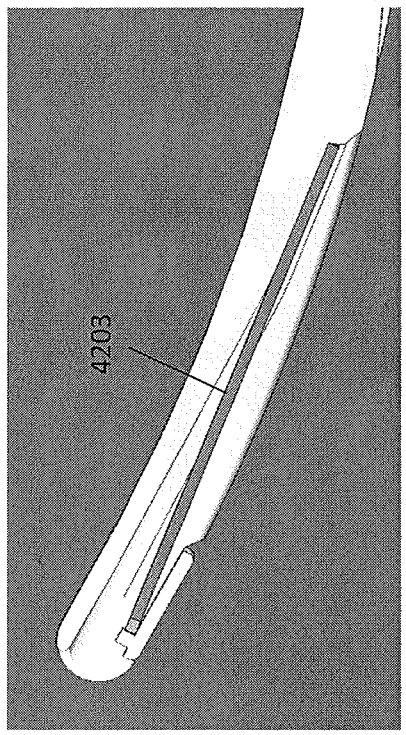

In FIG. 35C, the upper and lower jaw members have been removed from the distal end of the device shown in FIG. 35B, revealing the tissue penetrator 4007 within the lower jaw and the stripper 4009 in the upper jaw. FIG. 35D shows the distal end of the device of FIG. 35B after the tissue penetrator has been extended across the distal-facing mouth. FIGS. 37A and 37B illustrate one variation of an upper jaw region having a suture stripper. In FIG. 37A, the suture stripper is visible from the distal opening at the distal end of the jaw member. In this example, the stripper includes a stripper plate 4203 with a sawtooth edge 4205. The jaw member also includes a receiver region for the stripper plate having a sawtooth edge 4207.

FIGS. 36A-36C show greater detail on one variation of a suture stripper that may be used. This variation is the same as the variation shown in FIGS. 37A and 37B. Although the examples provided herein show the suture stripper in the upper jaw member, in some variations a suture stripper may be present on the lower jaw member (e.g., where the tissue penetrator is configured to pass a length of suture from the upper jaw to the lower jaw). In FIG. 36A, the stripper includes a flexible plate 4101 that is fixed at the proximal end (e.g. to the upper jaw member), and pressed against a receiving plate 4103 at the distal end 4105. In some variations the receiver is not a separate receiving plate, but merely a region of the jaw member. Either or both the suture stripper plate 4101 and the receiver 4103 may include an edge that is adapted to catch the suture. In FIGS. 36A-36C, both the plate 4101 and receiver 4103 include edges having teeth 4105 and 4107. In this example the teeth are saw-tooth structures that are adjacent (or abutting) in the upper jaw member. The tissue penetrator may pass between the plate 4101 and the receiver 4103 by deflecting the plate 4101; as the end of the tissue penetrator passes the edges 4105 and 4107, a length of suture held by the tissue penetrator may be caught by the stripper and held between the plate and receiver as the tissue penetrator is withdrawn.

Returning now to FIGS. 34A-34C, as mentioned above, the device (e.g., in FIG. 34C) has a scissoring upper jaw that is curved (radiused). This curve may be configured to follow the radius of the femoral condyle. The lower jaw in this example is straight. The lower jaw may be recessed into the shaft, and may slide proximal-to-distal in order to slide under the meniscus along the tibial plateau after the upper jaw is in place along the superior surface of the meniscus. The lower jaw contains a flexible needle, which moves vertically from the lower to upper jaw.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of arthroscopically repairing a tissue with a length of suture having a first limb region, a second limb region and a central loop region there between, the method comprising:
    arthroscopically positioning a first jaw of a suture passer on a first side of the tissue and a second jaw of the suture passer on a second side of the tissue;
    extending a needle between the first and second jaws to pass the first limb region of the suture from the first side of the tissue to the second side of the tissue and the second limb region of the suture from the first side of the tissue to the second side of the tissue; and
    passing the first limb region though the central loop region;
    passing the central loop region from the first side to the second side; and
    cinching the central loop region closed.

2. The method of claim 1, wherein the tissue is meniscus tissue and wherein the method further comprises forming a passage through either the tibia or the femur; and
    pulling the first and second limb regions through the passage after cinching the central loop region closed.

3. The method of claim 1, further comprising passing the central loop region from the first side to the second side before cinching the central loop region closed.

4. The method of claim 1, wherein extending the needle between the first and second jaws to pass the second limb region of the suture from the first side of the tissue to the second side of the tissue radially spaces the second limb region from the first limb region.

5. The method of claim 1, further comprising passing the second limb region of the suture through the central loop region before cinching the central loop region closed.

6. The method of claim 1, further comprising anchoring the first and second limb regions to a passage through the tibia or femur.

7. A method of arthroscopically repairing a knee tissue with a length of suture having a first limb region, a second limb region and a central loop region therebetween, the method comprising:
    arthroscopically positioning a first jaw of a suture passer on a superior surface of a meniscus and a second jaw of the suture passer on an inferior surface of the meniscus;
    extending a needle between the first and second jaws to pass the first limb region of the suture from the inferior surface to the superior surface of the meniscus with the suture passer;
    repositioning the first jaw on the superior surface of the meniscus and the second jaw on the inferior surface of the meniscus and extending a needle between the first and second jaws to pass the second limb region from the inferior surface to the superior surface of the meniscus with the suture passer, at a different location than the first limb portion;
    extending at least one of the first and second limb regions through the central loop region; and
    tensioning on at least one of the first and second limb regions to cinch the central loop region around the meniscus.

8. The method of claim 7, further comprising passing the central loop region from the inferior to the superior surface of a meniscus.

9. The method of claim 8, wherein extending the first limb region of the suture from the inferior to the superior surface of the meniscus with the suture passer is performed before passing the central loop region from the inferior surface to the superior surface.

10. The method of claim 7, further comprising arthroscopically positioning the suture passer with the first jaw between the superior surface of the meniscus and a femur and the second jaw between the inferior surface and a tibia.

11. A method of arthroscopically repairing a knee tissue with a length of suture having a distal limb region, a proximal limb region and a central loop region therebetween, the method comprising:
    arthroscopically positioning a first jaw of a suture passer on a superior side of a meniscus and a second jaw of the suture passer on an inferior side of the meniscus;
    extending a needle between the first and second jaws to pass a first loop of the distal limb region of the suture from the inferior to the superior surface of a meniscus with the suture passer;

extending the needle between the first and second jaws to pass a first loop of the proximal limb region of the suture from the inferior to the superior surface of a meniscus with the suture passer, at a location radially spaced from the first loop of the distal limb region;

passing the distal limb region though the central loop region; and passing the central loop region from the inferior side to the superior side and cinching the central loop region closed.

12. The method of claim 11, further comprising anchoring the distal limb region and the proximal limb region to the tibia.

13. The method of claim 11, further comprising forming a channel in the tibia to anchor the suture.

14. The method of claim 11, further comprising passing the proximal limb region through the central loop.

15. The method of claim 11, further comprising passing the central loop region from the inferior side to the superior side before passing the distal limb region though the central loop region.

16. The method of claim 15, wherein passing the central loop region from the inferior side to the superior side comprising passing the central loop region through the meniscus.

17. The method of claim 16, wherein the central loop region is passed through the meniscus at a location radially spaced from the first loop of the distal limb region and the first loop of the proximal limb region.

18. The method of claim 16, wherein the central loop region is cinched closed by applying tension to at least the distal limb region.

19. A method of arthroscopically repairing a tissue with a length of suture having a first limb region, a second limb region and a central loop region there between, the method comprising:

arthroscopically positioning a first jaw of a suture passer on a first side of the tissue and a second jaw of the suture passer on a second side of the tissue;

extending a needle between the first and second jaws to pass the first limb region of the suture from the first side of the tissue to the second side of the tissue;

arthroscopically repositioning the first jaw on the first side of the tissue and the second jaw on the second side of the tissue and extending the needle between the first and second jaws to pass the second limb region from the first side to the second side through a different portion of the tissue than the first limb region; and passing the first limb region though the central loop region; and cinching the central loop region closed.

* * * * *